US012773436B2

(12) United States Patent
Mueller et al.

(10) Patent No.: US 12,773,436 B2
(45) Date of Patent: Oct. 27, 2026

(54) RECOMBINANT RHABDOVIRUS ENCODING FOR A CD80 EXTRACELLULAR DOMAIN Fc-FUSION PROTEIN

(71) Applicant: Boehringer Ingelheim International GmbH, Ingelheim am Rhein (DE)

(72) Inventors: Philipp Mueller, Mittelbiberach (DE); Klaus Erb, Mittelbiberach (DE); Patrik Erlmann, Goetzens (AT); Guido Wollmann, Innsbruck (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 155 days.

(21) Appl. No.: 18/937,207

(22) Filed: Nov. 5, 2024

(65) Prior Publication Data

US 2025/0057900 A1 Feb. 20, 2025

Related U.S. Application Data

(62) Division of application No. 17/336,351, filed on Jun. 2, 2021, now Pat. No. 12,171,795.

(30) Foreign Application Priority Data

Jun. 3, 2020 (EP) .................................... 20178032

(51) Int. Cl.

| | |
|---|---|
| ***A61K 35/766*** | (2015.01) |
| ***A61K 45/06*** | (2006.01) |
| ***C07K 14/705*** | (2006.01) |

(52) U.S. Cl.

CPC ............ *A61K 35/766* (2013.01); *A61K 45/06* (2013.01); *C07K 14/70532* (2013.01); *C07K 2319/02* (2013.01); *C07K 2319/30* (2013.01)

(58) Field of Classification Search

CPC .. A61K 35/766; A61K 45/06; A61K 31/4709; A61K 31/5377; A61K 2300/00; C07K 14/70532; C07K 2319/02; C07K 2319/30; C07K 14/005; C12N 7/00; C12N 2760/10022; C12N 2760/20032; C12N 2760/20043; C12N 2760/20232; C12N 2760/20243; C12N 2760/20245; C12N 15/86; Y02A 50/30; A61P 35/00

See application file for complete search history.

(56) References Cited

U.S. PATENT DOCUMENTS

| | | | |
|---|---|---|---|
| 8,008,449 | B2 | 8/2011 | Korman et al. |
| 8,354,509 | B2 | 1/2013 | Carven et al. |
| 2002/0182733 | A1 | 12/2002 | Naldini et al. |
| 2009/0175906 | A1 | 7/2009 | Kalyan et al. |
| 2011/0250188 | A1 | 10/2011 | Von Laer et al. |
| 2016/0296572 | A1 | 10/2016 | Van Den Pol et al. |
| 2022/0227833 | A1 | 7/2022 | Song et al. |

FOREIGN PATENT DOCUMENTS

| | | | |
|---|---|---|---|
| CN | 101981182 | A | 2/2011 |
| CN | 108728488 | A | 11/2018 |
| CN | 108883187 | A | 11/2018 |
| CN | 109415706 | A | 3/2019 |
| CN | 110218707 | A | 9/2019 |
| WO | 2001254450 | | 4/2001 |
| WO | 2002072851 | A3 | 10/2003 |
| WO | 2005035773 | | 4/2005 |
| WO | 2005098009 | A2 | 10/2005 |
| WO | 2006008074 | A1 | 1/2006 |
| WO | 2006121168 | A1 | 11/2006 |
| WO | 08016893 | A1 | 2/2008 |
| WO | 2009082664 | A2 | 7/2009 |
| WO | 2009101611 | A1 | 8/2009 |
| WO | 2009114335 | A2 | 9/2009 |
| WO | 2010040526 | A1 | 4/2010 |
| WO | 2013127729 | A1 | 9/2013 |
| WO | 2015025018 | A1 | 2/2015 |
| WO | 2015025019 | A1 | 2/2015 |
| WO | 2015112900 | A1 | 7/2015 |
| WO | 2016023858 | A1 | 2/2016 |
| WO | 2017019896 | A1 | 2/2017 |
| WO | 2017079117 | A1 | 5/2017 |
| WO | 2017143449 | A1 | 8/2017 |
| WO | 2017181152 | | 10/2017 |
| WO | 2017197525 | A1 | 11/2017 |
| WO | 2017198741 | A1 | 11/2017 |
| WO | 2018170026 | A2 | 9/2018 |
| WO | 2020047087 | A1 | 3/2020 |
| WO | 2021072284 | A2 | 4/2021 |

OTHER PUBLICATIONS

Schildberg, Immunity, Cohinitory Pathways in the B7-CD28 Ligand-Receptor Family, vol. 44, 2017.

Lichty, perspectives, Ging Viral with Viral cancer Immunotherapy, vol. 14, 2014.

Liu, Combination B7-Fc Fusion Protein Treatment and Treg Cell Deptetion Therapy, Clin. Cancer Research. Vol. 11, p. 492-498, 2005.

Reul, Dissertation, Viral gene transfer systems for cancer immunotherapy, 2018.

Smith, Cancer, Immunotherapy, Cancer-Vaccines, Genetic Engineering of Hematopoietic Stem Cells to Generate Invariant Natural Killer y Cells, 2018.

Pickup, NIH, The roles of TGFβ in the tumor microenvironment, 2013.

Deng, MABS, Preclinical Pharmacokinetics, pharmacodynamics, tissue distribution, and tumor penetration, vol. 8, 2016.

(Continued)

*Primary Examiner* — Peter Paras, Jr.
*Assistant Examiner* — Khoa Nhat Tran
(74) *Attorney, Agent, or Firm* — Wendy M. Gombert

(57) ABSTRACT

The present invention relates to the field of oncolytic viruses and in particular to a recombinant rhabdovirus, such as vesicular stomatitis virus encoding in its genome for a CD80 extracellular domain Fc-fusion protein. The invention is further directed to the use of the recombinant virus in the treatment of cancer, and also to methods for producing such viruses.

13 Claims, 24 Drawing Sheets

Specification includes a Sequence Listing.

(56) References Cited

OTHER PUBLICATIONS

Calon, Nature Genetics, Stromal geneexpression defines poor prognosis subtypes in colorectal cancer, vol. 47, 2013.
Boyerinas, Cancer immunol. Res., Antibody-dependent cellular cytotoxicity, vol. 3, 2015.
Ryner, Clinical Cancer Research, Upregulation of Periostatin and reactive stroma is associated with primary chemoresistance, 2015.
Tothill, Clinical Cancer Research, Novel Molecular Subtypes of Serous and Endometroid Ovarian Cancer, vol. 14, 2008.
Stewart, Cancer Immunol. Research, Id and Characterization of MEDI4736, vol. 3, 2016.
Ibrahim, PD-LI Blockade for Treatment, Semin, Oncol.,2015.
Walker, J. of Gem. Virology, ICTV Virus Taxonomy Profile, 2018.
Muik, Cancer Research, Re-engineering Vesicular Stomatitis Virus to Abrogate Neurotoxicity, 2014.
Penheiter, Current Gene Therapy, The Sodium Iosise Supporter, vol. 12 , 2012.
Karlin, Proc. Natl., Acad. Science, Methods for assessing the statisitcal significance of molecular sequence features, vol. 87, 1990.
Altschul, J. Molecular Biol., Basic Local Alignment Search tool, vol. 15, 1990.
Altschul, Nucleic Acids Research, Gapped BLAST and PSI BLAST, vol. 25, 1997, p. 3389-3402.
Torelli, Cabios, Advance and ADAM: 2 algorithms for the analysis of global similarity between homologous informational sequences, 1994.
Pearson, Proc. Natl. Acad, Sci, Improved Tools for Biological sequence Comparison, vol. 85, 1988.
Schnell, J. of Virology, The minimal Conserved Transcription stop start signal promotes stable expression of a foreign gene, vol. 70, 1996.
Higgins, Methods in Enzymology, Using Clustal for Multiple Signal Alignments, vol. 266, 1996.
Li, Int. J. of Molecular Sciences, A mini Review for Cancer immunotherapy, 2016.
Hamid, NE J. of Medicine, Safety and Tumor responses, 2013.
International Search Report and Written Opinion mailed on Aug. 24, 2021 for PCT/EP2021/064728.
Abstract cited herein for CN 108728488 dated 2018.
Reul, Viral gene transfer systems for cancer immunotherapy: semireplication-competent VSV and receptor-targeted AAV for the delivery of immunomodulatory proteins, vom Fachbereich Biologie der Technischen Universitat Darmstadt zur Erlangung des akademischen Grades, 2018, vol. 1, p. 1-166.
Smith, Genetic Engineering of Hematopoietic Stem cells to generate invariant Natural Killer T Cells, Cancer-Immunotherapy, Cancer Vaccines I, vol. 24, 2016, p. 1.
Liu, Combination B7-Fc Fusion Protein Treatment and Treg Cell Depletion Therapy, Cancer Therapy: Preclinical, 2005, vol. 23, p. 8492-8502.
Miletic, H., et al., “Selective transduction of malignant glioma by lentiviral vectors pseudotyped with lymphocytic choriomeningitis virus glycoproteins”, Hum Gene Ther., Nov. 2004, vol. 15, No. 11, pp. 1091-1100.
Ackermann, Pre clinical assessment of the therapeutic potential of a CD80-Fc-armed oncolytic virus (VSV-GP-CD80Fc), Annals of Oncology, vol. 34, 2023, p. 1170-1171.
Chaudhri et al., PD-L1 binds to B7-1 only in Cis on the Same cell Surface, Cancer immunol Res., vol. 6, 2018, p. 921-929.

FIG.3A-B
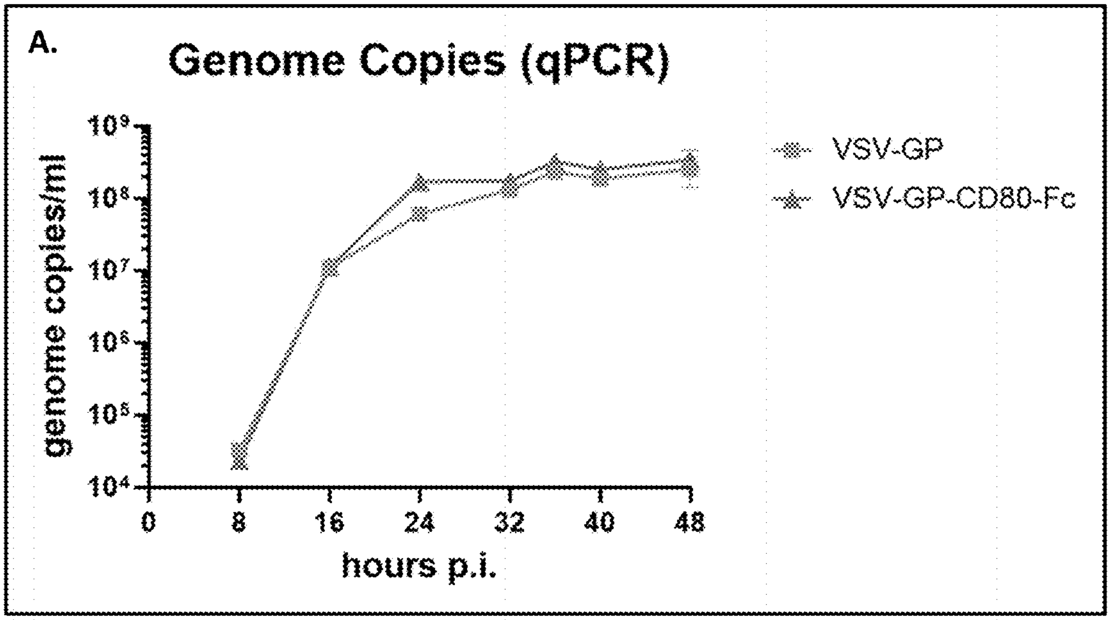
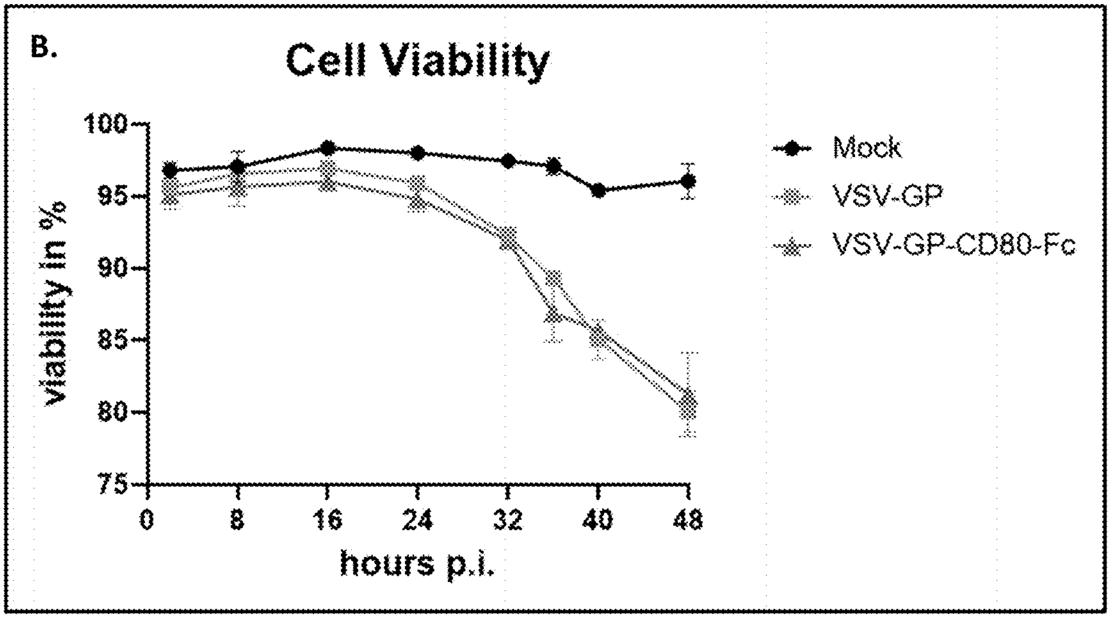

FIG.5A-B
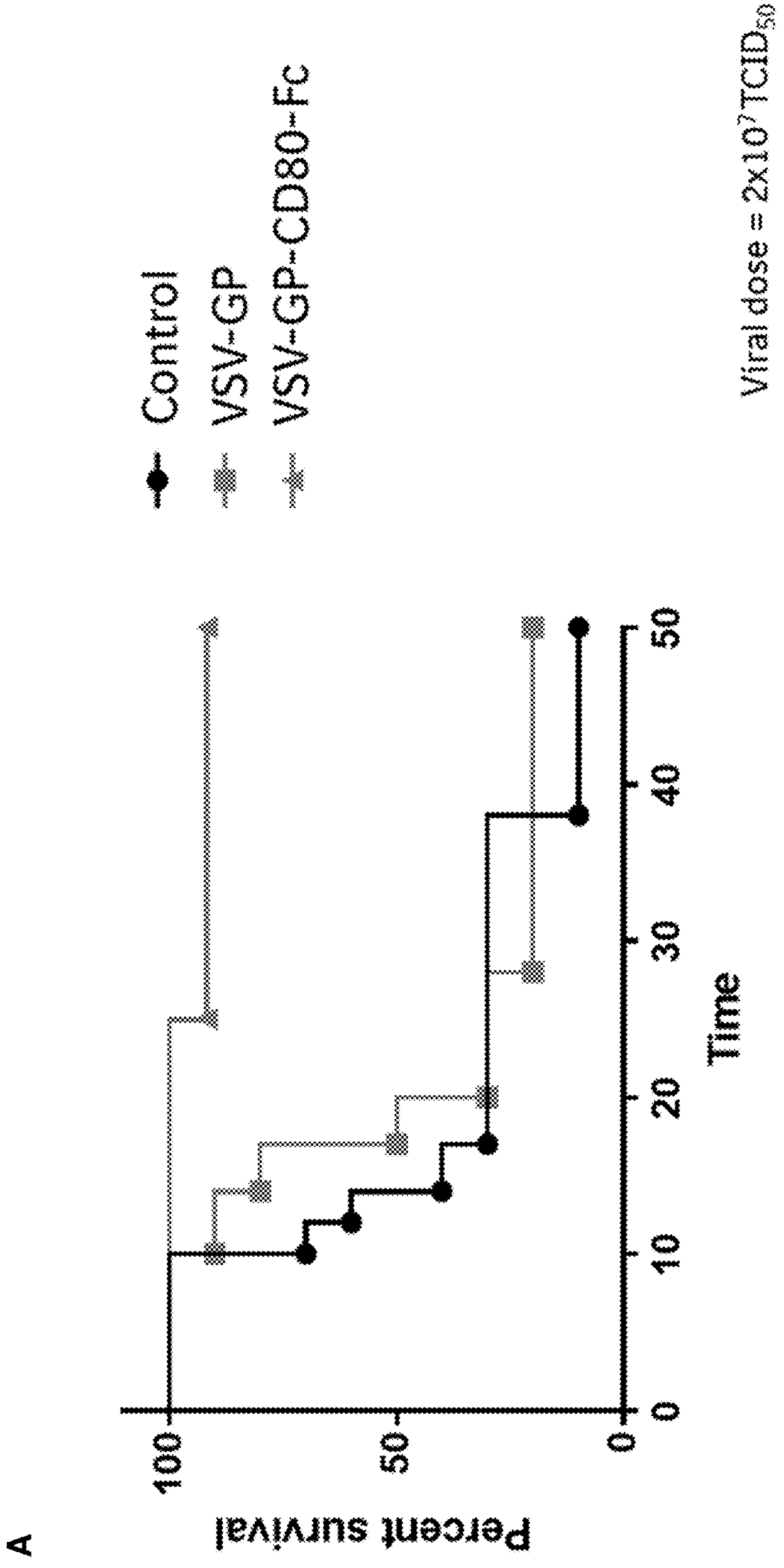

FIG.5A-B cont.
B
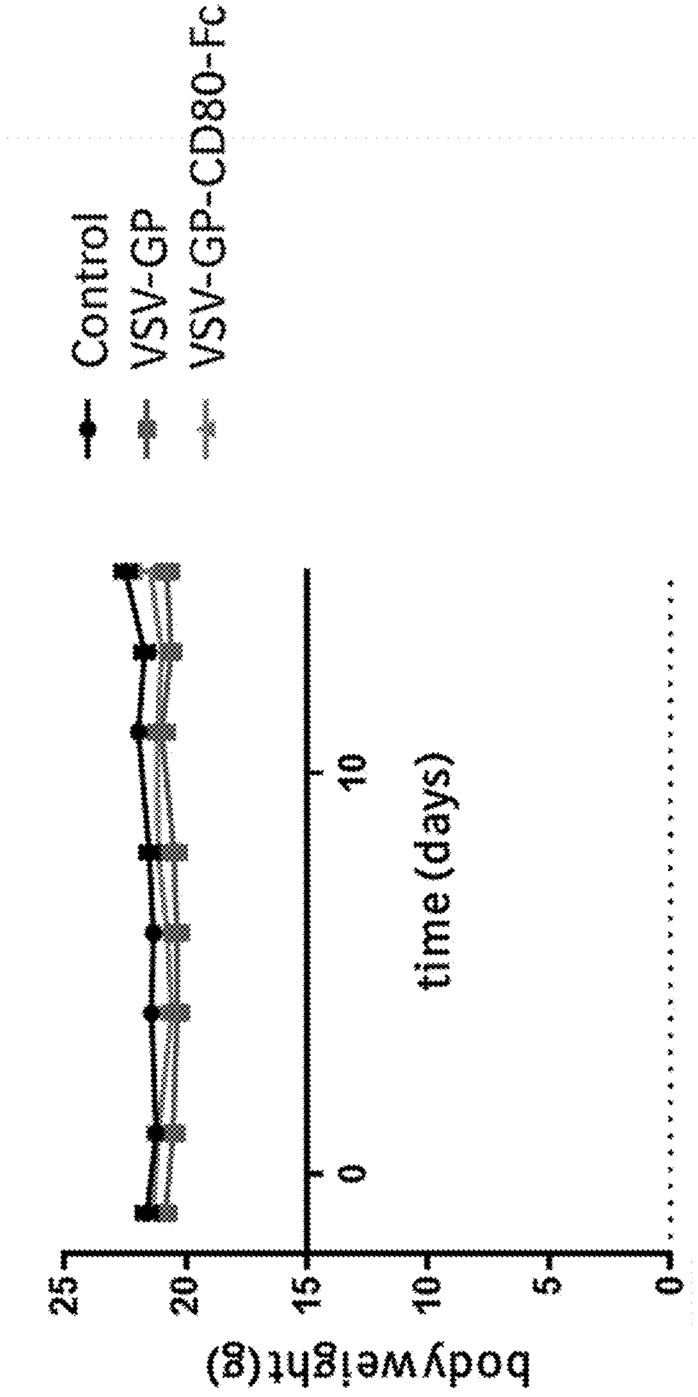

FIG.6A-C
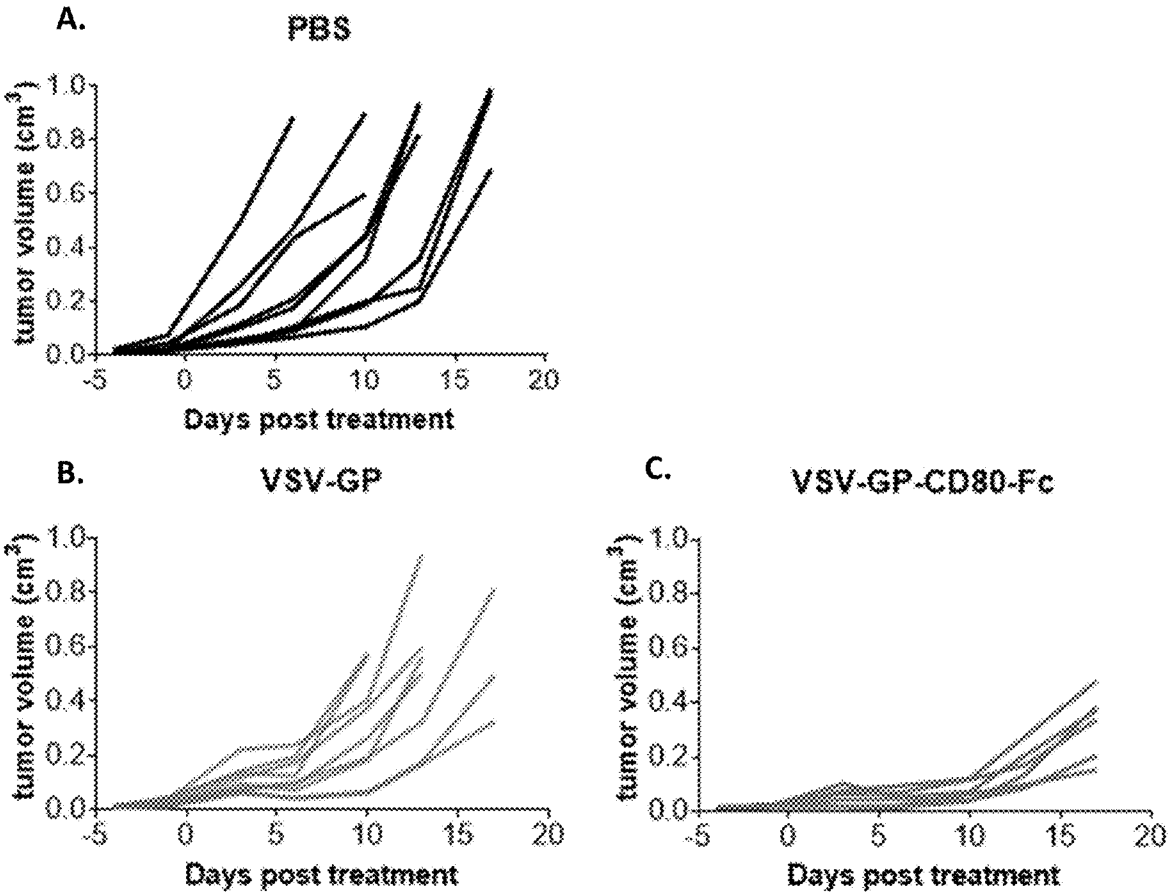

FIG.7A-B
A.
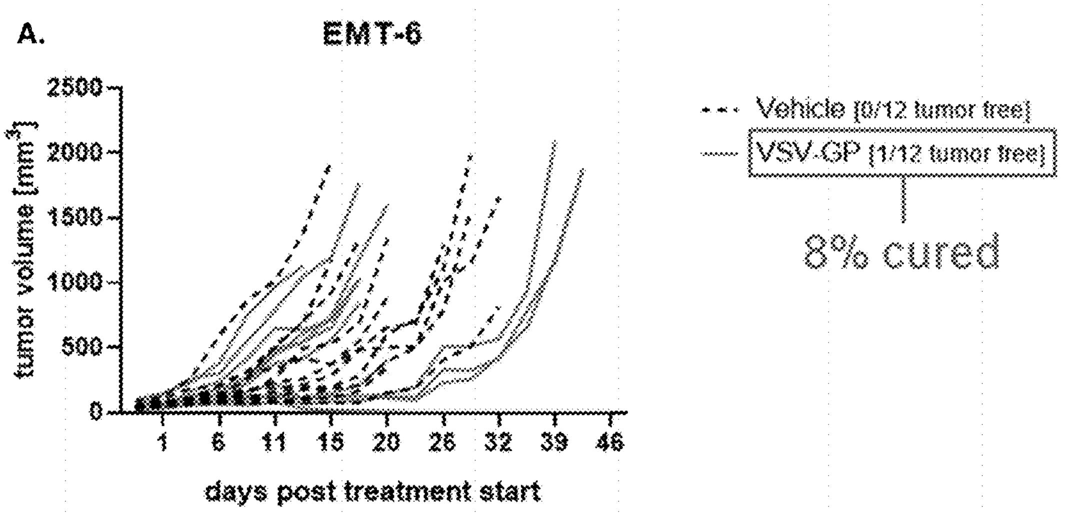
B.
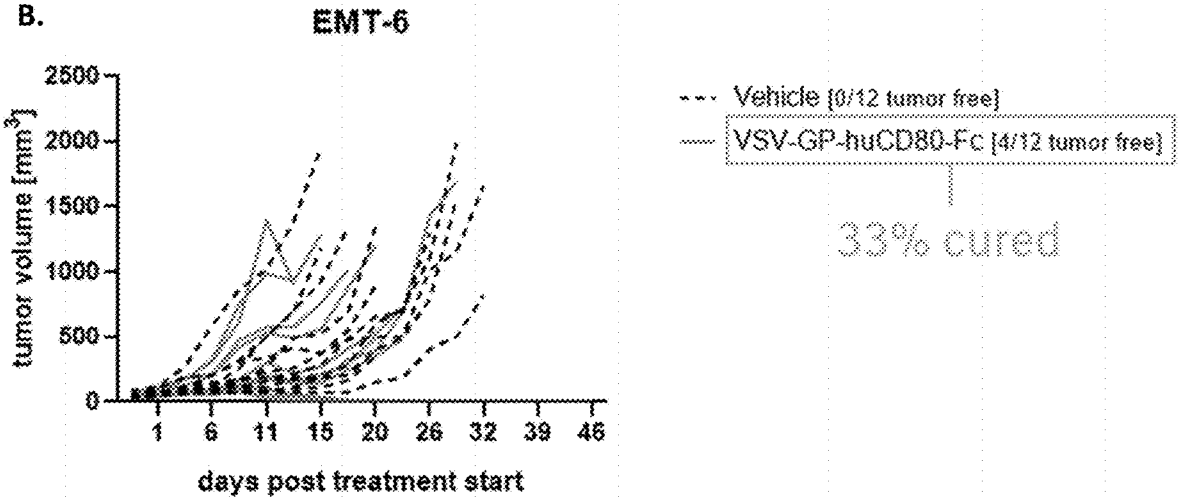

FIG.11A-C

FIG. 13A-D
A
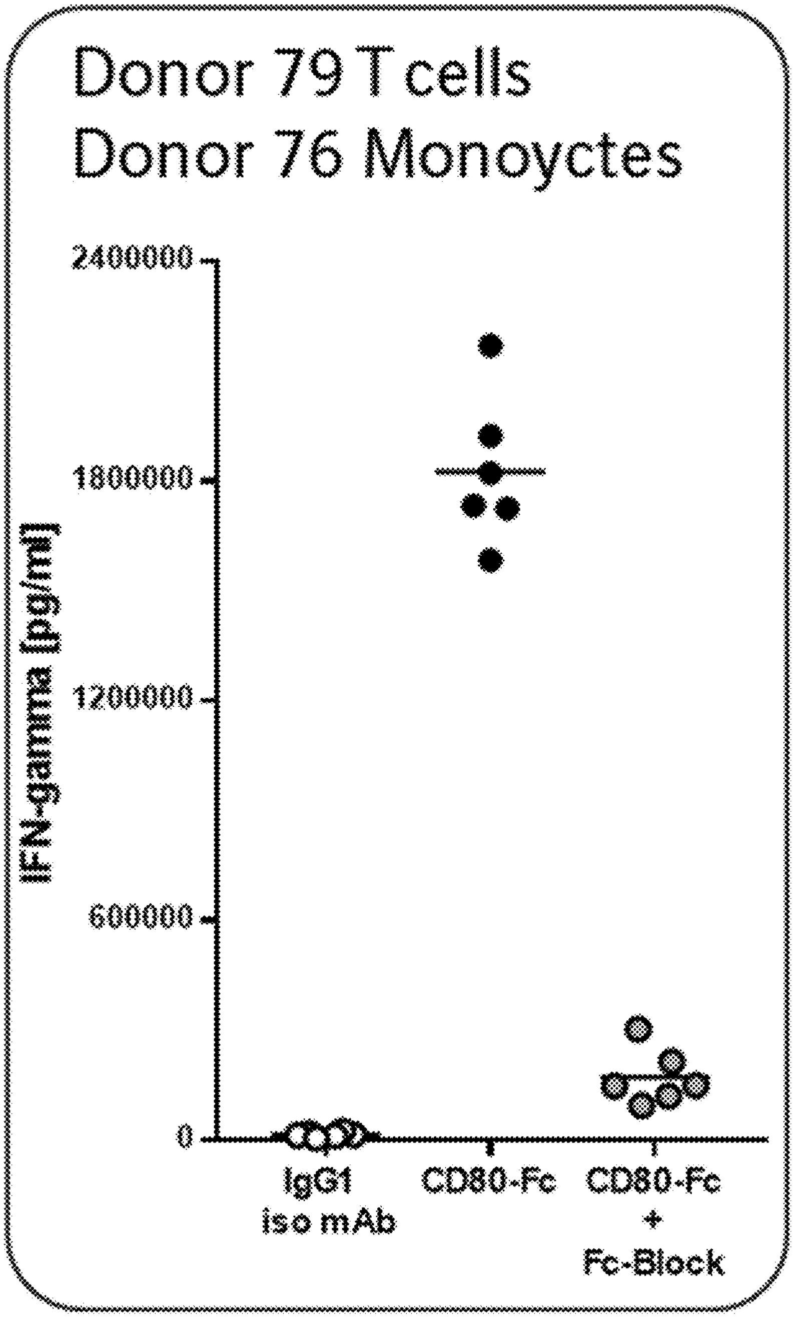

FIG. 13A-D cont.
B
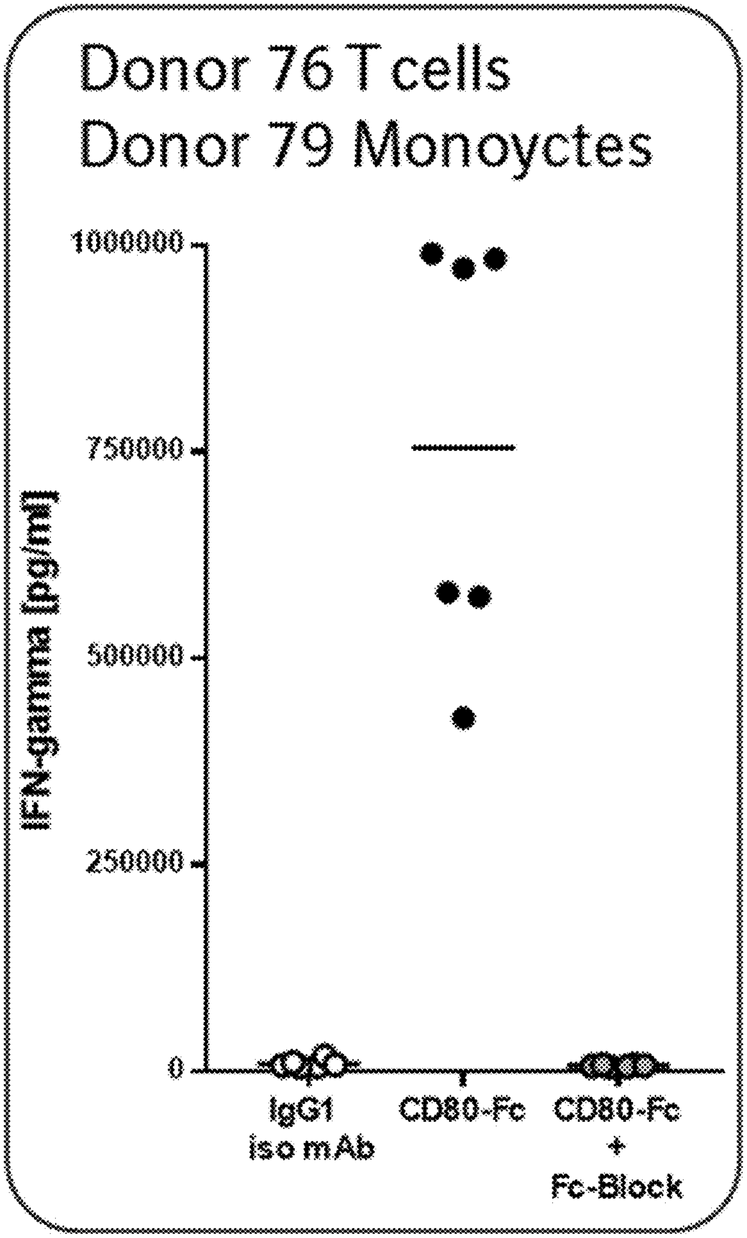

FIG. 13A-D cont.
C
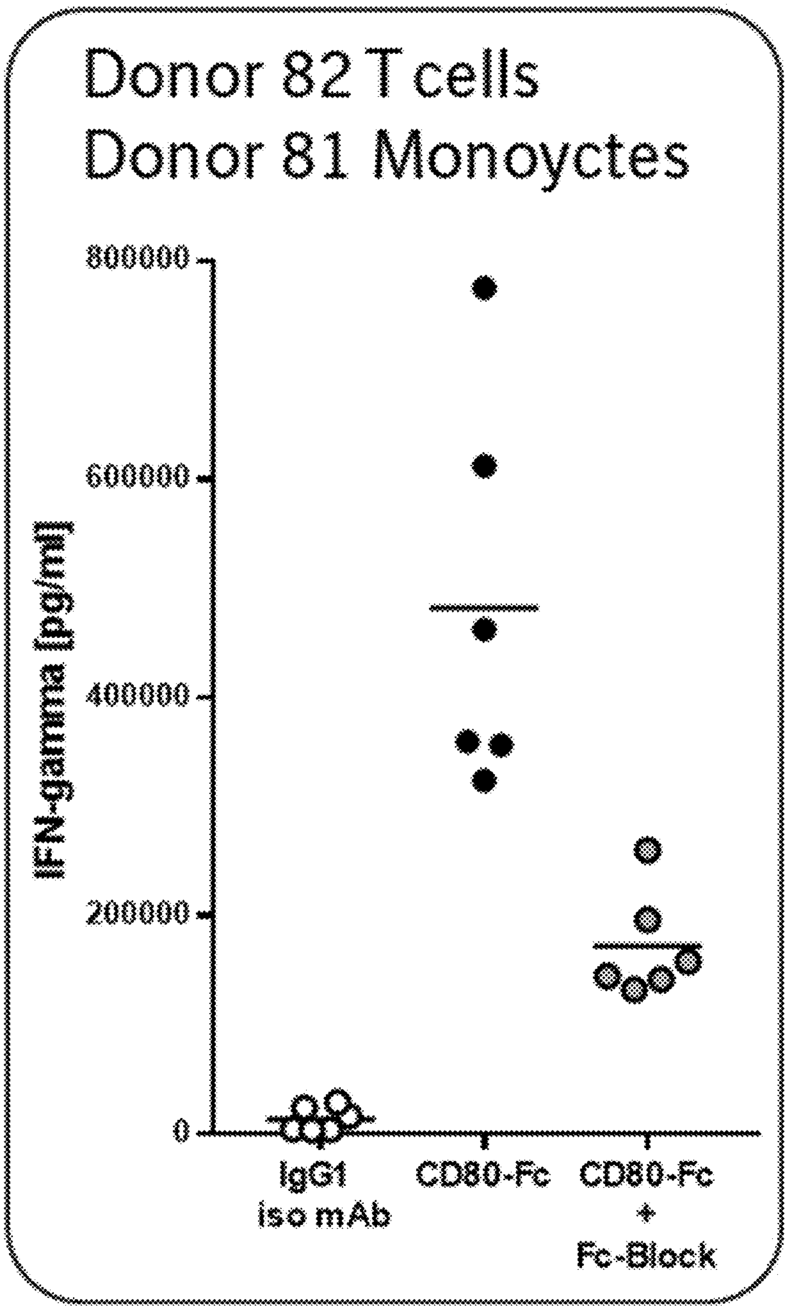

FIG. 13A-D cont.
D
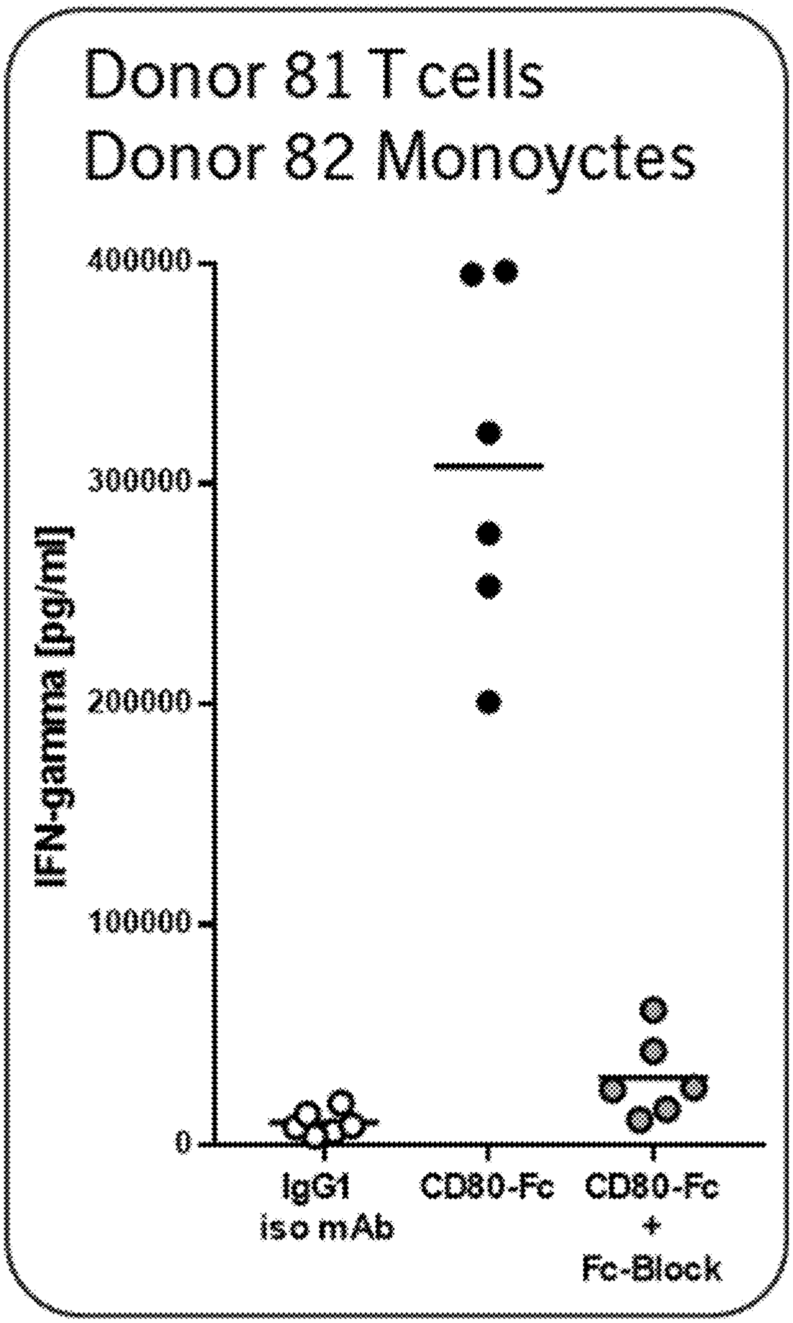

FIG.14A-F
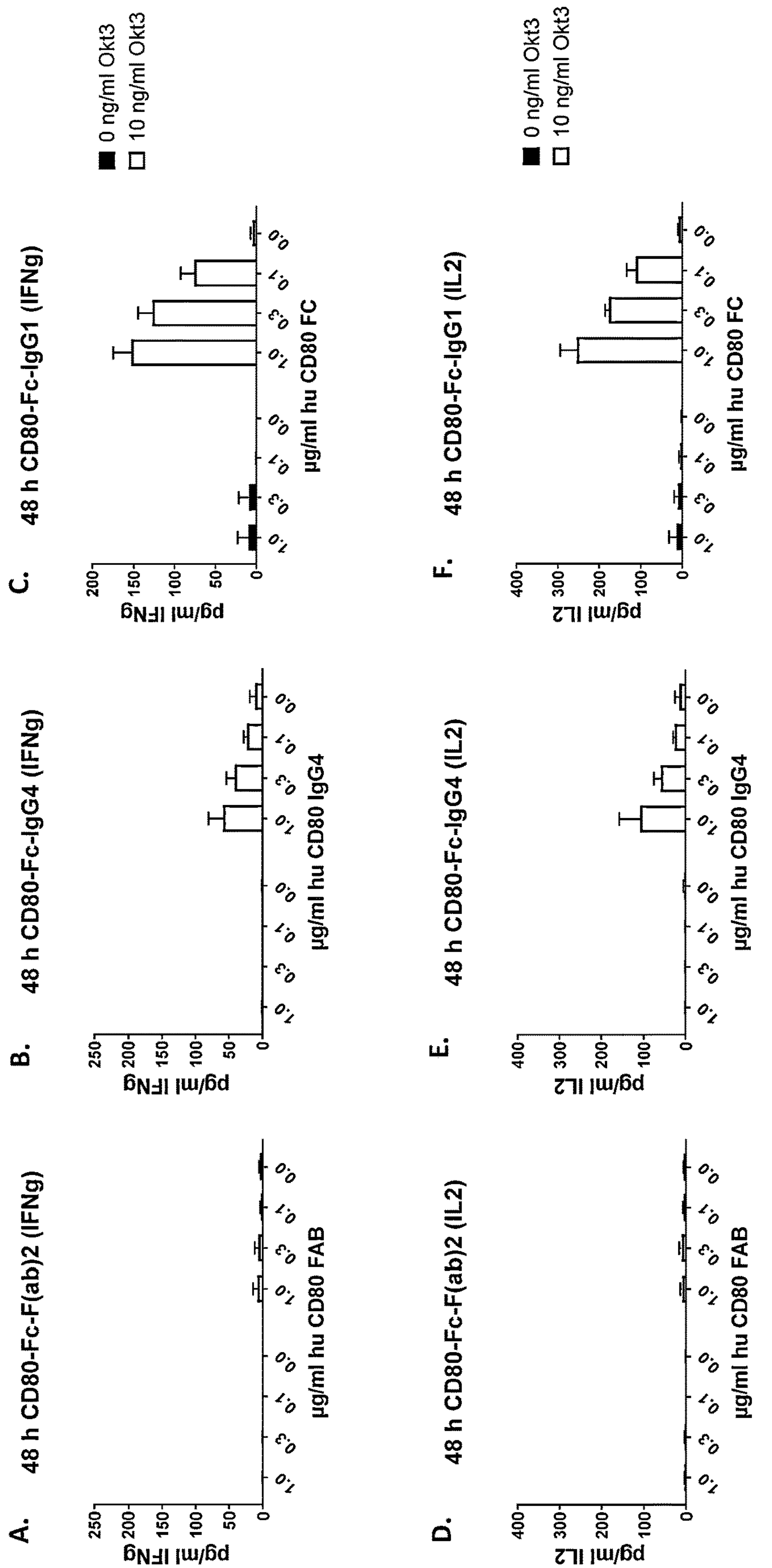

FIG.16A-C
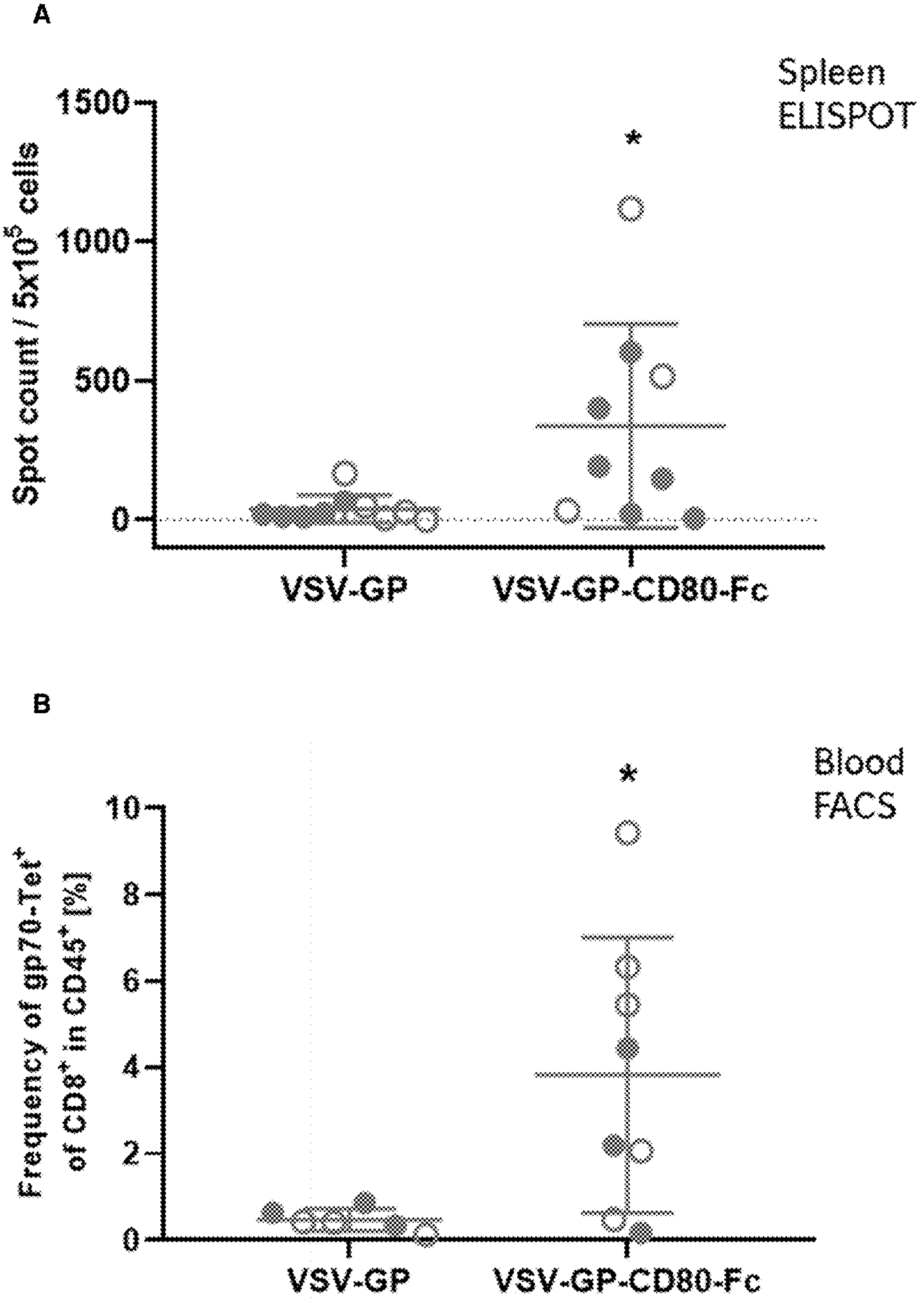

FIG.16A-C cont.
C
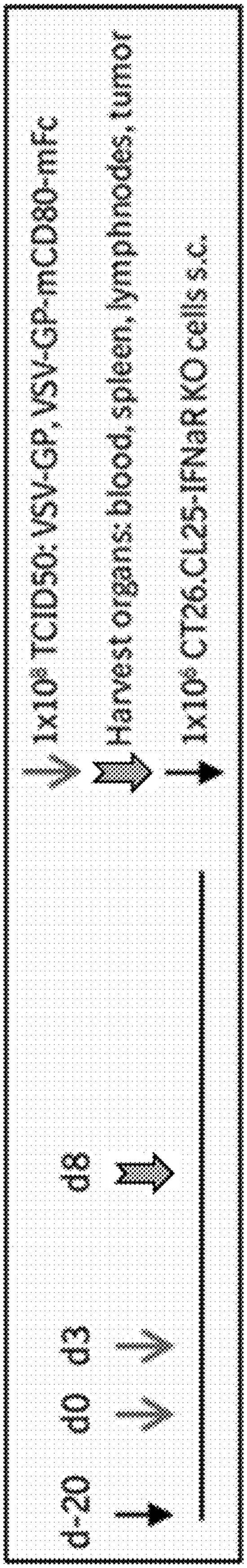

FIG.18A-B
A
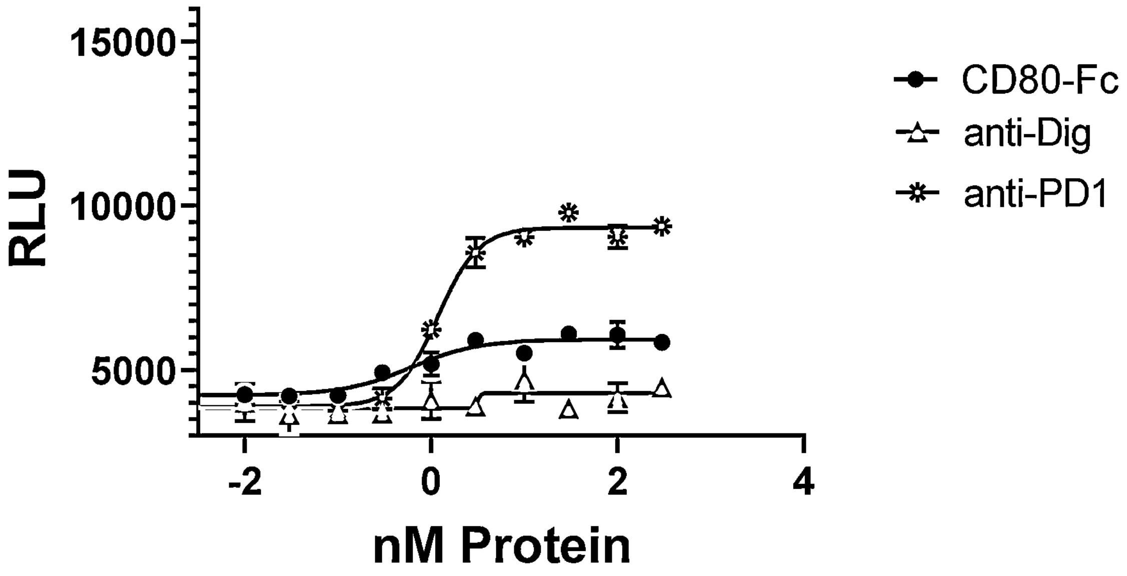
B
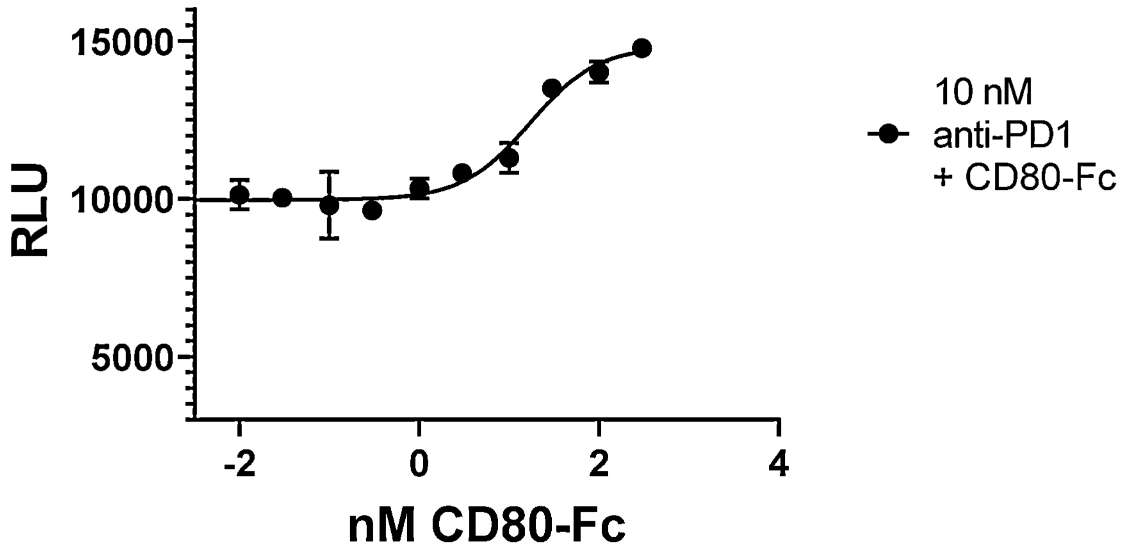

FIG.19A-C
A
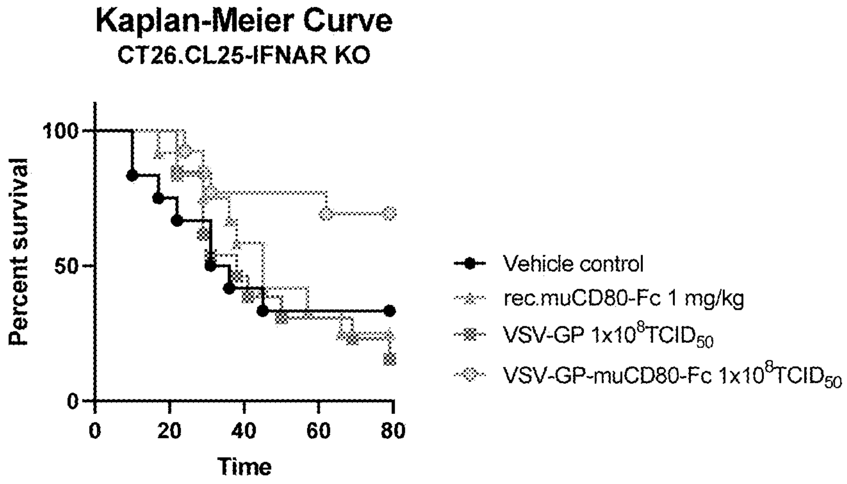
B
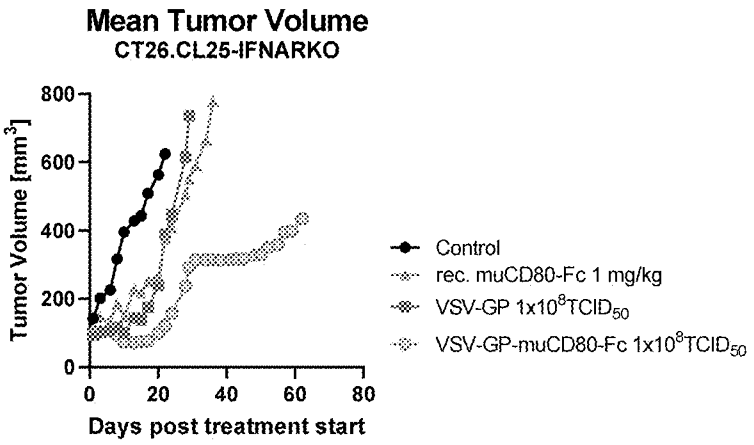
C
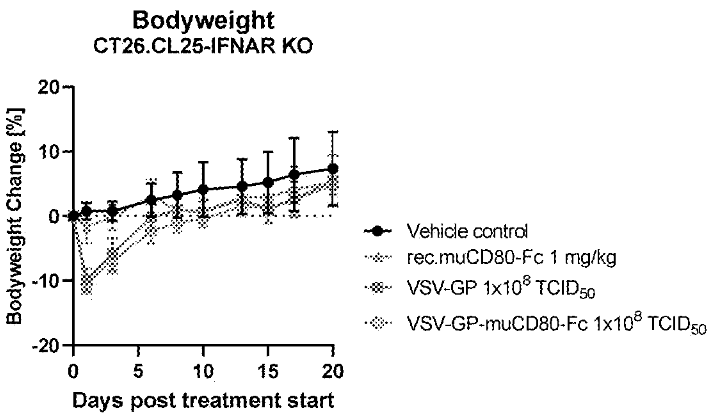

RECOMBINANT RHABDOVIRUS ENCODING FOR A CD80 EXTRACELLULAR DOMAIN Fc-FUSION PROTEIN

SEQUENCE LISTING

The instant application contains a Sequence Listing which has been submitted electronically in XML format and is hereby incorporated by reference in its entirety. Said XML copy, created on Oct. 22, 2024, is named 01-3411-US-2_SL.xml and is 44,033 bytes in size.

FIELD OF THE INVENTION

The present invention relates to the field of oncolytic viruses and in particular to a recombinant rhabdovirus encoding in its genome for a CD80 extracellular domain Fc-fusion protein. The invention is further directed to the use of the recombinant rhabdovirus in the treatment of cancer, and to methods for producing such viruses.

BACKGROUND OF THE INVENTION

Oncolytic viruses are an emerging class of biologicals, which selectively replicate in and kill cancer cells and are able to spread within tumors. Efforts to further improve oncolytic viruses to increase their therapeutic potential has led to the development of so called armed viruses, which encode in their genome tumor antigens or immune modulatory transgenes to improve their efficacy in tumor treatment.

In many cases there is a paucity of T cells in tumors and therefor there exists what has become known as "immune deserts"—a tumor microenvironment where the immune system's T cells cannot or do not penetrate the tumor to kill the cells growing out of control. It has been postulated that to evade immune surveillance, tumors create an immunosuppressive microenvironment by recruiting myeloid-derived suppressor cells or secrete factors including TGFβ, which play a dual role of inducing the expression of extracellular matrix genes and suppressing the expression of chemokines and cytokines required to facilitate T-cell infiltration into tumors (Pickup M, Novitskiy S, Moses H L. The roles of TGFbeta in the tumour microenvironment. Nat Rev Cancer 2013; 13:788-99). Furthermore, studies have found that tumors exhibiting high expression of genes which correspond to an immunosuppressive microenvironment are associated with poor outcomes across a number of cancer types, including ovarian cancer and colorectal cancer (Calon A, Lonardo E, Berenguer-Llergo A, Espinet E, Hernando-Momblona X, Iglesias M, et al. Stromal gene expression defines poor-prognosis subtypes in colorectal cancer. Nat Genet 2015; 47:320-9; Ryner L, Guan Y, Firestein R, Xiao Y, Choi Y, Rabe C, et al. Upregulation of periostin and reactive stroma is associated with primary chemoresistance and predicts clinical outcomes in epithelial ovarian cancer. Clin Cancer Res 2015; 21:2941-51; Tothill R W, Tinker A V, George J, Brown R, Fox S B, Lade S, et al. Novel molecular subtypes of serous and endometrioid ovarian cancer have been linked to clinical outcome. Clin Cancer Res 2008; 14:5198-208). The hallmarks of the adaptive immune response are specificity and memory. The cellular response is mediated by T-cells, which express cell surface T-cell receptors (TCRs) that recognize peptide antigens in complex with major histocompatibility complex (MHC) molecules on antigen presenting cells (APCs). However, interaction of cognate TCRs with MHC-peptide complexes alone (signal 1) does not trigger optimal T-cell activation. In addition to signal 1, the binding of positive and negative costimulatory receptors to their cognate ligands modulates T-cell activation. This complex signaling network on the one hand provides optimal T-cell activation, while on the other hand aberrant activation of T-cells under physiological conditions is prevented. CD28 (signal 2) is the main positive co-stimulatory receptor on T-cells. When signal 2 (CD28 interaction with B7.1 (CD80) or B7.2 (CD86)) is lacking, for instance on TAA-presenting tumor cells, chronic interactions with TAA-specific T-cells render the latter non-responsive (anergic): the T-cell becomes refractory to signals even when the TCR interacts with TAAs. This situation has been described in cancer patients, especially in chronic situations of advanced disease. Strong T-cell co-stimulation may however reactivate TAA-specific T-cells in late-stage metastasized cancer patients.

One recent approach foresees an oncolytic virus that encodes in its genome the IFN-β protein as a cargo. In a further approach expression of the tumor antigen MAGE-A3 is being explored in the clinic. In addition to identifying a suitable and effective cargo, the expression of additional cargos from a viral backbone, always carries the risk that it will not only potentiate anti-tumor efficacy but also anti-viral immunity. Care has to be taken that the cargo does not restrict the oncolytic potential of the virus to a degree where the benefit gained by expression of the therapeutic cargo is negated by the loss of oncolytic potency. Thus, there is a need in the art for further improved armed oncolytic viruses that can be used in effective cancer treatments. There is further a need in the art to selectively improve T-cell and/or dendritic cell infiltration into immunosuppressive tumor microenvironments.

SUMMARY OF THE INVENTION

The present invention addresses the above needs by providing a recombinant rhabdovirus, such as a vesicular stomatitis virus, which encodes in its genome a CD80 extracellular domain Fc-fusion protein or a functional variant thereof, preferably a human CD80 extracellular domain.

It is to be understood that any embodiment relating to a specific aspect might also be combined with another embodiment also relating to that specific aspect, even in multiple tiers and combinations comprising several embodiments to that specific aspect.

In a first aspect, the present invention relates to a recombinant rhabdovirus encoding in its genome at least one CD80 extracellular domain Fc-fusion protein or a functional variant thereof, wherein the CD80 extracellular domain Fc-fusion protein comprises the extracellular domain of CD80 and further comprises the Fc domain of an IgG.

In one embodiment relating to the first aspect, the CD80 extracellular domain Fc-fusion protein or functional variant thereof is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, (vii) a CD80 extracellular domain Fc-fusion protein, comprising SEQ ID NO:3 or having at least 80% identity to SEQ ID NO:3.

In one embodiment relating to the first aspect, the recombinant rhabdovirus is a vesiculovirus.

In one embodiment relating to the first aspect, the vesiculovirus is selected from the group comprising: vesicular stomatitis alagoas virus (VSAV), carajás virus (CJSV), chandipura virus (CHPV), cocal virus (COCV), vesicular stomatitis Indiana virus (VSIV), isfahan virus (ISFV), maraba virus (MARAV), vesicular stomatitis New Jersey virus (VSNJV), or piry virus (PIRYV), preferably a vesicular stomatitis Indiana virus (VSIV) or preferably a vesicular stomatitis New Jersey virus (VSNJV).

In one embodiment relating to the first aspect, the recombinant rhabdovirus is replication-competent.

In one embodiment relating to the first aspect, the CD80 extracellular domain is human CD80 extracellular domain.

In one embodiment relating to the first aspect, the recombinant rhabdovirus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of an arenavirus, and/or the glycoprotein G is replaced by the glycoprotein GP of an arenavirus. In a further preferred embodiment, the gene coding for the glycoprotein G is replaced by the gene coding for the glycoprotein GP of Dandenong virus or Mopeia virus, and/or the glycoprotein G is replaced by the glycoprotein GP of Dandenong virus or Mopeia virus. Even more preferred, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In a preferred embodiment relating to the first aspect, the invention provides a recombinant vesicular stomatitis virus encoding in its genome at least one CD80 extracellular domain Fc-fusion protein or a functional variant thereof, wherein the CD80 extracellular domain Fc-fusion protein comprises the extracellular domain of CD80 and further comprises the Fc domain of an IgG. In a related embodiment, the CD80 extracellular domain Fc-fusion protein is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3; and wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a second aspect, the present invention relates to a recombinant vesicular stomatitis virus, encoding in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the CD80 extracellular domain Fc-fusion protein comprises the extracellular domain of CD80 and further comprises the Fc domain of an IgG.

In one embodiment relating to the second aspect, the nucleoprotein (N) comprises an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7.

In one embodiment relating to the second aspect, the phosphoprotein (P) comprises an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8.

In one embodiment relating to the second aspect, the large protein (L) comprises an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9.

In one embodiment relating to the second aspect, the matrix protein (M) comprises an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a preferred embodiment relating to the second aspect, the nucleoprotein (N) comprises an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In one embodiment relating to the second aspect, the recombinant vesicular stomatitis virus is replication-competent.

In one embodiment relating to the second aspect, the recombinant vesicular stomatitis virus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In one embodiment relating to the second aspect, the CD80 extracellular domain Fc-fusion protein is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3.

In a preferred embodiment relating to the second aspect, the invention provides a recombinant vesicular stomatitis virus encoding in its genome a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the CD80 extracellular domain Fc-fusion protein comprises the extracellular domain of CD80 and further comprises the Fc domain of an IgG and is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3; and wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a third aspect, the present invention provides for a pharmaceutical composition, characterized in that the composition comprises a recombinant rhabdovirus according to the first aspect or any of its embodiments, or a recombinant vesicular stomatitis virus according the second aspect or any of its embodiments.

In a fourth aspect, the present invention provides for a recombinant rhabdovirus according to the first aspect or any of its embodiments, or a recombinant vesicular stomatitis virus according the second aspect or any of its embodiments, or a pharmaceutical composition according to the third aspect or any of its embodiments, for use as a medicament.

In one embodiment relating to the fourth aspect, the invention provides a recombinant rhabdovirus, a recombinant vesicular stomatitis virus, or a pharmaceutical composition for the use in the treatment of cancer, preferably solid cancers. In a preferred embodiment, the solid cancer is selected from the list comprising: reproductive tumor, an ovarian tumor, a pancreatic tumor, a testicular tumor, an endocrine tumor, a gastrointestinal tumor, a liver tumor, a kidney tumor, a colon tumor, a colorectal tumor, a bladder tumor, a prostate tumor, a skin tumor, melanoma, a respiratory tumor, a lung tumor, a breast tumor, a head & neck tumor, a head and neck squamous-cell carcinoma (HNSCC), and a bone tumor.

In one embodiment relating to the fourth aspect, the recombinant rhabdovirus, the recombinant vesicular stomatitis virus, or the pharmaceutical composition is to be administered intratumorally or intravenously. In another related embodiment, the recombinant rhabdovirus, the recombinant vesicular stomatitis virus or the pharmaceutical composition is to be administered at least once intratumorally and subsequently intravenously. In a further related embodiment, the subsequent intravenous administration of the recombinant rhabdovirus, recombinant vesicular stomatitis virus or the pharmaceutical composition is given 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

In a fifth aspect, the present invention provides for a composition comprising a recombinant rhabdovirus according to the first aspect or any of its embodiments, or a recombinant vesicular stomatitis virus according the second aspect or any of its embodiments and further an inhibitor, wherein the inhibitor is a PD-1 pathway inhibitor or a SMAC mimetic.

In one embodiment relating to the fifth aspect, the PD-1 pathway inhibitor is an antagonistic antibody, which is directed against PD-1 or PD-L1. In a further related embodiment, the SMAC mimetic is selected from the group consisting of any of compounds 1 to 26 from table 2 or a pharmaceutically acceptable salt of one of these compounds. In another related embodiment, the PD-1 pathway inhibitor is an antagonist selected from the group consisting of pembrolizumab, nivolumab, pidilizumab, atezolizumab, avelumab, durvalumab, PDR-001, PD1-1, PD1-2, PD1-3, PD1-4 and PD1-5 (as shown in Table 1). In a most preferred embodiment, the PD-1 pathway inhibitor is BI-754091.

In a sixth aspect, the present invention provides a kit of parts comprising: a recombinant rhabdovirus, a recombinant vesicular stomatitis virus or a pharmaceutical composition as defined in any of the first to third aspects or any of their embodiments, and a PD-1 pathway inhibitor or SMAC mimetic as defined in any of the embodiments relating to the fifth aspect.

In a seventh aspect, the present invention provides for a combination treatment comprising: a) a recombinant rhabdovirus according to the first aspect or any of its embodiments, or a recombinant vesicular stomatitis virus according the second aspect or any of its embodiments, or a pharmaceutical composition according to the third aspect or any of its embodiments, and b) a PD-1 pathway inhibitor or a SMAC mimetic. In one embodiment relating to the seventh aspect a) and b) may be administered concomitantly, sequentially or alternately. In a related embodiment, a) and b) are administered via different administration routes. In a further related embodiment, a) is administered intratumorally b) is administered intravenously.

In one embodiment relating to the seventh aspect, the PD-1 pathway inhibitor is an antagonistic antibody, which is directed against PD-1 or PD-L1. In a related embodiment the PD-1 pathway inhibitor is selected from the group consisting of pembrolizumab, nivolumab, pidilizumab, atezolizumab, avelumab, durvalumab, PDR-001, PD1-1, PD1-2, PD1-3, PD1-4 and PD1-5 (see Table 1). In a further related embodiment the SMAC mimetic is selected from the group consisting of any one of compounds 1 to 26 according to table 2 or a pharmaceutically acceptable salt of one of these compounds.

In an eight aspect, the invention provides for a virus producing cell, characterized in that the cell produces a recombinant rhabdovirus according to the first aspect or any of its embodiments, or a recombinant vesicular stomatitis virus according the second aspect or any of its embodiments.

In one embodiment relating to the eight aspect, the virus producing cell is a Vero cell, a HEK cell, a HEK293 cell, a Chinese hamster ovary cell (CHO), or a baby hamster kidney (BHK) cell.

In a ninth aspect, the invention provides for a method of producing a recombinant rhabdovirus in a cell culture:

(i) Infecting a host cell with a recombinant rhabdovirus, preferably a vesicular stomatitis virus, (ii) Culturing the host cell under conditions allowing replication of the recombinant rhabdovirus, (iii) Harvesting the recombinant rhabdovirus from the cell culture, (iv) Optionally, enzyme treatment of the virus harvest, preferably with benzonase, (v) Capturing the rhabdovirus harvest by loading on a cation exchange monolith membrane adsorber or resin followed by elution, (vi) Polish rhabdovirus by subjecting the eluate of step (v) to size exclusion, multi modal size exclusion/ion exchange or tangential flow filtration, (vii) Buffer change of polished rhabdovirus by ultrafiltration/diafiltration, (viii) Sterile filtration of rhabdovirus.

In one embodiment relating to the ninth aspect, the host cell is a HEK293 cell.

In one embodiment relating to the ninth aspect, the host cell is cultured in suspension.

In one embodiment relating to the ninth aspect, the recombinant rhabdovirus is formulated into a pharmaceutical composition. In a preferred embodiment, the recombinant rhabdovirus according to the first aspect or any of its embodiments, or a recombinant vesicular stomatitis virus according the second aspect or any of its embodiments is formulated into a pharmaceutical composition.

BRIEF DESCRIPTION OF THE DRAWINGS

FIG. 3A-B Replication (A) and Viability (B) of VSV-GP-CD80-Fc relative to the parental virus VSV-GP were compared. HEK293F cells were infected with either VSV-GP or VSV-GP-CD80-Fc. Y-axis shows cell viability in percent or genome copies per ml. Both cell viability and replication were monitored for up to 48 h after infection (x-axis: hours post infection).

FIG. 5A-B In vivo efficacy (A) and body weight development (B) of mice treated with VSV-GP-CD80-Fc compared to the parental virus VSV-GP using the CT26. CL25-IFNARKO tumor model (i.v.). (A) Mice were treated on day 0 & 3 with a low viral dose of $2\times10^7$ $TCID_{50}$. X-axis shows the time (in days) and y-axis the percentage of mice that survived. (B) Body weight development of the same treated mice as in FIG. 6A is shown. X-axis shows the time (in days) and y-axis the body weight (in g)

FIG. 6A-C In vivo efficacy of VSV-GP-CD80-Fc compared to the parental virus VSV-GP in treated mice using the B16-F1-OVA tumor model (i.t.) with treatments on day 0 & 3 with a viral dose of $10^8$ $TCID_{50}$ VSV-GP (B), the same viral dose of VSV-GP-CD80-Fc (C) or PBS (A). X-axis shows the days post treatment (in days) and y-axis the tumor volume (in $cm^3$).

FIG. 7A-B In vivo efficacy of VSV-GP-CD80-Fc in treated mice (B) compared to the parental virus VSV-GP (A) using the EMT-6 tumor model (i.t.) and treatments on day 0 & 3 with a low viral dose of $2\times10^7$ $TCID_{50}$. X-axis shows the days post treatment (in days) and y-axis the tumor volume (in $cm^3$). Dotted line represents mice treated with vehicle and solid line mice treated with virus.

FIG. 13A-D Human Mixed-Leukocyte culture (T-cells and monocytes from two genetically different individuals are co-cultured), stimulated with recombinant CD80-Fc protein (10 μg/ml) and with or without the addition of FcγR-block (and in the absence of human serum), using IFNγ secretion as readout. The different sub-figures (A-D) depict different donor pairs.

FIG. 14A-F Human PBMC cultures were stimulated with or without low doses of anti-CD3 and increasing concentrations of recombinant CD80-Fc protein (F(ab)2 (A, D), Fc=IgG4 (B, E) or Fc=IgG1 (C, F)), measuring IFNγ (A-C) or IL2 (D-F) secretion as readouts, which were detected by standard ELISA of the supernatants.

FIG. 16A-C Improved induction of tumor-specific T-cells by VSV-GP-mCD80-Fc vs. VSV-GP was determined in CT26. CL25-IFNARKO tumor bearing mice using ELISPOT and tetramer staining. gp70-specific α-Tumor-T-cells are increased in the Spleen of VSV-GP-mCD80-Fc vs. VSV-GP treated mice. Open symbols represent i.v. treatments. Closed symbols represent i.v./i.t. treatments. (A) Detection of gp70-specific T-cells from spleens by ELISPOT or (B) from blood by Dextramers. (C) Experimental outline.

FIG. 18A-B Reporter Cell Assay: Jurkat-PD1 (luciferase reporter cells) in co-culture with THP-1-PDL1 cells (express FcγRs). T-cell activation is triggered by a CD33×CD3 BiTE (10 nM) in this system. (A) Treatment with the indicated reagents (anti-PD1=Pembrolizumab; anti-Dig=isotype control & recombinant CD80-Fc) at the indicated concentrations. (B) Anti-PD1 (10 nM) and increasing concentrations of recombinant CD80-Fc improve Jurkat T-cell activation beyond the activity of the individual compounds.

FIG. 19A-C In vivo efficacy (A), tumor growth curves (B) and body weight change (C) of mice treated with VSV-GP-muCD80-Fc, the parental virus VSV-GP, and recombinant murine CD80-Fc using the CT26. CL25-IFNARKO tumor model (i.v.). (A) Mice were treated on day 0 & 3 with a viral dose of $1\times10^8$ $TCID_{50}$ and on day 0, 3 and 6 with 1 mg/kg recombinant murine CD80-Fc, respectively. The x-axis shows the time (in days) and the y-axis the percentage of mice that survived. (B) Mean tumor volumes over time of the same treated mice as in FIG. 19A is shown. The x-axis shows the time (in days after start of treatment) and the y-axis the tumor volume (in $mm^3$). Data show the group mean with last observation carried forward until 70% of group size was reached (70% LOCF). (C) Body weight change of the same treated mice as in FIG. 19A is shown. The x-axis shows the time (in days after start of treatment) and the y-axis the body weight change compared to initial body weight at treatment start (in %).

DETAILED DESCRIPTION OF THE INVENTION

Figure 1:
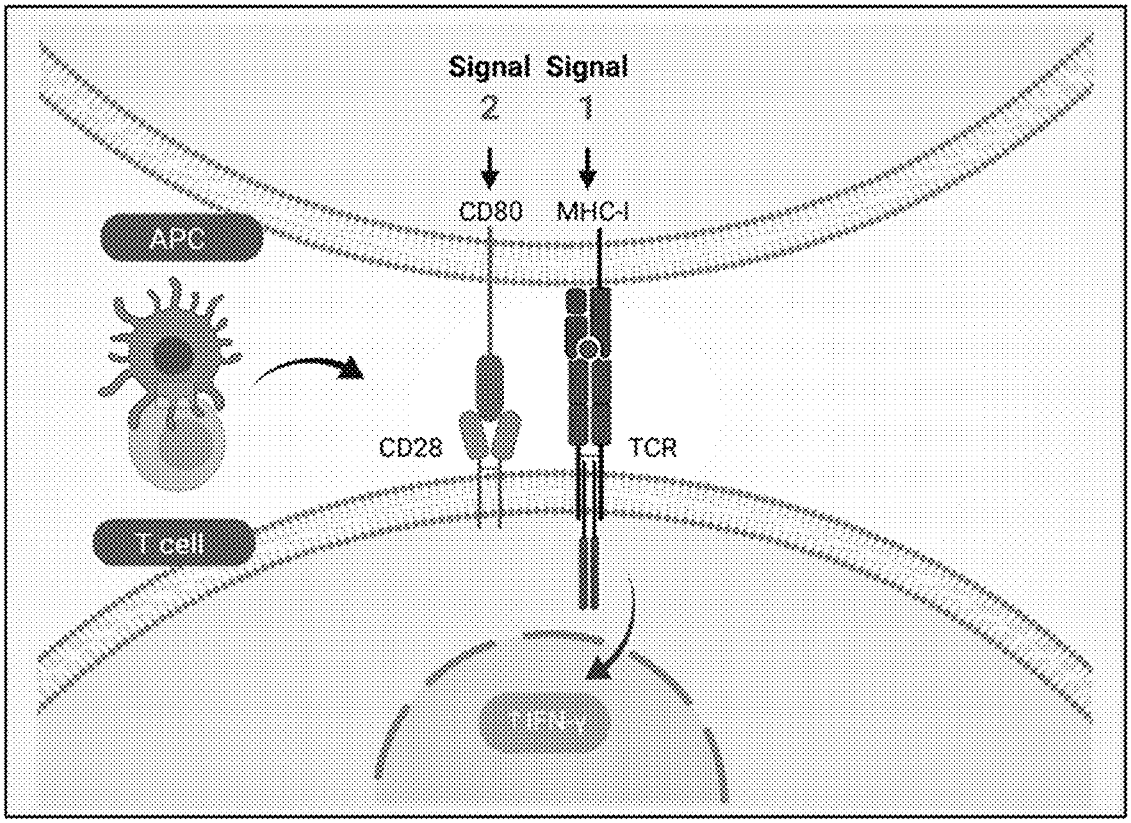
FIG. 1: A schematic representation of an immunological synapse and components between an Antigen Presenting Cell (APC) and a T-cell. CD80 is a key co-stimulatory molecule during T-cell activation. Efficient T-cell stimulation requires two converging molecular signals within the immunological synapse. Signal 1: Antigen-specific (TCR: MHC/Peptide) and Signal 2. Antigen-independent (CD28: CD80).
Figure 2:
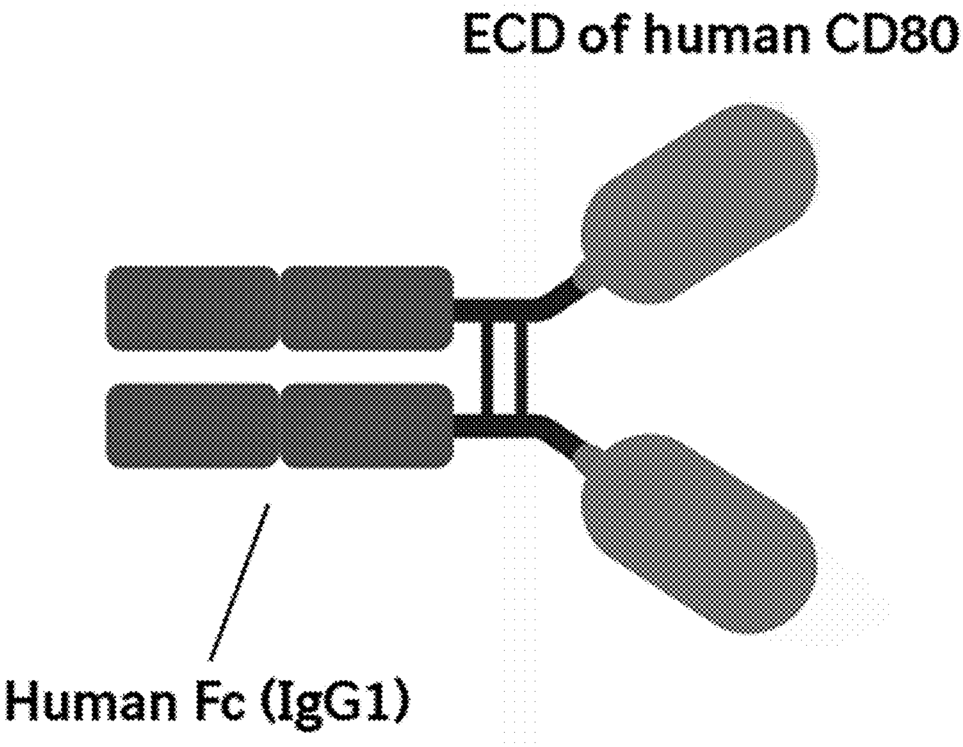
FIG. 2: Cartoon of CD80 extracellular domain (ECD) Fc-fusion protein (bivalent). The fusion protein is expressed in the transduced tumor cells following viral infection. The two CD80 extracellular domain Fc-fusion monomers are covalently linked together by disulfide bonds formed between cysteine residues in each monomer, thereby forming the CD80 extracellular domain Fc-fusion protein dimer.
Figure 4:
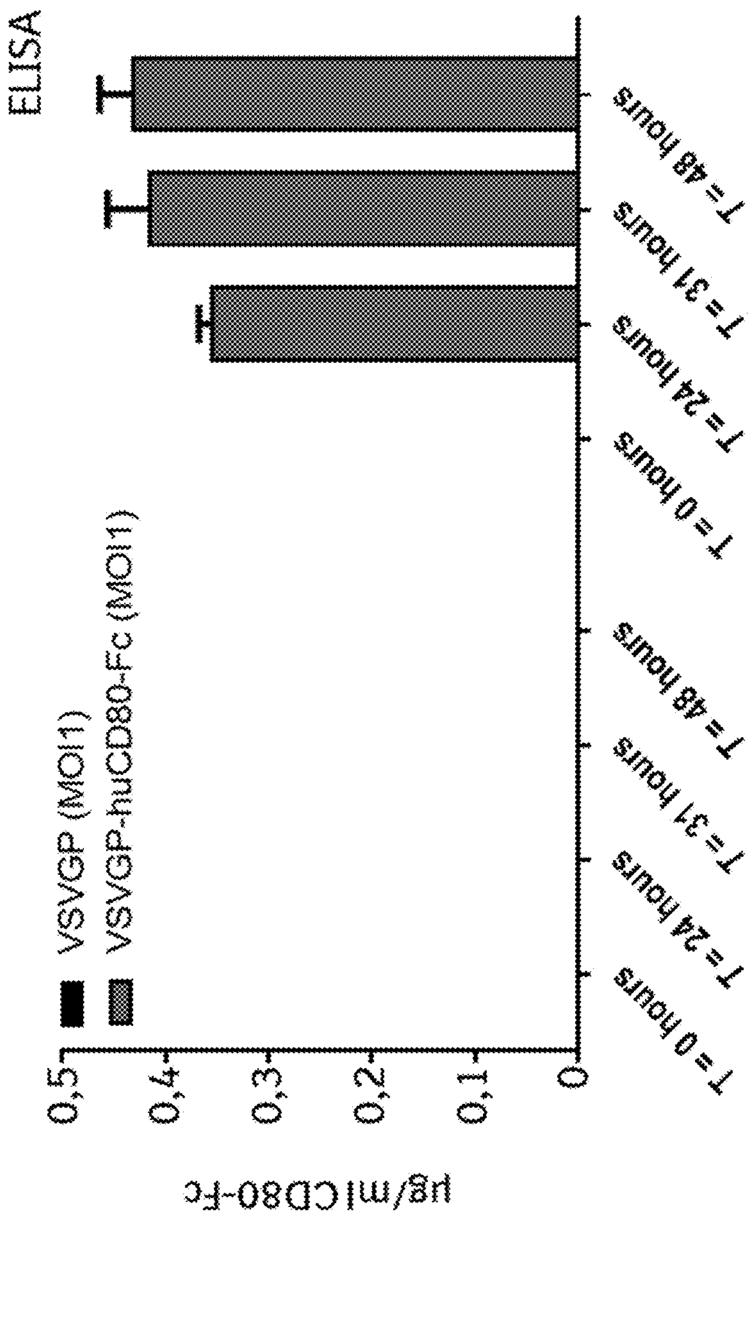
FIG. 4 Soluble CD80-Fc detection by ELISA in tissue culture supernatants from HEK293 cells infected with VSV-GP or VSV-GP-CD80-Fc each with a multiplicity of infection of 1 (MOI 1). CD80-Fc expression (y-axis in μg/ml) was determined for different time points after infection for up to 48 hours (x-axis).

In the following detailed description, numerous specific details are set forth to provide a full understanding of the present invention. It will be apparent, however, to one ordinarily skilled in the art that the subject technology may be practiced without some of these specific details. In other instances, well-known structures and techniques have not been shown in detail so as not to obscure the present invention. The headings are included merely for convenience to assist in reading and shall not be understood to limit the invention to specific aspects or embodiments.

Rhabdoviruses

The family of rhabdoviruses includes 18 genera and 134 species with negative-sense, single-stranded RNA genomes of approximately 10-16 kb (Walke et al., ICTV Virus Taxonomy Profile: Rhabdoviridae, Journal of General Virology, 99:447-448 (2018)).

Characterizing features of members of the family of rhabdoviruses include one or more of the following: A bullet-shaped or bacilliform particle 100-430 nm in length and 45-100 nm in diameter comprised of a helical nucleocapsid surrounded by a matrix layer and a lipid envelope, wherein some rhabdoviruses have non-enveloped filamentous viruses. A negative-sense, single-stranded RNA of 10.8-16.1 kb, which are mostly unsegmented. A genome encoding for at least 5 genes encoding the structural proteins nucleoprotein (N), large protein (L), phosphoprotein (P), matrix protein (M), and glycoprotein (G).

As used herein a rhabdovirus can belong to the genus of: almendravirus, curiovirus, cytorhabdovirus, dichorhavirus, ephemerovirus, Hapavirus, ledantevirus, lyssavirus, novirhabdovirus, nucleorhabdovirus, perhabdovirus, sigmavirus, sprivivirus, sripuvirus, tibrovirus, tupavirus, varicosavirus or vesiculovirus.

Within the genus mentioned herein the rhabdovirus can belong to any of the listed species. The genus of almendravirus includes: arboretum almendravirus, balsa almendravirus, Coot Bay almendravirus, Puerto Almendras almendravirus, Rio Chico almendravirus; the genus of curiovirus includes: curionopolis curiovirus, Iriri curiovirus, Itacaiunas curiovirus, Rochambeau curiovirus; the genus of cythorhabdovirus includes: Alfalfa dwarf cytorhabdovirus, Barley yellow striate mosaic cytorhabdovirus, Broccoli necrotic yellows cytorhabdovirus, Colocasia bobone disease-associated cytorhabdovirus, Festuca leaf streak cytorhabdovirus, Lettuce necrotic yellows cytorhabdovirus, Lettuce yellow mottle cytorhabdovirus, Northern cereal mosaic cytorhabdovirus, Sonchus cytorhabdovirus 1, Strawberry crinkle cytorhabdovirus, Wheat American striate mosaic cytorhabdovirus; the genus of dichorhavirus includes: Coffee ringspot dichorhavirus, Orchid fleck dichorhavirus; the genus of ephemerovirus includes: Adelaide River ephemerovirus, Berrimah ephemerovirus, Bovine fever ephemerovirus, Kimberley ephemerovirus, Koolpinyah ephemerovirus, Kotonkan ephemerovirus, Obodhiang ephemerovirus, Yata ephemerovirus; the genus of hapavirus includes: Flanders hapavirus, Gray Lodge hapavirus, Hart Park hapavirus, Joinjakaka hapavirus, Kamese hapavirus, La Joya hapavirus, Landjia hapavirus, Manitoba hapavirus, Marco hapavirus, Mosqueiro hapavirus, Mossuril hapavirus, Ngaingan hapavirus, Ord River hapavirus, Parry Creek hapavirus, Wongabel hapavirus; the genus of ledantevirus includes: Barur ledantevirus, Fikirini ledantevirus, Fukuoka ledantevirus, Kanyawara ledantevirus, Kern Canyon ledantevirus, Keuraliba ledantevirus, Kolente ledantevirus, Kumasi ledantevirus, Le Dantec ledantevirus, Mount Elgon bat ledantevirus, Nishimuro ledantevirus, Nkolbisson ledantevirus, Oita ledantevirus, Wuhan ledantevirus, Yongjia ledantevirus; the genus of lyssavirus includes: Aravan lyssavirus, Australian bat lyssavirus, Bokeloh bat lyssavirus, Duvenhage lyssavirus, European bat 1 lyssavirus, European bat 2 lyssavirus, Gannoruwa bat lyssavirus, Ikoma lyssavirus, Irkut lyssavirus, Khujand lyssavirus, Lagos bat lyssavirus, Lleida bat lyssavirus, Mokola lyssavirus, Rabies lyssavirus, Shimoni bat lyssavirus, West Caucasian bat lyssavirus; the genus of novirhabdovirus includes: Hirame novirhabdovirus, Piscine novirhabdovirus, Salmonid novirhabdovirus, Snakehead novirhabdovirus; the genus of nucleorhabdovirus includes: Datura yellow vein nucleorhabdovirus, Eggplant mottled dwarf nucleorhabdovirus, Maize fine streak nucleorhabdovirus, Maize Iranian mosaic nucleorhabdovirus, Maize mosaic nucleorhabdovirus, Potato yellow dwarf nucleorhabdovirus, Rice yellow stunt nucleorhabdovirus, Sonchus yellow net nucleorhabdovirus, Sowthistle yellow vein nucleorhabdovirus, Taro vein chlorosis nucleorhabdovirus; the genus of perhabdovirus includes: Anguillid perhabdovirus, Perch perhabdovirus, Sea trout perhabdovirus; the genus of sigmavirus includes: *Drosophila affinis* sigmavirus, *Drosophila ananassae* sigmavirus, *Drosophila immigrans* sigmavirus, *Drosophila melanogaster* sigmavirus, *Drosophila obscura* sigmavirus, *Drosophila tristis* sigmavirus, *Muscina stabulans* sigmavirus; the genus of sprivivirus includes: Carp sprivivirus, Pike fry sprivivirus; the genus of Sripuvirus includes: Almpiwar sripuvirus, Chaco sripuvirus, Niakha sripuvirus, Sena Madureira sripuvirus, Sripur sripuvirus; the genus of tibrovirus includes: Bas-Congo tibrovirus, Beatrice Hill tibrovirus, Coastal Plains tibrovirus, Ekpoma 1 tibrovirus, Ekpoma 2 tibrovirus, Sweetwater Branch tibrovirus, tibrogargan tibrovirus; the genus of tupavirus includes: Durham tupavirus, Klamath tupavirus, Tupaia tupavirus; the genus of varicosavirus includes: Lettuce big-vein associated varicosavirus; the genus of vesiculovirus includes: Alagoas vesiculovirus, American bat vesiculovirus, Carajas vesiculovirus, Chandipura vesiculovirus, Cocal vesiculovirus, Indiana vesiculovirus, Isfahan vesiculovirus, Jurona vesiculovirus, Malpais Spring vesiculovirus, Maraba vesiculovirus, Morreton vesiculovirus, New Jersey vesiculovirus, Perinet vesiculovirus, Piry vesiculovirus, Radi vesiculovirus, Yug Bogdanovac vesiculovirus, or Moussa virus.

Preferably, the recombinant rhabdovirus of the invention is an oncolytic rhabdovirus. In this respect, oncolytic has its regular meaning known in the art and refers to the ability of a rhabdovirus to infect and lyse (break down) cancer cells but not normal cells (to any significant extend). Preferably, the oncolytic rhabdovirus is capable of replication within cancer cells. Oncolytic activity may be tested in different assay systems known to the skilled artisan (an exemplary in vitro assay is described by Muik et al., Cancer Res., 74(13), 3567-78, 2014). It is to be understood that an oncolytic rhabdovirus may infect and lyse only specific types of cancer cells. Also, the oncolytic effect may vary depending on the type of cancer cells.

In a preferred embodiment, the rhabdovirus belongs to the genus of vesiculovirus. Vesiculovirus species have been defined primarily by serological means coupled with phylogenetic analysis of the genomes. Biological characteristics such as host range and mechanisms of transmission are also used to distinguish viral species within the genus. As such, the genus of vesiculovirus form a distinct monophyletic group well-supported by Maximum Likelihood trees inferred from complete L sequences.

Viruses assigned to different species within the genus vesiculovirus may have one or more of the following characteristics: A) a minimum amino acid sequence divergence of 20% in L; B) a minimum amino acid sequence divergence of 10% in N; C) a minimum amino acid sequence divergence of 15% in G; D) can be distinguished in serological tests; and E) occupy different ecological niches as evidenced by differences in hosts and or arthropod vectors.

Preferred is the vesicular stomatitis virus (VSV) and in particular the VSV-GP (recombinant with GP of LCMV). Advantageous properties of the VSV-GP include one or more of the following: very potent and fast killer (<8 h); oncolytic virus; systemic application possible; reduced neurotropism/neurotoxicity; it reproduces lytically and induces immunogenic cell death; does not replicate in healthy human cells, due to interferon (IFN) response; strong activation of innate immunity; about 3 kb space for immunomodulatory cargos and antigens; recombinant with an arenavirus glycoprotein from the Lympho-Chorio-Meningitis-Virus (LCMV); favorable safety features in terms of reduced neurotoxicity and less sensitive to neutralizing antibody responses and complement destruction as compared to the wild type VSV (VSV-G); specifically replicates in tumor cells, which have lost the ability to mount and respond to anti-viral innate immune responses (e.g. type-I IFN signaling); abortive replication in "healthy cells" so is rapidly excluded from normal tissues; viral replication in tumor cells leads to the induction of immunogenic cell death, release of tumor associated antigens, local inflammation and the induction of anti-tumor immunity.

The invention is further embodied by a recombinant vesicular stomatitis virus, encoding in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, preferably comprising the human CD80 extracellular domain.

In a preferred embodiment the recombinant vesicular stomatitis virus encodes in its genome at least for a vesicular stomatitis virus nucleoprotein (N) comprising an amino acid sequence as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, a phosphoprotein (P) comprising an amino acid sequence as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, a large protein (L) comprising an amino acid sequence as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and a matrix protein (M) comprising an amino acid sequence as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

It is understood by the skilled artisan that modifications to the vesicular stomatitis virus nucleoprotein (N), large protein (L), phosphoprotein (P), matrix protein (M), or glycoprotein (G) sequence can be made without losing the basic functions of those proteins. Such functional variants as used herein retain all or part of their basic function or activity. The protein L for example is the polymerase and has an essential function during transcription and replication of the virus. A functional variant thereof must retain at least part of this ability. A good indication for retention of basic functionality or activity is the successful production of viruses, including these functional variants, that are still capable to replicate and infect tumor cells. Production of viruses and testing for infection and replication in tumor cells may be tested in different assay systems known to the skilled artisan (an exemplary in vitro assay is described by Muik et al., Cancer Res., 74(13), 3567-78, 2014).

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the large protein (L) comprises an amino acid sequence having a sequence identity≥80% of SEQ ID NO:9.

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the nucleoprotein (N) comprises an amino acid sequence having a sequence identity≥90% of SEQ ID NO:7.

In a further preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CD80 extracellular domain Fc-fusion protein or a functional variant thereof, wherein the large protein (L) comprises an amino acid sequence having a sequence identity equal or greater 80% of SEQ ID NO:9 and the nucleoprotein (N) comprises an amino acid sequence having a sequence identity≥90% of SEQ ID NO:7.

In a preferred embodiment of the invention the RNA genome of the recombinant rhabdovirus of the invention comprises or consists of a sequence as shown in SEQ ID NO: 24. Furthermore, the RNA genome of the recombinant rhabdovirus of the invention may also consist of or comprise those sequences, wherein nucleic acids of the RNA genome are exchanged according to the degeneration of the genetic code, without leading to an alteration of respective amino acid sequence. In a further preferred embodiment, the RNA genome of the recombinant rhabdovirus of the invention comprises or consists of a coding sequence identical or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

It is to be understood that a recombinant rhabdovirus of the invention may encode in its genome further cargos, such as tumor antigens, further chemokines, cytokines or other immunomodulatory elements.

In a further embodiment the recombinant rhabdovirus of the invention additionally encodes in its genome a sodium iodide symporter protein (NIS). Expression of NIS and co-incubation with e.g. $^{125}I$ allows the use of NIS as imaging reporter (Carlson et al., Current Gene Therapy, 12, 33-47, 2012).

Recombinant Rhabdovirus

It is known that certain wildtype rhabdovirus strains such as wildtype VSV strains are considered to be neurotoxic. It is also reported that infected individuals are able to rapidly mount a strong humoral response with high antibody titers directed mainly against the glycoprotein. Neutralizing antibodies targeting the glycoprotein G of rhabdoviruses in general and VSV specifically are able to limit virus spread and thereby mediate protection of individuals from virus re-infection. Virus neutralization, however, limits repeated application of the rhabdovirus to the cancer patient.

To eliminate these drawbacks the rhabdovirus wildtype glycoprotein G may be replaced with the glycoprotein from another virus. In this respect replacing the glycoprotein refers to (i) replacement of the gene coding for the wild type glycoprotein G with the gene coding for the glycoprotein GP of another virus, and/or (ii) replacement of the wild type glycoprotein G with the glycoprotein GP of another virus.

In a preferred embodiment the rhabdovirus glycoprotein G is replaced with the glycoprotein GP of the lymphocytic choriomeningitis virus (LCMV), preferably with the strain WE-HPI. In an even more preferred embodiment, the rhabdovirus is a vesicular stomatitis virus with the glycoprotein GP of the lymphocytic choriomeningitis virus (LCMV), preferably with the strain WE-HPI. Such VSV is for example described in WO2010/040526 and named VSV-GP. Advantages offered are (i) the loss of VSV-G mediated neurotoxicity and (ii) a lack of vector neutralization by antibodies (as shown in mice).

The glycoprotein GP of the lymphocytic choriomeningitis virus (LCMV) may be GP1 or GP2. The invention includes glycoproteins from different LCMV strains. In particular, LCMV-GP can be derived from LCMV wild-type or LCMV strains LCMV-WE, LCMV-WE-HPI, LCMV-WE-HPI opt. In a preferred embodiment, the gene coding for the glycoprotein GP of the LCMV encodes for a protein with an amino acid sequence as shown in SEQ ID NO:11 or an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:11 while the functional properties of the recombinant rhabdovirus comprising a glycoprotein GP encoding an amino acid sequence as shown in SEQ ID NO:11 are maintained.

In another embodiment the recombinant rhabdovirus glycoprotein G is replaced with the glycoprotein GP of the Dandenong virus (DANDV) or Mopeia (MOPV) virus. In a more preferred embodiment, the recombinant rhabdovirus is a vesicular stomatitis virus wherein the glycoprotein G is replaced with the glycoprotein GP of the Dandenong virus (DANDV) or Mopeia (MOPV) virus. Advantages offered are (i) the loss of VSV-G mediated neurotoxicity and (ii) a lack of vector neutralization by antibodies (as shown in mice).

The Dandenong virus (DANDV) is an old world arenavirus. To date, there is only a single strain known to the person skilled in the art, which comprise a glycoprotein GP and which may be employed within the present invention as donor of the glycoprotein GP comprised in the recombinant rhabdovirus of the invention. The DANDV glycoprotein GP comprised in the recombinant rhabdovirus of the invention has more than 6 glycosylation sites, in particular 7 glycosylation sites. An exemplary preferred glycoprotein GP is that as comprised in DANDV as accessible under Genbank number EU136038. In one embodiment, the gene coding for the glycoprotein GP of the DANDV encodes for an amino acid sequence as shown in SEQ ID NO:12 or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:12 while the functional properties of the recombinant rhabdovirus comprising a glycoprotein GP encoding an amino acid sequence as shown in SEQ ID NO:12 are maintained.

The Mopeia virus (MOPV) is an old world arenavirus. There are several strains known to the person skilled in the art, which comprise a glycoprotein GP and which may be employed within the present invention as donor of the glycoprotein GP comprised in the recombinant rhabdovirus of the invention. The MOPV glycoprotein GP comprised in the recombinant rhabdovirus of the invention has more than 6 glycosylation sites, in particular 7 glycosylation sites. An exemplary preferred glycoprotein GP is that as comprised in Mopeia virus as accessible under Genbank number AY772170. In one embodiment, the gene coding for glycoprotein GP of the MOPV encodes for an amino acid sequence as shown in SEQ ID NO:13 or a sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:13 while the functional properties of the recombinant rhabdovirus comprising a glycoprotein GP encoding an amino acid sequence as shown in SEQ ID NO:13 are maintained.

CD80 Extracellular Domain Fc-Fusion Protein

CD80, also known as B7-1, is a 60 kD single chain type I glycoprotein belonging to the immunoglobulin superfamily. CD80 is expressed on activated/mature antigen-presenting cells, such as dendritic cells. CD80 binds to CD28 and CD152 (CTLA-4). Along with CD86 (B7-2), CD80 plays a critical role in the regulation of T-cell activation. The interaction of CD80 with CD28 provides a co-stimulatory signal for T-cell activation in the complex of TCR engagement. Its interaction with CTLA-4 (e.g. expressed on regulatory T-cells), which has a higher affinity for CD80 than CD28 and acts as a decoy receptor for CD80, rather than functioning as a suppressive signaling receptor, deprives T-cells of the crucial co-stimulatory CD28 signal.

In the past it was proposed that oncolytic viruses and in particular VSV-GP can induce tumor cell lysis combined with immunogenic cell death and stimulation of innate immune cells in the tumor microenvironment. It was further proposed that immune modulatory proteins may be encoded into the genome of oncolytic viruses and that the expression of said immune modulatory proteins may support the oncolytic effect of the virus by local immune stimulating activities.

One of the challenges of expressing immune-promoting molecules from a viral backbone, such as chemokines and/or cytokines, is that not only potentiation of anti-tumor immunity must be achieved but at the same time an anti-viral immunity response by the immune-promoting molecule is to be avoided. Care has to be taken that the additional immune-promoting molecule does not restrict the oncolytic potential of the virus to a degree where the potential benefit gained by expression of the therapeutic cargo is overruled by the loss of oncolytic potency.

The inventors hypothesized that a CD80 extracellular domain Fc-fusion protein on the one side may provide efficient T-cell co-stimulation in the context of T-cell receptor engagement and on the other side would not activate natural killer cells (activated by e.g. IL2, IL15, CD137), which would limit viral replication and/or persistence at an early stage. The CD80 extracellular domain Fc-fusion protein is a potent co-stimulatory molecule, active in priming and re-activation of antigen-specific T-cells. This stimulus is crucial as T-cell co-stimulatory signals are often underrepresented in tumors, leading to clonal T-cell anergy, loss of effector function and T-cell death.

By providing a recombinant rhabdovirus according to the invention tumor-restricted replication of a CD80 extracellular domain Fc-fusion protein may lead to the local expression of the T-cell co-stimulating fusion protein, which further enhances anti-tumor T-cell immunity by providing activating signals to T-cells in the context of T-cell receptor engagement (e.g. tumor cell recognition) in an FcγR-dependent manner.

The inventors surprisingly found that a recombinant rhabdovirus according to the invention encoding for a CD80 extracellular domain Fc-fusion protein was able to induce tumor cell lysis combined with immunogenic cell death and stimulation of innate immune cells in the tumor microenvironment. Further, prolonged survival rates were observed in an established mouse tumor model treated with such a recombinant rhabdovirus armed with a CD80 extracellular domain Fc-fusion protein.

Unexpectedly, infection with the recombinant rhabdovirus according to the invention encoding for a CD80 extracellular domain Fc-fusion protein lead to a strong increase of FcγR expression within the infected tumors. It was shown by the inventors that optimal biological activity of the CD80 extracellular domain Fc-fusion protein is strongly dependent on the FcγR.

Without wishing to be bound by theory, it is believed that the strong anti-tumoral effects obtained by the recombinant rhabdovirus according to the invention encoding for a CD80 extracellular domain Fc-fusion protein is based at least in part on the FcγR-dependent activity of the CD80 extracellular domain Fc-fusion protein, which activity is potentiated by the increased expression of FcγRs in infected tumors after infection with recombinant rhabdovirus according to the invention.

Alternatively, in this context provision of a CD86 (B7-2) fusion protein is also contemplated, i.e. a recombinant rhabdovirus encoding for a CD86 extracellular domain Fc-fusion protein and in particular a VSV-GP encoding for a CD86 extracellular domain Fc-fusion protein, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

A "CD80 extracellular domain Fc-fusion protein" as used herein refers to a fusion protein or a functional variant thereof comprising or consisting of a CD80 extracellular domain which is fused to the Fc domain of an IgG.

The "CD80 extracellular domain" comprises or consists of naturally occurring polypeptides, such as different isoforms, as well as functional variants thereof, preferably the human CD80 extracellular domain.

In one aspect, the recombinant rhabdovirus encoding in its genome at least one CD80 extracellular domain Fc-fusion protein or a functional variant thereof is able to enhance recruitment of T-cells and dendritic cells to the tumor environment.

In another aspect, expression of the at least one CD80 extracellular domain Fc-fusion protein or a functional variant thereof from the genome of the recombinant rhabdovirus provides a therapeutic option for patients with cold tumors and a low mutational burden to boost the T-cell mediated anti-tumor T-cell response against poorly immunogenic tumors.

In another aspect, expression of the at least one CD80 extracellular domain Fc-fusion protein or a functional variant thereof from the genome of the recombinant rhabdovirus does not induce additional natural killer cells (beyond the effects of the parental VSV-GP virus) and selectively activates antigen-specific T-cells.

In another aspect, expression of the at least one CD80 extracellular domain Fc-fusion protein or a functional variant thereof from the genome of the recombinant rhabdovirus does not induce superagonism.

In another aspect, expression of the at least one CD80 extracellular domain Fc-fusion protein or a functional variant thereof from the genome of the recombinant rhabdovirus does not increase early anti-viral immunity to the recombinant rhabdovirus.

In yet another aspect, in addition to local expression in the tumor due to its solubility the CD80 extracellular domain Fc-fusion protein may also reach tumor-draining lymphatics (e.g. lymph nodes).

Human CD80 protein (UniProtKB-P33681|CD80_HUMAN T-lymphocyte activation antigen CD80) comprises or consists of 288 amino acids total and contains a signal peptide, an extracellular domain and a transmembrane/topological domain:

(SEQ ID NO: 6)

```
MGHTRRQGTSPSKCPYLNFFQLLVLAGLSHFCSGVIHVTKEVKEVATLSC
GHNVSVEELAQTRIYWQKEKKMVLTMMSGDMNIWPEYKNRTIFDITNNLS
IVILALRPSDEGTYECVVLKYEKDAFKREHLAEVTLSVKADFPTPSISDF
EIPTSNIRRIICSTSGGFPEPHLSWLENGEELNAINTTVSQDPETELYAV
SSKLDFNMTTNHSFMCLIKYGHLRVNQTFNWNTTKQEHFPDNLLPSWAIT
LISVNGIFVICCLTYCFAPRCRERRRNERLRRESVRPV.
```

In one embodiment, the CD80 extracellular domain of the CD80 extracellular domain Fc-fusion protein comprises or consists of amino acids 1-242 of SEQ ID NO:6 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-242 of SEQ ID NO:6.

In another embodiment the CD80 extracellular domain of the CD80 extracellular domain Fc-fusion protein comprises or consists of the following sequence:

(SEQ ID NO: 1)

```
VIHVTKEVKEVATLSCGHNVSVEELAQTRIYWQKEKKMVLTMMSGDMNIW
PEYKNRTIFDITNNLSIVILALRPSDEGTYECVVLKYEKDAFKREHLAEV
TLSVKADFPTPSISDFEIPTSNIRRIICSTSGGFPEPHLSWLENGEELNA
INTTVSQDPETELYAVSSKLDFNMTTNHSFMCLIKYGHLRVNQTFNWNTT
KQEHFPDN
```

or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1.

In one embodiment, the CD80 extracellular domain Fc-fusion protein comprises a signal peptide sequence. In another embodiment, the CD80 extracellular domain Fc-fusion does not comprise a signal peptide sequence.

The term "signal peptide" or "signal peptide sequence" describes a peptide sequence usually 10 to 30 amino acids in length and present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular, the signal peptide may be capable of directing the polypeptide into a cell's secretory pathway.

It is to be understood that for the present invention other (i.e., other than the wild-type) signal peptide sequences may be used together with the CD80 extracellular domain Fc-fusion protein. Such other signal peptide sequences may replace the original wild-type signal peptide sequence. A signal peptide includes peptides that direct newly synthesized protein in the ribosome to the ER and further to the Golgi complex for transport to the plasma membrane or out of the cell. They generally include a string of hydrophobic amino acids and include immunoglobulin leader sequences as well as others known to those skilled in the art. Signal peptides include in particular peptides capable of being acted upon by signal peptidase, a specific protease located on the cisternal face of the endoplasmic reticulum. Signal peptides are well understood by those of skill in the art and may include any known signal peptide. The signal peptide is incorporated at the N-terminus of the protein and processing of the CD80 extracellular domain Fc-fusion protein by signal peptidase produces the active biological form.

In one embodiment, the CD80 extracellular domain Fc-fusion protein comprises the wild-type CD80 signal peptide sequence. In a preferred embodiment, the CD80 extracellular domain Fc-fusion protein comprises the wild-type human CD80 signal peptide sequence which is amino acids 1-34 of SEQ ID NO:6 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-34 of SEQ ID NO:6.

In another embodiment, the CD80 extracellular domain Fc-fusion protein comprises a signal peptide sequence having the following sequence:

```
                                    (SEQ ID NO: 5)
MGWSCIILFLVATATGVHS
```

or a signal peptide sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5.

In a related embodiment the CD80 extracellular domain of the CD80 extracellular domain Fc-fusion protein comprises or consists of SEQ ID NO:1 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1 and further comprises a signal peptide sequence according to SEQ ID NO:5 or a signal peptide sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5

A CD80 extracellular domain Fc-fusion protein may also include a fusion protein with a truncated signal peptide sequence. In this context truncated refers to a signal peptide sequence that is shorter than the original signal peptide sequence but still retains at least a portion of its functionality to act as a signal peptide. For example, the human CD80 signal peptide sequence comprises or consists of amino acids 1-34 of SEQ ID NO:6. A CD80 extracellular domain Fc-fusion protein with a truncated signal peptide sequence could have 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 of the amino acids 1-34 of SEQ ID NO:6. In a further example, the signal peptide could comprise or consist of the sequence as shown in SEQ ID NO:5. A CD80 extracellular domain Fc-fusion protein with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:5.

A CD80 extracellular domain Fc-fusion protein with a truncated signal peptide sequence could also be a protein comprising SEQ ID No: 1 or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1 and in addition a signal peptide sequence that is shorter than the original signal peptide sequence. Again, by way of example signal peptide sequence could have 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 of the amino acids 1-34 of SEQ ID NO:6 or in a further example, the signal peptide could comprise or consist of the sequence as shown in SEQ ID NO:5. A CD80 extracellular domain Fc-fusion protein with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:5.

The CD80 extracellular domain can be of any origin including from mouse and rat. Preferably, the CD80 extracellular domain protein is from human origin.

The Fc domain of an IgG may be fused covalently to the N- or C-terminal part of the CD80 extracellular domain or at an internal position. In some embodiments, the Fc domain of an IgG molecule may be fused to the CD80 extracellular domain through a linker peptide, such as a GS linker. Preferably, the Fc domain is fused to the C-terminal part of the CD80 extracellular domain.

In some embodiments, the Fc domain has a wild-type sequence. In other embodiments, the Fc domain is either a natural or engineered variant. In some embodiments, the Fc domain comprises one or more mutations, substitutions and/or deletions compared to its wild-type sequence. In some embodiments, an Fc domain is chosen that has altered interactions of the Fc with one or more Fc gamma receptors (FcγRI, FcγRIIA, FcγRIIB, FcγRIIIA, FcγRIIIB). Preferably, the Fc domain is derived from a human IgG such as IgG1, IgG2, IgG3 or IgG4. More preferably, the Fc domain is derived of a human IgG1.

In an preferred embodiment the Fc domain of the CD80 extracellular domain Fc-fusion protein comprises or consists of the following sequence:

```
                                                    (SEQ ID NO: 2)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:2.

In a preferred embodiment the CD80 extracellular domain Fc-fusion protein comprises or consists of the following sequence:

```
                                                    (SEQ ID NO: 4)
VIHVTKEVKEVATLSCGHNVSVEELAQTRIYWQKEKKMVLTMMSGDMNIW

PEYKNRTIFDITNNLSIVILALRPSDEGTYECVVLKYEKDAFKREHLAEV
```

-continued

```
TLSVKADFPTPSISDFEIPTSNIRRIICSTSGGFPEPHLSWLENGEELNA

INTTVSQDPETELYAVSSKLDFNMTTNHSFMCLIKYGHLRVNQTFNWNTT

KQEHFPDDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTVD

KSRWQQGNVFSCSVMHEALHNHYTQKSLSLSPG
```

or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:4.

In a further preferred embodiment, the CD80 extracellular domain Fc-fusion protein comprises or consists of a CD80 extracellular domain fused to the Fc domain of an IgG1, wherein the CD80 extracellular domain comprises or consists of amino acids 1-207 of SEQ ID NO:4 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 1-207 of SEQ ID NO:4 and the Fc domain comprises or consists of amino acids 208-433 of SEQ ID NO:4 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to amino acids 208-433 of SEQ ID NO:4

In a further preferred embodiment the CD80 extracellular domain Fc-fusion protein comprises or consists of the following sequence:

```
                                           (SEQ ID NO: 3)
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPG
```

or a sequence having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

Functional variants of a CD80 extracellular domain Fc-fusion protein include biologically active variants and biologically active fragments of the foregoing described CD80 extracellular domain Fc-fusion proteins. The functional variants may either have variations in the CD80 extracellular domain, the Fc-domain and/or in both domains. By way of example, some CD80 extracellular domain functional variants have been described in WO2017181152. In another example, functional variants of the Fc-domain have been described in WO17079117 and comprise e.g. human IgG1 Fc domains with L234F, L235E, and/or P331S amino acid substitutions.

For example, variants may have one or more different amino acids in a position of a specifically described CD80 extracellular domain or Fc-domain protein. Variants can share at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid identity with such a CD80 extracellular domain or Fc domain. Fragments have the same amino acids as a given specifically described CD80 extracellular domain or Fc domain protein but may lack a specific portion or area of the CD80 extracellular domain or Fc domain protein.

Functional variants of the CD80 extracellular domain Fc-fusion protein only include variants and fragments of CD80 extracellular domain Fc-fusion protein that are biologically active. For the invention, the biological activity of the CD80 extracellular domain Fc-fusion protein variant or the CD80 extracellular domain Fc-fusion protein fragment—which is encoded in the genome of a recombinant rhabdovirus—is determined after its expression in a respective cell or tumor cell. This means that the biological activity is determined in the context of a recombinant rhabdovirus encoding for the CD80 extracellular domain Fc-fusion protein variant or the CD80 extracellular domain Fc-fusion protein fragment (e.g. in a Transwell assay or in vitro tumor model). Preferably, the biological activity is determined with a vesiculovirus encoding for the CD80 extracellular domain Fc-fusion protein variant or the CD80 extracellular domain Fc-fusion protein fragment. More preferably, the biological activity is determined with a VSV-GP encoding for the CD80 extracellular domain Fc-fusion protein variant or the CD80 extracellular domain Fc-fusion protein fragment.

Biological activity can include one or more of the following abilities: chemoattractant activity, anti-tumor activity, modulation of cytokine expression such as increase in the expression of Interferon-gamma (IFN-gamma) polypeptides or decrease in the expression of transforming growth factor-beta (TGF-beta) polypeptides in a population of syngeneic mammalian cells including CD8 positive T cells, CD4 positive T cells, antigen presenting cells and tumor cells. Testing for biological activity may be done without limitation for example according to the protocol as shown in the Examples. For the purpose of the invention the functional variant or fragment of the CD80 extracellular domain Fc-fusion protein is biologically active if it shows at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% of the activity of a CD80 extracellular domain Fc-fusion protein with the sequence as shown in SEQ ID NO:3 or 4 (respectively with or without signal peptide sequence) if tested in the same assay and under the same conditions.

Rhabdoviruses have negative sense single-stranded RNA (ssRNA) as their genetic material (genome). Negative sense ssRNA viruses need RNA polymerase to form a positive sense RNA. The positive-sense RNA acts as a viral mRNA, which is translated into proteins for the production of new virus materials. With the newly formed virus, more negative sense RNA molecules are produced.

A typical rhabdovirus genome encodes for at least five structural proteins in the order of 3'-N-P-M-G-L-5'. The genome might contain further short intergenic regions or additional genes between the structural proteins and therefore might vary in length and organization.

According to the invention the CD80 extracellular domain Fc-fusion protein gene can be introduced into any location of the rhabdovirus genome. Depending on the insertion site the transcription efficiency of the CD80 extracellular domain Fc-fusion protein gene can be influenced. In general, transcription efficiency of the CD80 extracellular domain Fc-fusion protein gene decreases from 3' insertion to 5' prime insertion. The CD80 extracellular domain Fc-fusion protein gene may be inserted into the following genome locations: 3'-CD80 extracellular domain Fc-fusion protein-N-P-M-G-L-5', 3'-N-CD80 extracellular domain Fc-fusion protein-P-M-G-L-5', 3'-N-P-CD80 extracellular domain Fc-fusion protein-M-G-L-5', 3'-N-P-M-CD80 extracellular domain Fc-fusion protein-G-L-5', 3'-N-P-M-G-CD80 extracellular domain Fc-fusion protein-L-5' or 3'-N-P-M-G-L-CD80 extracellular domain Fc-fusion protein-5'. In a preferred embodiment the CD80 extracellular domain Fc-fusion protein gene is inserted between the G protein and the L protein.

After infection of tumor cells the CD80 extracellular domain Fc-fusion protein gene encoded in the genome of the recombinant rhabdovirus is transcribed into positive sense RNA and then translated into CD80 extracellular domain Fc-fusion protein by the tumor cell. The term “encoding” or “coding” refers to the inherent property of specific sequences of nucleotides in a nucleic acid to serve as templates for synthesis of other polymers and macromolecules in biological processes having a defined sequence of nucleotides (e.g. RNA molecules) or amino acids and the biological properties resulting therefrom. Accordingly, a gene codes for a protein if the desired protein is produced in a cell or another biological system by transcription and subsequent translation of the mRNA. Both the coding strand, the nucleotide sequence of which is identical to the mRNA sequence and the non-coding strand may serve as the template for the transcription of a gene and can be referred to as encoding the protein or other product of that gene. Nucleic acids and nucleotide sequences that encode proteins may include introns.

The transcription of the CD80 extracellular domain Fc-fusion protein gene is preferably not under the control of its own promoter and only strictly linked to viral replication ensuring thereby targeted expression of CD80 extracellular domain Fc-fusion protein to the location of viral replication and spread (tumor). Thus, the transcription of the CD80 extracellular domain Fc-fusion protein gene is not controlled by additional elements such as promoters or inducible gene expression elements.

The translated CD80 extracellular domain Fc-fusion protein typically exists in solution as a dimeric fusion protein comprising two identical monomeric mature CD80 extracellular domain Fc-fusion proteins. In this instance, each monomeric CD80 extracellular domain Fc-fusion protein comprises a CD80 extracellular domain fused at its C-terminus to the N-terminus of an IgG Fc domain. The two CD80 extracellular domain Fc-fusion monomers are covalently linked together by disulfide bonds formed between cysteine residues in each monomer, thereby forming the CD80 extracellular domain Fc-fusion protein dimer.

It will be appreciated that a nucleic acid sequence may be varied with or without changing the primary sequence of the encoded polypeptide. A nucleic acid that encodes a protein includes any nucleic acids that have different nucleotide sequences but encode the same amino acid sequence of the protein due to the degeneracy of the genetic code. It is within the knowledge of the skilled artisan to choose a nucleic acid sequence that will result in the expression of a CD80 extracellular domain Fc-fusion protein and in particular to any specific CD80 extracellular domain Fc-fusion protein proteins as disclosed herein. Nucleic acid molecules encoding amino acid sequences of CD80 extracellular domain Fc-fusion protein are prepared by a variety of methods known in the art. These methods include, but are not limited to, isolation from a natural source or preparation by oligonucleotide-mediated (or site-directed) mutagenesis, PCR mutagenesis, and cassette mutagenesis of an earlier prepared CD80 extracellular domain Fc-fusion protein.

Pharmaceutical Compositions

The actual pharmaceutically effective amount or therapeutic dosage will of course depend on factors known by those skilled in the art such as age and weight of the patient, route of administration and severity of disease. In any case the recombinant rhabdovirus will be administered at dosages and in a manner which allows a pharmaceutically effective amount to be delivered based upon patient's unique condition.

Generally, for the treatment and/or alleviation of the diseases, disorders and conditions mentioned herein and depending on the specific disease, disorder or condition to be treated, the potency of the specific recombinant rhabdovirus of the invention to be used, the specific route of administration and the specific pharmaceutical formulation or composition used, the recombinant rhabdovirus of the invention will generally be administered for example, twice a week, weekly, or in monthly doses, but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

To be used in therapy, the recombinant rhabdovirus of the invention is formulated into pharmaceutical compositions appropriate to facilitate administration to animals or humans. Typical formulations can be prepared by mixing the recombinant virus with physiologically acceptable carriers, excipients or stabilizers, in the form of aqueous solutions or aqueous or non-aqueous suspensions. Carriers, excipients, modifiers or stabilizers are nontoxic at the dosages and concentrations employed. They include buffer systems such as phosphate, citrate, acetate and other inorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. The excipients may also have a release-modifying or absorption-modifying function.

In one embodiment the recombinant rhabdovirus of the invention is formulated into a pharmaceutical composition comprising Tris, arginine and optionally citrate. Tris is preferably used in a concentration of about 1 mM to about 100 mM. Arginine is preferably used in a concentration of about 1 mM to about 100 mM. Citrate may be present in a concentration up to 100 mM. A preferred formulation comprises about 50 mM Tris and 50 mM arginine.

The pharmaceutical composition may be provided as a liquid, a frozen liquid or in a lyophilized form. The frozen liquid may be stored at temperatures between about 0° C. and about −85° C. including temperatures between −70° C. and −85° C. and of about −15° C., −16° C., −17° C., −18° C., −19° C., −20° C., −21° C., −22° C., −23° C., −24° C. or about −25° C.

The recombinant rhabdovirus or pharmaceutical composition of the invention need not be, but is optionally, formulated with one or more agents currently used to prevent or treat the disorder in question. The effective amount of such other agents depends on the amount of recombinant antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the recombinant rhabdovirus or pharmaceutical composition of the invention (when used alone or in combination with one or more other additional therapeutic agents) will depend on the type of disease to be treated, the type of recombinant rhabdovirus, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus or pharmaceutical composition of the invention suitably administered to the patient at one time or over a series of treatments.

Depending on the type and severity of the disease, about $10^8$ to $10^{13}$ infectious particles measured by $TCID_{50}$ of the recombinant rhabdovirus can be an initial candidate dosage for administration to the patient, whether, for example, by one or more separate administrations, or by continuous infusion. For repeated administrations over several days or longer, depending on the condition, the treatment would generally be sustained until a desired suppression of disease symptoms occurs. One exemplary dosage of the recombinant rhabdovirus would be in the range from about $10^8$ to $10^{13}$ infectious particles measured by $TCID_{50}$. Thus, one or more doses of about $10^8$, $10^9$, $10^{10}$, $10^{11}$, $10^{12}$, or $10^{13}$ infectious particles measured by $TCID_{50}$ (or any combination thereof) may be administered to the patient. Such doses may be administered intermittently, e.g. every week or every three weeks (e.g. such that the patient receives from about two to about twenty, or e.g. about six doses of the recombinant rhabdovirus). An initial higher loading dose, followed by one or more lower doses or vice versa may be administered. However, other dosage regimens may be useful. The progress of this therapy is easily monitored by conventional techniques and assays.

The efficacy of the recombinant rhabdovirus of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

The actual pharmaceutically effective amount or therapeutic dosage will of course depend on factors known by those skilled in the art such as age and weight of the patient, route of administration and severity of disease. In any case the recombinant rhabdovirus of the invention will be administered at dosages and in a manner which allows a pharmaceutically effective amount to be delivered based upon patient's unique condition.

Alternatively, the recombinant rhabdovirus or pharmaceutical composition of the invention may be delivered in a volume of from about 50 µl to about 100 ml including all numbers within the range, depending on the size of the area to be treated, the viral titer used, the route of administration, and the desired effect of the method.

For intratumoral administration the volume is preferably between about 50 µl to about 5 ml including volumes of about 100 µl, 200 µl, 300 µl, 400 µl, 500 µl, 600 µl, 700 µl, 800 µl, 900 µl, 1000 µl, 1100 µl, 1200 µl, 1300 µl, 1400 µl, 1500 µl, 1600 µl, 1700 µl, 1800 µl, 1900 µl, 2000 µl, 2500 µl, 3000 µl, 3500 µl, 4000 µl, or about 4500 µl. In a preferred embodiment the volume is about 1000 µl.

For systemic administration, e.g. by infusion of the recombinant rhabdovirus the volumes may be naturally higher. Alternatively, a concentrated solution of the recombinant rhabdovirus could be diluted in a larger volume of infusion solution directly before infusion.

In particular for intravenous administration the volume is preferably between 1 ml and 100 ml including volumes of about 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 25 ml, 30 ml, 35 ml, 40 ml, 45 ml, 50 ml, 55 ml, 60 ml, 70 ml, 75 ml, 80 ml, 85 ml, 90 ml, 95 ml, or about 100 ml. In a preferred embodiment the volume is between about 5 ml and 15 ml, more preferably the volume is about 6 ml, 7 ml, 8 ml, 9 ml, 10 ml, 11 ml, 12 ml, 13 ml, or about 14 ml.

Preferably the same formulation is used for intratumoral administration and intravenous administration. The doses and/or volume ratio between intratumoral and intravenous administration may be about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or about 1:20. For example, a doses and/or volume ratio of 1:1 means that the same doses and/or volume is administered intratumorally as well as intravenously, whereas e.g. a doses and/or volume ratio of about 1:20 means an intravenous administration dose and/or volume that is twenty times higher than the intratumoral administration dose and/or volume. Preferably, the doses and/or volume ratio between intratumoral and intravenous administration is about 1:9.

An effective concentration of a recombinant rhabdovirus desirably ranges between about $10^8$ and $10^{14}$ vector genomes per milliliter (vg/mL). The infectious units may be measured as described in McLaughlin et al., J Virol.; 62(6):1963-73 (1988). Preferably, the concentration is from about $1.5\times10^9$ to about $1.5\times10^{13}$, and more preferably from about $1.5\times10^9$ to about $1.5\times10^{11}$. In one embodiment, the effective concentration is about $1.5\times10^9$. In another embodiment, the effective concentration is about $1.5\times10^{10}$. In another embodiment, the effective concentration is about $1.5\times10^{11}$. In yet another embodiment, the effective concentration is about $1.5\times10^{12}$. In another embodiment, the effective concentration is about $1.5\times10^{13}$. In another embodiment, the effective concentration is about $1.5\times10^{14}$. It may be desirable to use the lowest effective concentration in order to reduce the risk of undesirable effects. Still other dosages in these ranges may be selected by the attending physician, taking into account the physical state of the subject, preferably human, being treated, the age of the subject, the particular type of cancer and the degree to which the cancer, if progressive, has developed.

An effective target concentration of a recombinant rhabdovirus may be expressed with the $TCID_{50}$. The $TCID_{50}$ can be determined for example by using the method of Spearman-Kärber. Desirably ranges include an effective target concentration between $1\times10^8$/ml and $1\times10^{14}$/ml $TCID_{50}$. Preferably, the effective target concentration is from about $1\times10^9$ to about $1\times10^{12}$/ml, and more preferably from about $1\times10^9$ to about $1\times10^{11}$/ml. In one embodiment, the effective target concentration is about $1\times10^{10}$/ml. In a preferred embodiment the target concentration is $5\times10^{10}$/ml. In another embodiment, the effective target concentration is about $1.5\times10^{11}$/ml. In one embodiment, the effective target concentration is about $1\times10^{12}$/ml. In another embodiment, the effective target concentration is about $1.5\times10^{13}$/ml.

An effective target dose of a recombinant rhabdovirus may also be expressed with the $TCID_{50}$. Desirably ranges include a target dose between $1\times10^8$ and $1\times10^{14}$ $TCID_{50}$. Preferably, the target dose is from about $1\times10^9$ to about $1\times10^{13}$, and more preferably from about $1\times10^9$ to about $1\times10^{12}$. In one embodiment, the effective concentration is about $1\times10^{10}$. In a preferred embodiment, the effective concentration is about $1\times10^{11}$. In one embodiment, the effective concentration is about $1\times10^{12}$. In another embodiment, the effective concentration is about $1\times10^{13}$.

In another aspect, a kit or kit-of-parts containing materials useful for the treatment, prevention and/or diagnosis of the disorders described herein is provided. The kit or kit-of-parts comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is the recombinant rhabdovirus or pharmaceutical composition of the invention. The label or package insert indicates that the composition is used for treating the condition of choice.

Moreover, the kit or kit-of-parts may comprise (a) a first container with a composition contained therein, wherein the composition comprises the recombinant rhabdovirus or pharmaceutical composition of the invention; and (b) a second container with a composition contained therein, wherein the composition comprises a further cytotoxic or otherwise therapeutic agent, such as a PD-1 pathway inhibitor or SMAC mimetic. The kit or kit-of-parts in this embodiment of the invention may further comprise a package insert indicating that the compositions can be used to treat a particular condition, in particular cancer. Alternatively, or additionally, the kit or kit-of-parts may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In a further aspect, a recombinant rhabdovirus of the invention is used in combination with a device useful for the administration of the recombinant rhabdovirus, such as a syringe, injector pen, micropump, or other device. Preferably, a recombinant rhabdovirus of the invention is comprised in a kit of parts, for example also including a package insert with instructions for the use of the recombinant rhabdovirus.

Medical Uses

A further aspect of the invention provides a recombinant rhabdovirus encoding in its genome at least one CD80 extracellular domain Fc-fusion protein or a functional variant thereof for use in medicine.

The recombinant rhabdovirus of the invention efficiently induces tumor cell lysis combined with immunogenic cell death and stimulation of innate immune cells in the tumor microenvironment. Accordingly, the recombinant rhabdovirus of the invention are useful for the treatment and/or prevention of cancer.

In a further aspect, the recombinant rhabdovirus of the invention can be used in a method for treating and/or preventing cancer, comprising administering a therapeutically effective amount of a recombinant rhabdovirus to an individual suffering from cancer, thereby ameliorating one or more symptoms of cancer.

In yet a further aspect the invention further provides for the use of a recombinant rhabdovirus according to the invention for the manufacture of a medicament for treatment and/or prevention of cancer.

In yet a further aspect, the recombinant rhabdovirus of the invention can be used in a method for treating and/or preventing gastrointestinal cancer, lung cancer or head & neck cancer, comprising administering a therapeutically effective amount of a recombinant rhabdovirus to an individual suffering from gastrointestinal cancer, lung cancer or head & neck cancer, thereby ameliorating one or more symptoms of gastrointestinal cancer, lung cancer or head & neck cancer.

For the prevention or treatment of a disease, the appropriate dosage of recombinant rhabdovirus will depend on a variety of factors such as the type of disease to be treated, as defined above, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus is suitably administered to the patient at one time or over a series of treatments.

In one aspect, the cancer is a solid cancer. The solid cancer may be brain cancer, endometrial cancer, vaginal cancer, anal cancer, colorectal cancer, oropharyngeal squamous cell carcinoma, gastric cancer, gastroesophageal junction adenocarcinoma, esophageal carcinoma, hepatocellular carcinoma, pancreatic adenocarcinoma, cholangiocarcinoma, bladder urothelial carcinoma, metastatic melanoma, prostate carcinoma, breast carcinoma, ovarian cancer, a head and neck squamous-cell carcinoma (HNSCC), glioblastoma, non-small cell lung cancer, brain tumor or small cell lung cancer. Preferred is the treatment of gastrointestinal cancer, lung cancer and head & neck cancer.

The recombinant rhabdovirus is administered by any suitable means, including oral, parenteral, subcutaneous, intratumoral, intravenous, intradermal, intraperitoneal, intrapulmonary, and intranasal. Parenteral infusions include intramuscular, intravenous, intraarterial, intraperitoneal, or subcutaneous administration. In addition, the recombinant rhabdovirus is suitably administered by pulse infusion. In one aspect, the dosing is given by injections, most preferably intravenous or subcutaneous injections, depending in part on whether the administration is brief or chronic.

Depending on the specific recombinant rhabdovirus of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The treatment schedule may include various regimens and in typical will require multiple doses administered to the patient over a period of one, two, three or four weeks optionally followed by one or more further rounds of treatment. In one aspect, the recombinant rhabdovirus of the invention is administered to the patient in up to 1, 2, 3, 4, 5, or 6 doses within a given period of time. Preferably, the first round of treatment(s) is concluded within three weeks. During the course of the three week treatment the recombinant rhabdovirus may be administered to the patient as described in the following schemes: (i) once on day 0 (ii) on day 0 and day 3; (iii) on day 0, day 3 and day 6; (iv) on day 0, day 3, day 6, and day 9; (v) on day 0 and day 5; (vi) on day 0, day 5 and day 10; (vii) on day 0, day 5, day 10 and day 15. These regimens may be repeated and a second or third round of treatment may be needed depending on the outcome of the first round of treatment. Calculated on the basis of the first round of treatments the second round of treatment preferably includes further treatments on day 21, day 42 and day 63. In a preferred embodiment the recombinant rhabdovirus of the invention is administered to the patient according the following scheme: on day 0, day 3, day 21, day 42 and day 63.

The term "suppression" is used herein in the same context as "amelioration" and "alleviation" to mean a lessening or diminishing of one or more characteristics of the disease. The recombinant rhabdovirus or pharmaceutical composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the recombinant rhabdovirus to be administered will be governed by such considerations, and is the minimum amount necessary to prevent, ameliorate, or treat clinical symptoms of cancer, in particular the minimum amount which is effective to these disorders.

In another aspect the recombinant rhabdovirus of the invention can be administered multiple times and in several doses. In one aspect, the first dose of the recombinant rhabdovirus is administered intratumorally and subsequent doses of the recombinant rhabdovirus are administered intravenously. In a further aspect, the first dose and at least one or more following doses of the recombinant rhabdovirus is/are administered intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

In another aspect, the first dose of the recombinant rhabdovirus is administered intravenously and subsequent doses of the recombinant rhabdovirus are administered intratumorally. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intravenous administration.

In another aspect, the recombinant rhabdovirus is administered intravenously and subsequent doses of the recombinant rhabdovirus are administered intratumorally.

In another aspect, the recombinant rhabdovirus is administered at each time point intravenously and intratumorally.

As stated above, the recombinant rhabdovirus of the invention have much utility for stimulating an immune response against cancer cells. The strong immune activating potential was observed to be restricted to the tumor microenvironment. Thus, in a preferred aspect, the recombinant rhabdovirus of the invention may be administered systemically to a patient. Systemic applicability is a crucial attribute, as many cancers are highly metastasized and it will permit the treatment of difficult to access as well as non-accessible tumor lesions. Due to this unique immune stimulating properties the recombinant rhabdovirus according to the invention are especially useful for treatment of metastasizing tumors.

Some patients develop resistance to checkpoint inhibitor therapy and it was observed that such patients seem to accumulate mutations in the IFN pathway. Therefore in one aspect, the recombinant rhabdovirus of the invention and in particular the recombinant vesicular stomatitis virus of the invention is useful for the treatment of patients who developed a resistance to checkpoint inhibitor therapy. Due to the unique immune promoting properties of the recombinant rhabdovirus and in particular the recombinant vesicular stomatitis virus of the invention such treated patients may become eligible for continuation of checkpoint inhibitor therapy.

In a preferred embodiment, the recombinant rhabdovirus of the invention and in particular the recombinant vesicular stomatitis virus of the invention is useful for the treatment of patients with non-small cell lung cancer which have completed checkpoint inhibitor therapy with either a PD-1 or PD-L1 inhibitor, e.g. antagonistic antibodies to PD-1 or PD-L1.

It is understood that any of the above pharmaceutical formulations or therapeutic methods may be carried out using any one of the inventive recombinant rhabdovirus or pharmaceutical compositions.

Combinations

The present invention also provide combination treatments/methods providing certain advantages compared to treatments/methods currently used and/or known in the prior art. These advantages may include in vivo efficacy (e.g. improved clinical response, extend of the response, increase of the rate of response, duration of response, disease stabilization rate, duration of stabilization, time to disease progression, progression free survival (PFS) and/or overall survival (OS), later occurrence of resistance and the like), safe and well tolerated administration and reduced frequency and severity of adverse events.

The recombinant rhabdovirus of the invention may be used in combination with other pharmacologically active ingredients, such as state-of-the-art or standard-of-care compounds, such as e.g. cytostatic or cytotoxic substances, cell proliferation inhibitors, anti-angiogenic substances, steroids, immune modulators/checkpoint inhibitors, and the like. The recombinant rhabdovirus of the invention may also be used in combination with radiotherapy.

Cytostatic and/or cytotoxic active substances which may be administered in combination with recombinant rhabdovirus of the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insulin-like growth factors (IGF), human epidermal growth factor (HER, e.g. HER2, HER3, HER4) and hepatocyte growth factor (HGF)), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/ FAK inhibitors), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/ Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; Flt3L as well as Flt3-stimulating antibodies or ligand mimetics; SIRPalpha & CD47 blocking therapeutics; and/or cyclin-dependent kinase 9 inhibitors.

Furthermore, the potential conversion of immunological "cold" into "hot" tumors, myeloid/dendritic cell activation in conjunction with CD80-Fc mediated T-cell activation further favourably interacts with therapeutic modalities, such as T-cell engagers. Thus, in one embodiment the recombinant rhabdovirus of the invention can be used in combination treatment with T-cell engagers, such as e.g. bispecific DLL3/ CD3 binders, which provide T-cell receptor stimulation, but no co-stimulation. Additionally, potential clinical combination partners may also include tumor-vasculature modulating agents. Thus, in another embodiment the recombinant rhabdovirus of the invention can be used in combination treatment with tumor vasculature modulating agents, such as e.g. bispecific VEGF/ANG2 binders.

The recombinant rhabdovirus of the invention can be used in combination treatment with either a PD-1 pathway inhibitor or a SMACm/IAP antagonist. Such a combined treatment may be given as a non-fixed (e.g. free) combination of the substances or in the form of a fixed combination, including kit-of-parts.

In this context, "combination" or "combined" within the meaning of this invention includes, without being limited, a product that results from the mixing or combining of more than one active agent and includes both fixed and non-fixed (e.g. free) combinations (including kits) and uses, such as e.g. the simultaneous, concurrent, sequential, successive, alternate or separate use of the components or agents. The term "fixed combination" means that the active agents are both administered to a patient simultaneously in the form of a single entity or dosage. The term "non-fixed combination" means that the active agents are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active agents.

The invention provides for a recombinant rhabdovirus in combination with a PD-1 pathway inhibitor or a SMACm/IAP antagonist for use in the treatment of cancers as described herein, preferably for the treatment of solid cancers.

The invention also provides for the use of a recombinant rhabdovirus in combination with a PD-1 pathway inhibitor or a SMACm/IAP antagonist for the manufacture of a medicament for treatment and/or prevention of cancers as described herein, preferably for the treatment of solid cancers.

The invention further provides for a method for treating and/or preventing cancer, comprising administering a therapeutically effective amount of a recombinant rhabdovirus of the invention, and a PD-1 pathway inhibitor or a SMACm/IAP antagonist to an individual suffering from cancer, thereby ameliorating one or more symptoms of cancer. The recombinant rhabdovirus of the invention and the PD-1 pathway inhibitor or the SMACm/IAP antagonist may be administered concomitantly, sequentially or alternately.

The recombinant rhabdovirus of the invention and the PD-1 pathway inhibitor or a SMACm/IAP antagonist may be administered by the same administration routes or via different administration routes. Preferably, the PD-1 pathway inhibitor or SMACm/IAP antagonist is administered intravenously and the recombinant rhabdovirus of the invention is administered intratumorally. In another embodiment, the PD-1 pathway inhibitor or the SMACm/IAP antagonist is administered intravenously and the recombinant rhabdovirus of the invention is administered at least once intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration. In a preferred embodiment the PD-1 pathway inhibitor or the SMACm/IAP antagonists is administered 21 days after the initial intratumoral administration.

Particularly preferred are treatments with the recombinant rhabdovirus of the invention in combination with:

(i) SMAC mimetica (SMACm)/IAP antagonists, (ii) immunotherapeutic agents, including anti-PD-1 and anti-PD-L1 agents and anti LAG3 agents, such as pembrolizumab and nivolumab and antibodies as disclosed in WO2017/198741.

A combination as herein provided comprises (i) a recombinant rhabdovirus of the invention and (iia) a PD-1 pathway inhibitor, preferably an antagonistic antibody which is directed against PD-1 or PD-L1 or (iib) a SMACm/IAP antagonists. Further provided is the use of such a combination comprising (i) and (iia) or (i) and (iib) for the treatment of cancers as described herein.

In another aspect a combination treatment is provided comprising the use of (i) a recombinant rhabdovirus of the invention and (iia) a PD-1 pathway inhibitor or (iib) a SMACm/IAP antagonists. In such combination treatment the recombinant rhabdovirus of the invention may be administered concomitantly, sequentially or alternately with the PD-1 pathway inhibitor or SMACm/IAP antagonists.

For example, "concomitant" administration includes administering the active agents within the same general time period, for example on the same day(s) but not necessarily at the same time. Alternate administration includes administration of one agent during a time period, for example over the course of a few days or a week, followed by administration of the other agent during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent during a second time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Sequential treatment schedules include administration of the recombinant rhabdovirus of the invention followed by administration of the PD-1 pathway inhibitor or the SMACm/IAP antagonists. Sequential treatment schedules also include administration of the PD-1 pathway inhibitor or the SMACm/IAP antagonists followed by administration of the recombinant rhabdovirus of the invention. Sequential treatment schedules may include administrations 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after each other.

A PD-1 pathway inhibitor within the meaning of this invention and all of its embodiments is a compound that inhibits the interaction of PD-1 with its receptor(s). A PD-1 pathway inhibitor is capable to impair the PD-1 pathway signaling, preferably mediated by the PD-1 receptor. The PD-1 inhibitor may be any inhibitor directed against any member of the PD-1 pathway capable of antagonizing PD-1 pathway signaling. The inhibitor may be an antagonistic antibody targeting any member of the PD-1 pathway, preferably directed against PD-1 receptor, PD-L1 or PD-L2. Also, the PD-1 pathway inhibitor may be a fragment of the PD-1 receptor or the PD-1 receptor blocking the activity of PD1 ligands.

PD-1 antagonists are well-known in the art, e.g. reviewed by Li et al., Int. J. Mol. Sci. 2016, 17, 1151 (incorporated herein by reference). Any PD-1 antagonist, especially antibodies, such as those disclosed by Li et al. as well as the further antibodies disclosed herein below, can be used according to the invention. Preferably, the PD-1 antagonist of this invention and all its embodiments is selected from the group consisting of the following antibodies:

- pembrolizumab (anti-PD-1 antibody);
- nivolumab (anti-PD-1 antibody);
- pidilizumab (anti-PD-1 antibody);
- PDR-001 (anti-PD-1 antibody);
- PD1-1, PD1-2, PD1-3, PD1-4, and PD1-5 as disclosed herein below (anti-PD-1 antibodies)
- atezolizumab (anti-PD-L1 antibody);
- avelumab (anti-PD-L1 antibody);
- durvalumab (anti-PD-L1 antibody).

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1k monoclonal antibody that binds to PD-1. Pidilizumab is e.g. disclosed in WO2009/101611.

PDR-001 or PDR001 is a high-affinity, ligand-blocking, humanized anti-PD-1 IgG4 antibody that blocks the binding of PD-L1 and PD-L2 to PD-1. PDR-001 is disclosed in WO2015/112900 and WO2017/019896.

Antibodies PD1-1 to PD1-5 are antibody molecules defined by the sequences as shown in Table 1, wherein HC denotes the (full length) heavy chain and LC denotes the (full length) light chain:

TABLE 1

| SEQ ID NO: | Sequence name | Amino acid sequence |
|---|---|---|
| 14 | HC of PD1-1 | EVMLVESGGGLVQPGGSLRLSCTASGFTFSASAMSWVRQAPGKGLEWVAYI<br>SGGGGDTYYSSSVKGRFTISRDNAKNSLYLQMNSLRAEDTAVYYCARHSNV<br>NYYAMDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYS<br>RLTVDKSRWQEGNVFSCSVMHEALHNHYTQKSLSLSLG |
| 15 | LC of PD1-1 | EIVLTQSPATLSLSPGERATMSCRASENIDTSGISFMNWYQQKPGQAPKLL<br>IYVASNQGSGIPARFSGSGSGTDFTLTISRLEPEDFAVYYCQQSKEVPWTF<br>GQGTKLEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQG<br>LSSPVTKSFNRGEC |
| 16 | HC of PD1-2 | EVMLVESGGGLVQPGGSLRLSCTASGFTFSASAMSWVRQAPGKGLEWVAYI<br>SGGGGDTYYSSSVKGRFTISRDNAKNSLYLQMNSLRAEDTAVYYCARHSNP<br>NYYAMDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYS<br>RLTVDKSRWQEGNVFSCSVMHEALHNHYTQKSLSLSLG |
| 17 | LC of PD1-2 | EIVLTQSPATLSLSPGERATMSCRASENIDTSGISFMNWYQQKPGQAPKLL<br>IYVASNQGSGIPARFSGSGSGTDFTLTISRLEPEDFAVYYCQQSKEVPWTF<br>GQGTKLEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQG<br>LSSPVTKSFNRGEC |
| 18 | HC of PD1-3 | EVMLVESGGGLVQPGGSLRLSCTASGFTFSKSAMSWVRQAPGKGLEWVAYI<br>SGGGGDTYYSSSVKGRFTISRDNAKNSLYLQMNSLRAEDTAVYYCARHSNV<br>NYYAMDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPPCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE |

TABLE 1-continued

| SEQ ID NO: | Sequence name | Amino acid sequence |
|---|---|---|
| | | MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 19 | LC of PD1-3 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 20 | HC of PD1-4 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 21 | LC of PD1-4 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |
| 22 | HC of PD1-5 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLG |
| 23 | LC of PD1-5 | EIVLTQSPATLSLSPGERATMSCRASENIDVSGISFMNWYQQKPGQAPKLL IYVASNQGSGIPARFSGSGSGTDFTLTISRLEPEDFAVYYCQQSKEVPWTF GQGTKLEIKRTVAAPSVFIFPPSDEQLKSGTASVVCLLNNFYPREAKVQWK VDNALQSGNSQESVTEQDSKDSTYSLSSTLTLSKADYEKHKVYACEVTHQG LSSPVTKSFNRGEC |

Specifically, the anti-PD-1 antibody molecule described herein above has:

(PD1-1:) a heavy chain comprising the amino acid sequence of SEQ ID NO:14 and a light chain comprising the amino acid sequence of SEQ ID NO:15; or (PD1-2:) a heavy chain comprising the amino acid sequence of SEQ ID NO:16 and a light chain comprising the amino acid sequence of SEQ ID NO:17; or (PD1-3:) a heavy chain comprising the amino acid sequence of SEQ ID NO:18 and a light chain comprising the amino acid sequence of SEQ ID NO:19; or (PD1-4:) a heavy chain comprising the amino acid sequence of SEQ ID NO:20 and a light chain comprising the amino acid sequence of SEQ ID NO:21; or (PD1-5:) a heavy chain comprising the amino acid sequence of SEQ ID NO:22 and a light chain comprising the amino acid sequence of SEQ ID NO:23.

Atezolizumab (Tecentriq, also known as MPDL3280A) is a phage-derived human IgG1k monoclonal antibody targeting PD-L1 and is described e.g. in Deng et al. mAbs 2016; 8:593-603. It has been approved by the FDA for the treatment of patients suffering from urothelial carcinoma.

Avelumab is a fully human anti-PD-L1 IgG1 monoclonal antibody and described in e.g. Boyerinas et al. Cancer Immunol. Res. 2015; 3:1148-1157.

Durvalumab (MEDI4736) is a human IgG1k monoclonal antibody with high specificity to PD-L1 and described in e.g. Stewart et al. Cancer Immunol. Res. 2015; 3:1052-1062 or in Ibrahim et al. Semin. Oncol. 2015; 42:474-483.

Further PD-1 antagonists disclosed by Li et al. (supra), or known to be in clinical trials, such as AMP-224, MEDI0680 (AMP-514), REGN2810, BMS-936559, JS001-PD-1, SHR-1210, BMS-936559, TSR-042, JNJ-63723283, MEDI4736, MPDL3280A, and MSB0010718C, may be used as alternative or in addition to the above mentioned antagonists.

The INNs as used herein are meant to also encompass all biosimilar antibodies having the same, or substantially the same, amino acid sequences as the originator antibody, including but not limited to those biosimilar antibodies authorized under 42 USC § 262 subsection (k) in the US and equivalent regulations in other jurisdictions.

PD-1 antagonists listed above are known in the art with their respective manufacture, therapeutic use and properties.

In one embodiment the PD-1 antagonist is pembrolizumab.

In another embodiment the PD-1 antagonist is nivolumab.

In another embodiment the PD-1 antagonist is pidilizumab.

In another embodiment the PD-1 antagonist is atezolizumab.

In another embodiment the PD-1 antagonist is avelumab.

In another embodiment the PD-1 antagonist is durvalumab.

In another embodiment the PD-1 antagonist is PDR-001.

In another embodiment the PD-1 antagonist is PD1-1.

In another embodiment the PD-1 antagonist is PD1-2.

In another embodiment the PD-1 antagonist is PD1-3.

In another embodiment the PD-1 antagonist is PD1-4.

In another embodiment the PD-1 antagonist is PD1-5.

The SMAC mimetic within the meaning of this invention and all its embodiments is a compound which binds to IAP proteins and induces their degradation. Preferably, the SMAC mimetic within this invention and all its embodiments is selected from the group consisting of the following (A0):

- a SMAC mimetic (i.e. a compound) as (generically and/or specifically) disclosed in WO 2013/127729, or a pharmaceutically acceptable salt thereof;
- a SMAC mimetic (i.e. a compound) as (generically and/or specifically) disclosed in WO 2015/025018, or a pharmaceutically acceptable salt thereof;
- a SMAC mimetic (i.e. a compound) as (generically and/or specifically) disclosed in WO 2015/025019, or a pharmaceutically acceptable salt thereof;
- a SMAC mimetic (i.e. a compound) as (generically and/or specifically) disclosed in WO 2016/023858, or a pharmaceutically acceptable salt thereof;
- a SMAC mimetic (i.e. a compound) as (generically and/or specifically) disclosed in WO 2008/0016893, or a pharmaceutically acceptable salt thereof;
- LCL161, i.e. compound A in example 1 of WO 2008/016893 (page 28/29; [122]), or a pharmaceutically acceptable salt thereof;
- the SMAC mimetic known as Debio-1143, or a pharmaceutically acceptable salt thereof;
- the SMAC mimetic known as birinapant, or a pharmaceutically acceptable salt thereof;
- the SMAC mimetic known as ASTX-660, or a pharmaceutically acceptable salt thereof;
- the SMAC mimetic known as CUDC-427, or a pharmaceutically acceptable salt thereof;
- any one of the SMAC mimetics 1 to 26 in table 2 or a pharmaceutically acceptable salt thereof:

TABLE 2

1

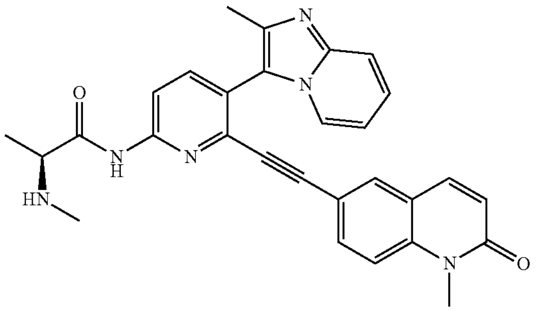 [SMILES: CN[C@@H](C)C(=O)Nc1ccc(-c2c(C)nc3ccccn23)c(C#Cc2ccc3c(ccc(=O)n3C)c2)n1]

TABLE 2-continued

2

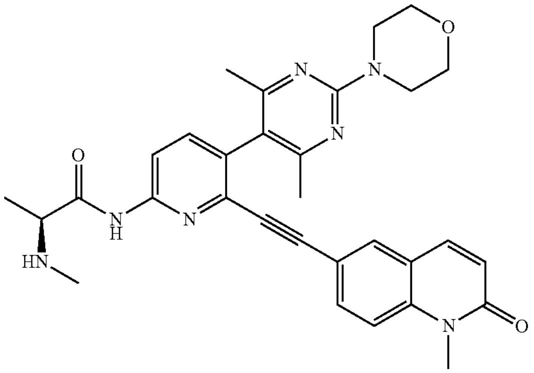 [SMILES: CN[C@@H](C)C(=O)Nc1ccc(-c2c(C)nc(N3CCOCC3)nc2C)c(C#Cc2ccc3c(ccc(=O)n3C)c2)n1]

3

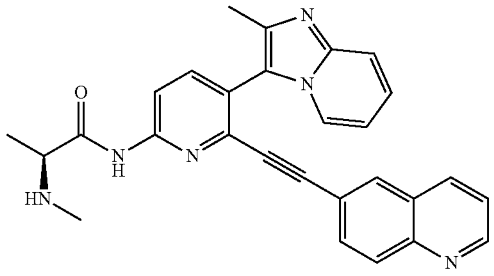 [SMILES: CN[C@@H](C)C(=O)Nc1ccc(-c2c(C)nc3ccccn23)c(C#Cc2ccc3ncccc3c2)n1]

4

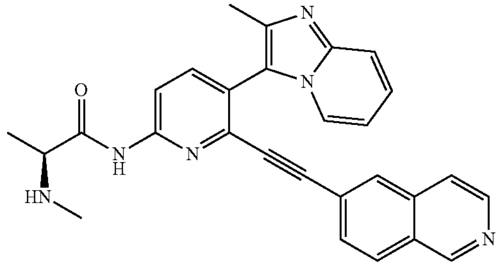 [SMILES: CN[C@@H](C)C(=O)Nc1ccc(-c2c(C)nc3ccccn23)c(C#Cc2ccc3cnccc3c2)n1]

5

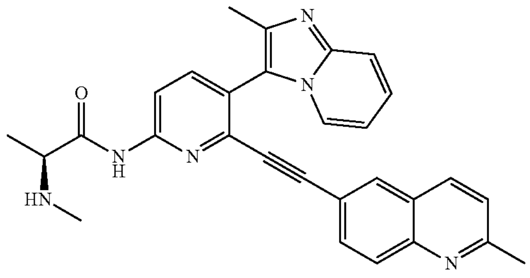 [SMILES: CN[C@@H](C)C(=O)Nc1ccc(-c2c(C)nc3ccccn23)c(C#Cc2ccc3nc(C)ccc3c2)n1]

6

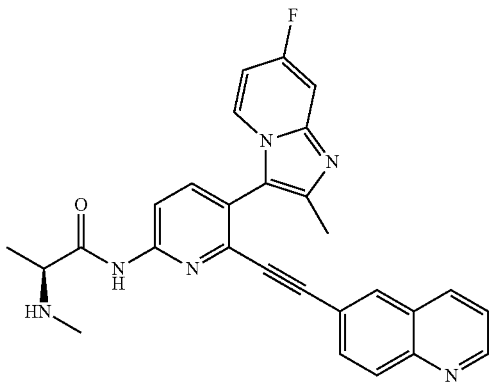 [SMILES: CN[C@@H](C)C(=O)Nc1ccc(-c2c(C)nc3cc(F)ccn23)c(C#Cc2ccc3ncccc3c2)n1]

TABLE 2-continued
7
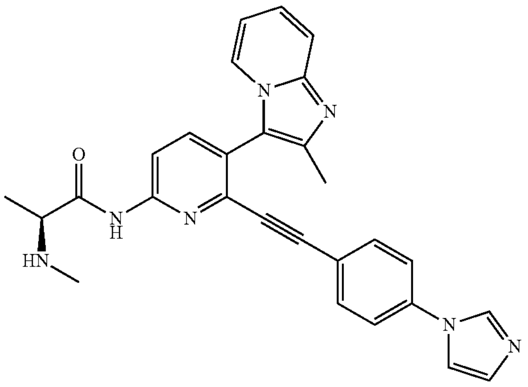 [SMILES: CN[C@@H](C)C(=O)Nc1ccc(-c2c(C)nc3ccccn23)c(C#Cc2ccc(-n3ccnc3)cc2)n1]
8
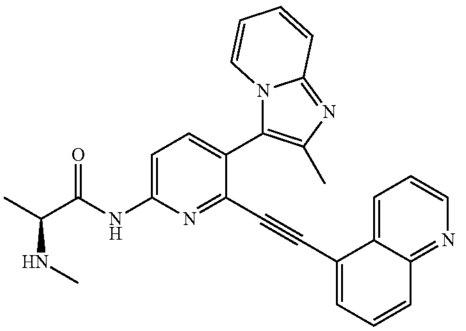 [SMILES: CN[C@@H](C)C(=O)Nc1ccc(-c2c(C)nc3ccccn23)c(C#Cc2cccc3ncccc23)n1]
9
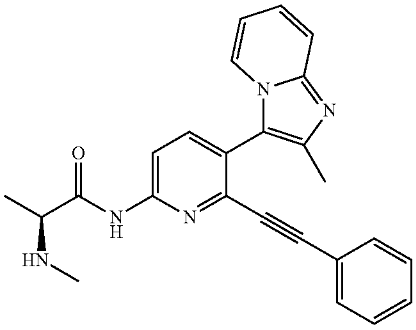 [SMILES: CN[C@@H](C)C(=O)Nc1ccc(-c2c(C)nc3ccccn23)c(C#Cc2ccccc2)n1]
10
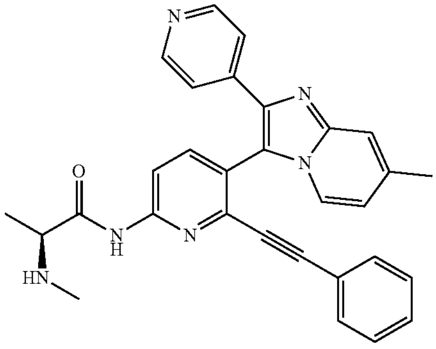 [SMILES: CN[C@@H](C)C(=O)Nc1ccc(-c2c(-c3ccncc3)nc3cc(C)ccn23)c(C#Cc2ccccc2)n1]
TABLE 2-continued
11
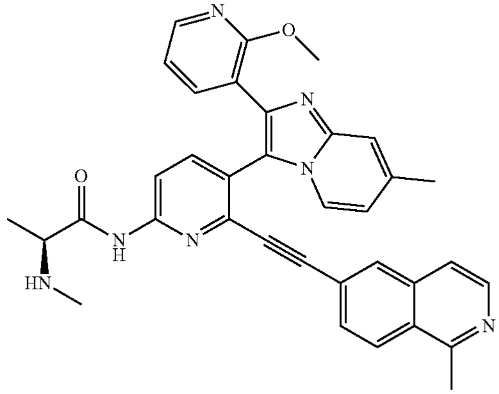 [SMILES: CN[C@@H](C)C(=O)Nc1ccc(-c2c(-c3cccnc3OC)nc3cc(C)ccn23)c(C#Cc2ccc3c(C)nccc3c2)n1]
12
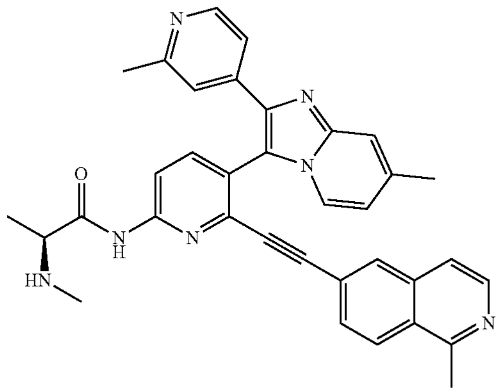 [SMILES: CN[C@@H](C)C(=O)Nc1ccc(-c2c(-c3ccnc(C)c3)nc3cc(C)ccn23)c(C#Cc2ccc3c(C)nccc3c2)n1]
13
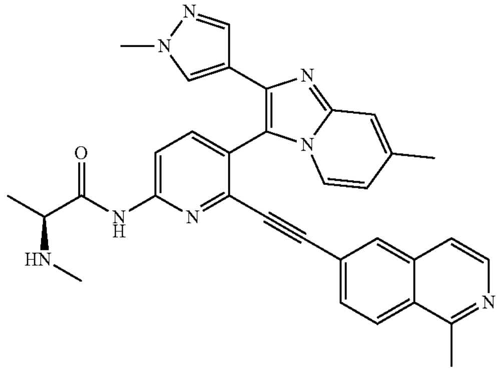 [SMILES: CN[C@@H](C)C(=O)Nc1ccc(-c2c(-c3cnn(C)c3)nc3cc(C)ccn23)c(C#Cc2ccc3c(C)nccc3c2)n1]
14
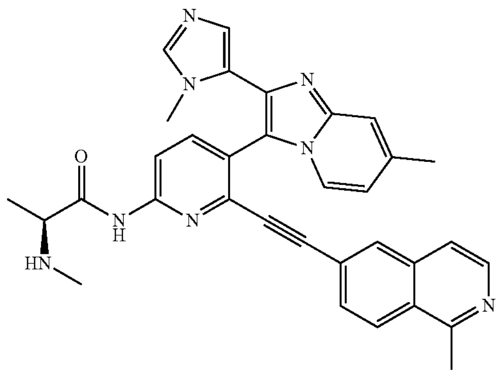 [SMILES: CN[C@@H](C)C(=O)Nc1ccc(-c2c(-c3cncn3C)nc3cc(C)ccn23)c(C#Cc2ccc3c(C)nccc3c2)n1]

TABLE 2-continued
15
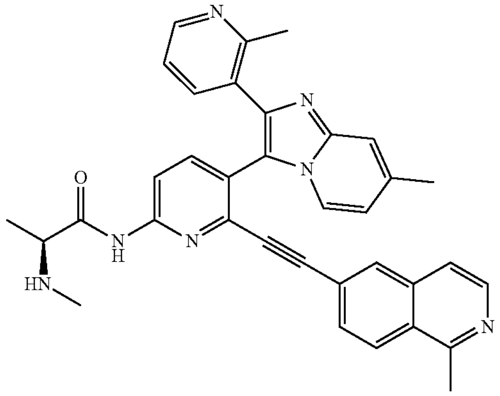 [SMILES: CN[C@@H](C)C(=O)Nc1ccc(-c2c(-c3cccnc3C)nc3cc(C)ccn23)c(C#Cc2ccc3c(C)nccc3c2)n1]
16
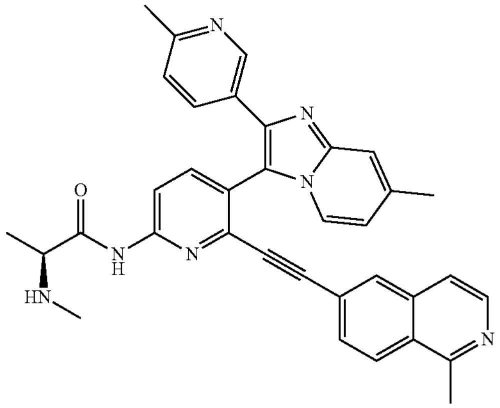 [SMILES: CN[C@@H](C)C(=O)Nc1ccc(-c2c(-c3ccc(C)nc3)nc3cc(C)ccn23)c(C#Cc2ccc3c(C)nccc3c2)n1]
17
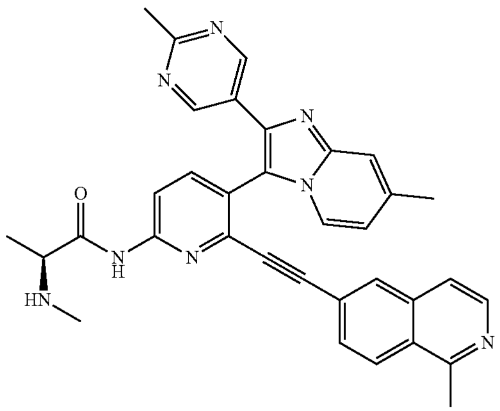 [SMILES: CN[C@@H](C)C(=O)Nc1ccc(-c2c(-c3cnc(C)nc3)nc3cc(C)ccn23)c(C#Cc2ccc3c(C)nccc3c2)n1]
18
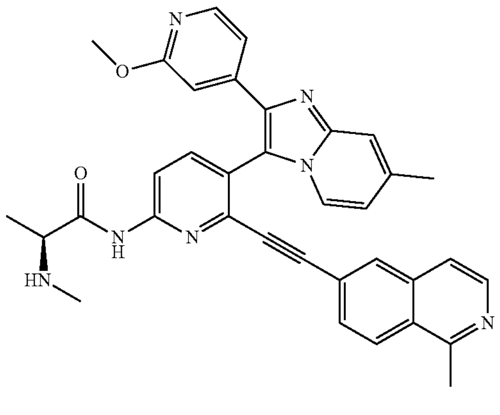 [SMILES: CN[C@@H](C)C(=O)Nc1ccc(-c2c(-c3ccnc(OC)c3)nc3cc(C)ccn23)c(C#Cc2ccc3c(C)nccc3c2)n1]
TABLE 2-continued
19
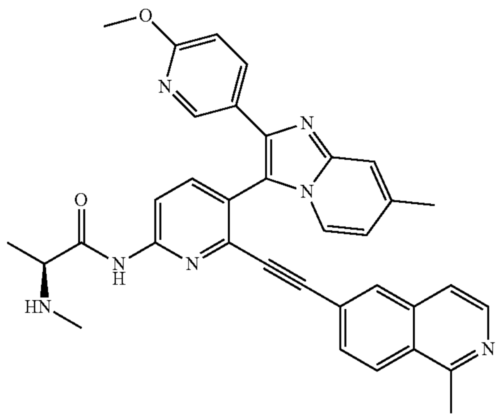 [SMILES: CN[C@@H](C)C(=O)Nc1ccc(-c2c(-c3ccc(OC)nc3)nc3cc(C)ccn23)c(C#Cc2ccc3c(C)nccc3c2)n1]
20
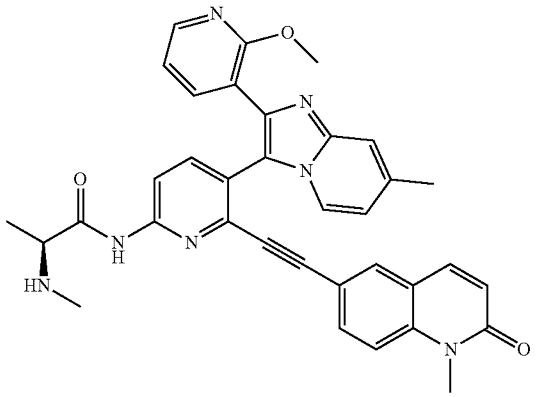 [SMILES: CN[C@@H](C)C(=O)Nc1ccc(-c2c(-c3cccnc3OC)nc3cc(C)ccn23)c(C#Cc2ccc3c(ccc(=O)n3C)c2)n1]
21
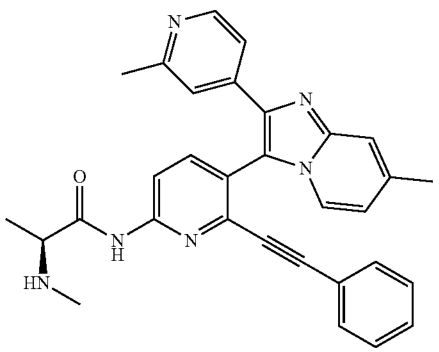 [SMILES: CN[C@@H](C)C(=O)Nc1ccc(-c2c(-c3ccnc(C)c3)nc3cc(C)ccn23)c(C#Cc2ccccc2)n1]
22
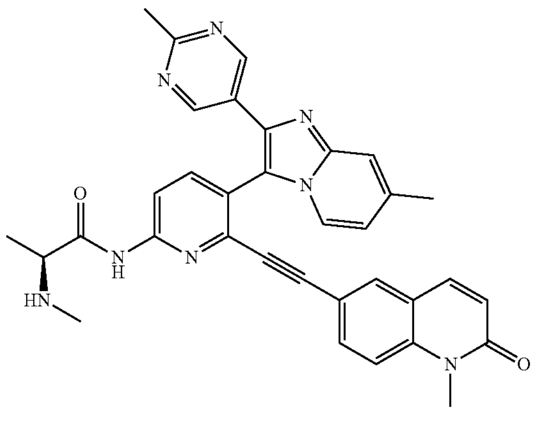 [SMILES: CN[C@@H](C)C(=O)Nc1ccc(-c2c(-c3cnc(C)nc3)nc3cc(C)ccn23)c(C#Cc2ccc3c(ccc(=O)n3C)c2)n1]

TABLE 2-continued

23

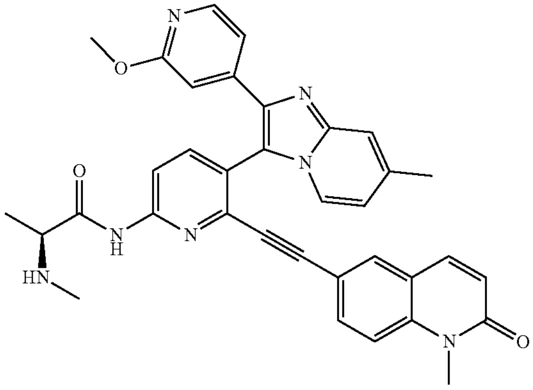 [SMILES: CN[C@@H](C)C(=O)Nc1ccc(-c2c(-c3ccnc(OC)c3)nc3cc(C)ccn23)c(C#Cc2ccc3c(ccc(=O)n3C)c2)n1]

24

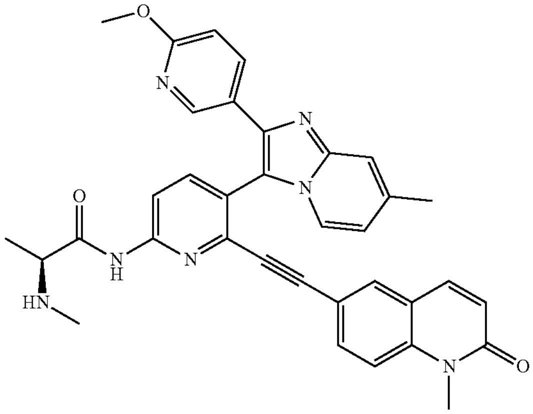 [SMILES: CN[C@@H](C)C(=O)Nc1ccc(-c2c(-c3ccc(OC)nc3)nc3cc(C)ccn23)c(C#Cc2ccc3c(ccc(=O)n3C)c2)n1]

25

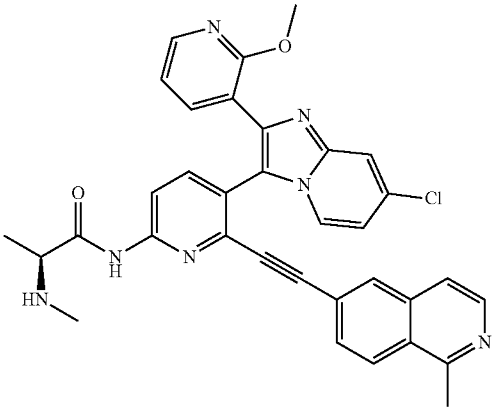 [SMILES: CN[C@@H](C)C(=O)Nc1ccc(-c2c(-c3cccnc3OC)nc3cc(Cl)ccn23)c(C#Cc2ccc3c(C)nccc3c2)n1]

26

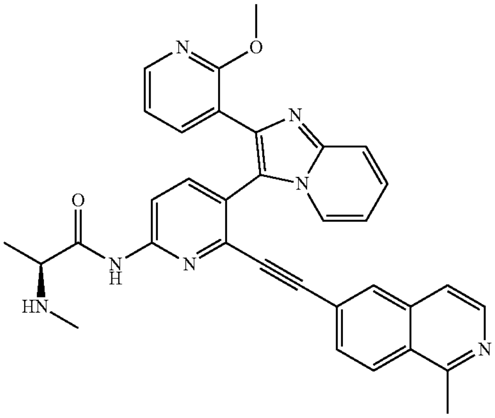 [SMILES: CN[C@@H](C)C(=O)Nc1ccc(-c2c(-c3cccnc3OC)nc3ccccn23)c(C#Cc2ccc3c(C)nccc3c2)n1]

Example compounds 1 to 10 in Table 2 are disclosed in WO 2013/127729. Example compounds 11 to 26 in Table 2 are disclosed in WO 2016/023858.

The term “SMAC mimetic/IAP antagonist” as used herein also includes the SMAC mimetics listed above in the form of a tautomer, of a pharmaceutically acceptable salt, of a hydrate or of a solvate (including a hydrate or solvate of a pharmaceutically acceptable salt). It also includes the SMAC mimetic in all its solid, preferably crystalline, forms and in all the crystalline forms of its pharmaceutically acceptable salts, hydrates and solvates (including hydrates and solvates of pharmaceutically acceptable salts).

All SMAC mimetics listed above are known in the art with the respective synthesis and properties. All patent applications referred to above are incorporated by reference in their entirety.

In one embodiment the SMAC mimetic is LCL161 or a pharmaceutically acceptable salt thereof (A1).

In another embodiment the SMAC mimetic is compound 1 in table 2 or a pharmaceutically acceptable salt thereof (A2).

In another embodiment the SMAC mimetic is compound 2 in table 2 or a pharmaceutically acceptable salt thereof (A3).

In another embodiment the SMAC mimetic is compound 3 in table 2 or a pharmaceutically acceptable salt thereof (A4).

In another embodiment the SMAC mimetic is compound 4 in table 2 or a pharmaceutically acceptable salt thereof (A5).

In another embodiment the SMAC mimetic is compound 5 in table 2 or a pharmaceutically acceptable salt thereof (A6).

In another embodiment the SMAC mimetic is compound 6 in table 2 or a pharmaceutically acceptable salt thereof (A7).

In another embodiment the SMAC mimetic is compound 7 in table 2 or a pharmaceutically acceptable salt thereof (A8).

In another embodiment the SMAC mimetic is compound 8 in table 2 or a pharmaceutically acceptable salt thereof (A9).

In another embodiment the SMAC mimetic is compound 9 in table 2 or a pharmaceutically acceptable salt thereof (A10).

In another embodiment the SMAC mimetic is compound 10 in table 2 or a pharmaceutically acceptable salt thereof (A11).

In another embodiment the SMAC mimetic is compound 11 in table 2 or a pharmaceutically acceptable salt thereof (A12).

In another embodiment the SMAC mimetic is compound 12 in table 2 or a pharmaceutically acceptable salt thereof (A13).

In another embodiment the SMAC mimetic is compound 13 in table 2 or a pharmaceutically acceptable salt thereof (A14).

In another embodiment the SMAC mimetic is compound 14 in table 2 or a pharmaceutically acceptable salt thereof (A15).

In another embodiment the SMAC mimetic is compound 15 in table 2 or a pharmaceutically acceptable salt thereof (A16).

In another embodiment the SMAC mimetic is compound 16 in table 2 or a pharmaceutically acceptable salt thereof (A17).

In another embodiment the SMAC mimetic is compound 17 in table 2 or a pharmaceutically acceptable salt thereof (A18).

In another embodiment the SMAC mimetic is compound 18 in table 2 or a pharmaceutically acceptable salt thereof (A19).

In another embodiment the SMAC mimetic is compound 19 in table 2 or a pharmaceutically acceptable salt thereof (A20).

In another embodiment the SMAC mimetic is compound 20 in table 2 or a pharmaceutically acceptable salt thereof (A21).

In another embodiment the SMAC mimetic is compound 21 in table 2 or a pharmaceutically acceptable salt thereof (A22).

In another embodiment the SMAC mimetic is compound 22 in table 2 or a pharmaceutically acceptable salt thereof (A23).

In another embodiment the SMAC mimetic is compound 23 in table 2 or a pharmaceutically acceptable salt thereof (A24).

In another embodiment the SMAC mimetic is compound 24 in table 2 or a pharmaceutically acceptable salt thereof (A25).

In another embodiment the SMAC mimetic is compound 25 in table 2 or a pharmaceutically acceptable salt thereof (A26).

In another embodiment the SMAC mimetic is compound 26 in table 2 or a pharmaceutically acceptable salt thereof (A27).

All embodiments (A1) to (A27) are preferred embodiments of embodiment (A0) in respect of the nature of the SMAC mimetic.

In a preferred embodiment relating to the combination treatments the recombinant rhabdovirus is a recombinant vesicular stomatitis virus encoding in its genome at least one CD80 extracellular domain Fc-fusion protein or a functional variant thereof, preferably human CD80 extracellular domain, selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a further preferred embodiment relating to the combination treatment the recombinant rhabdovirus is a recombinant vesicular stomatitis virus encoding in its genome a vesicular stomatitis virus nucleoprotein (N), large protein (L), phosphoprotein (P), matrix protein (M), glycoprotein (G) and at least one CD80 extracellular domain Fc-fusion protein or a functional variant thereof, preferably human CD80 extracellular domain, wherein the CD80 extracellular domain Fc-fusion protein or functional variant thereof is selected from the group comprising: (i) a CD80 extracellular domain Fc-fusion protein, comprising a CD80 extracellular domain fused to the Fc domain of an IgG1, (ii) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1, (iii) a CD80 extracellular domain Fc-fusion protein, comprising a CD80 extracellular domain fused to the Fc domain of an IgG1, wherein the Fc domain comprises or consists of SEQ ID NO:2 or has at least 80% identity to SEQ ID NO:2, (iv) a CD80 extracellular domain Fc-fusion protein, comprising a CD80 extracellular domain fused to the Fc domain of an IgG1, wherein the CD80 extracellular domain comprises or consists of SEQ ID NO:1 or has at least 80% identity to SEQ ID NO:1 and the Fc domain comprises or consists of SEQ ID NO:2 or has at least 80% identity to SEQ ID NO:2, (v) a CD80 extracellular domain Fc-fusion protein, comprising a CD80 extracellular domain fused to the Fc domain of an IgG1, wherein the CD80 extracellular domain consists of amino acids 1-207 of SEQ ID NO:4 or has at least 80% identity to amino acids 1-207 of SEQ ID NO:4 and the Fc domain consists of amino acids 208-433 of SEQ ID NO:4 or has at least 80% identity to amino acids 208-433 of SEQ ID NO:4, (vi) a CD80 extracellular domain Fc-fusion protein according to any of (i)-(v) further comprising a signal peptide sequence, or (vii) a CD80 extracellular domain Fc-fusion protein, comprising SEQ ID NO:3 or having at least 80% identity to SEQ ID NO:3, wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a more preferred embodiment relating to the combination treatments the recombinant rhabdovirus is a recombinant vesicular stomatitis virus encoding in its genome at least one CD80 extracellular domain Fc-fusion protein or a functional variant thereof, preferably human CD80 extracellular domain, wherein the CD80 extracellular domain Fc-fusion protein or functional variant thereof comprises or consists of SEQ ID NO:3 or has at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

Virus Generation, Production and Virus Producing Cell

The invention also provides a virus producing cell, characterized in that the cell produces a recombinant rhabdovirus or recombinant vesicular stomatitis virus according to the invention.

The cell may be of any origin and may be present as isolated cell or as a cell comprised in a cell population. It is preferred that the cell producing a recombinant rhabdovirus or recombinant vesicular stomatitis virus is a mammalian cell. In a more preferred embodiment, the virus producing cell of the invention is characterized in that the mammalian cell is a multipotent adult progenitor cell (MAPC), a neural stem cell (NSC), a mesenchymal stem cell (MSC), a HeLa cell, a HEK cell, any HEK293 cell (e.g. HEK293F or HEK293T), a Chinese hamster ovary cell (CHO), a baby hamster kidney (BHK) cell or a Vero cell or a bone marrow derived tumor infiltrating cell (BM-TIC).

Alternatively, the virus producing cell may be a human cell, monkey cell, mouse cell or hamster cell. The skilled person is aware of methods suitable for use in testing whether a given cell produces a virus and, thus, whether a particular cell falls within the scope of this invention. In this respect, the amount of virus produced by the cell of the invention is not particularly limited. Preferred viral titers are $\geq 1\times10^7$ TCID50/ ml or $\geq 1\times10^8$ genome copies/ml in the crude supernatants of the given cell culture after infection without further downstream processing.

In a particular embodiment, the virus producing cell of the invention is characterized in that the cell comprises one or more expression cassettes for the expression of at least one of the genes selected from the group consisting of genes n, I, p and m coding for proteins N, L, P and M of the VSV and a gene gp coding for LCMV-GP, Dandenong-GP or Mopeia-GP glycoprotein.

Virus producing cells in the meaning of the invention include classical packaging cells for the production of recombinant rhabdovirus from non-replicable vectors as well as producer cells for the production of recombinant rhabdovirus from vectors capable of reproduction. Packaging cells usually comprise one or more plasmids for the expression of essential genes which lack in the respective vector to be packaged and/or are necessary for the production of virus. Such cells are known to the skilled person who can select appropriate cell lines suitable for the desired purpose.

Recombinant rhabdovirus of the invention can be produced according to methods known to the skilled artisan and include without limitation (1) using cDNAs transfected into a cell or (2) a combination of cDNAs transfected into a helper cell, or (3) cDNAs transfected into a cell, which is further infected with a helper/minivirus providing in trans the remaining components or activities needed to produce either an infectious or non-infectious recombinant rhabdovirus. Using any of these methods (e.g., helper/minivirus, helper cell line, or cDNA transfection only), the minimum components required are a DNA molecule containing the cis-acting signals for (1) encapsidation of the genomic (or antigenomic) RNA by the Rhabdovirus N protein, P protein and L protein and (2) replication of a genomic or antigenomic (replicative intermediate) RNA equivalent.

A replicating element or replicon is a strand of RNA minimally containing at the 5' and 3' ends the leader sequence and the trailer sequence of a rhabdovirus. In the genomic sense, the leader is at the 3' end and the trailer is at the 5' end. Any RNA-placed between these two replication signals will in turn be replicated. The leader and trailer regions further must contain the minimal cis-acting elements for purposes of encapsidation by the N protein and for polymerase binding which are necessary to initiate transcription and replication. For preparing recombinant rhabdovirus a minivirus containing the G gene would also contain a leader region, a trailer region and a G gene with the appropriate initiation and termination signals for producing a G protein mRNA. If the minivirus further comprises an M gene, the appropriate initiation and termination signals for producing the M protein mRNA must also present.

For any gene contained within the recombinant rhabdovirus genome, the gene would be flanked by the appropriate transcription initiation and termination signals which will allow expression of those genes and production of the protein products (Schnell et al., Journal of Virology, p. 2318-2323, 1996). To produce "non-infectious" recombinant rhabdovirus, the recombinant rhabdovirus must have the minimal replicon elements and the N, P, and L proteins and it must contain the M gene. This produces virus particles that are budded from the cell but are non-infectious particles. To produce "infectious" particles, the virus particles must additionally comprise proteins that can mediate virus particle binding and fusion, such as through the use of an attachment protein or receptor ligand. The native receptor ligand of rhabdoviruses is the G protein.

Any cell that would permit assembly of the recombinant rhabdovirus can be used. One method to prepare infectious virus particles comprises an appropriate cell line infected with a plasmid encoding for a T7 RNA polymerase or other suitable bacteriophage polymerase such as the T3 or SP6 polymerases. The cells may then be transfected with individual cDNA containing the genes encoding the G, N, P, L and M rhabdovirus proteins. These cDNAs will provide the proteins for building a recombinant rhabdovirus particle. Cells can be transfected by any method known in the art.

Also transfected into the cell line is a "polycistronic cDNA" containing the rhabdovirus genomic RNA equivalent. If the infectious, recombinant rhabdovirus particle is intended to be lytic in an infected cell, then the genes encoding for the N, P, M and L proteins must be present as well as any heterologous nucleic acid segment. If the infectious, recombinant rhabdovirus particle is not intended to be lytic, then the gene encoding the M protein is not included in the polycistronic DNA. By "polycistronic cDNA" it is meant a cDNA comprising at least transcription units containing the genes which encode the N, P and L proteins. The recombinant rhabdovirus polycistronic DNA may also contain a gene encoding a protein variant or polypeptide fragment thereof, or a therapeutic nucleic acid or protein. Alternatively, any protein to be initially associated with the viral particle first produced or fragment thereof may be supplied in trans.

Also contemplated is a polycistronic cDNA comprising a gene encoding for a CD80 extracellular domain Fc-fusion protein. The polycistronic cDNA contemplated may contain a gene encoding a protein variant, a gene encoding a reporter, a therapeutic nucleic acid, and/or either the N-P-L genes or the N-P-L-M genes. The first step in generating a recombinant rhabdovirus is expression of an RNA that is a genomic or antigenomic equivalent from a cDNA. Then that RNA is packaged by the N protein and then replicated by the P/L proteins. The recombinant virus thus produced can be recovered. If the G protein is absent from the recombinant RNA genome, then it is typically supplied in trans. If both the G and the M proteins are absent, then both are supplied in trans. For preparing "non-infectious rhabdovirus" particles, the procedure may be the same as above, except that the polycistronic cDNA transfected into the cells would contain the N, P and L genes of the rhabdovirus only. The polycistronic cDNA of non-infectious rhabdovirus particles may additionally contain a gene encoding a protein.

Transfected cells are usually incubated for at least 24 hr at the desired temperature, usually about 37 degrees. For non-infectious virus particles, the supernatant is collected and the virus particles isolated. For infectious virus particles, the supernatant containing virus is harvested and transferred to fresh cells. The fresh cells are incubated for approximately 48 hours, and the supernatant is collected.

Other features and advantages of the present invention will become apparent from the following more detailed Examples which illustrate, by way of example, the principles of the invention.

EXAMPLES

Example 1

Generation of VSV-GP-huCD80-Fc (IgG1)—Viral Rescue

The genome of the oncolytic virus VSV-GP was engineered to encode for the CD80-Fc gene to locally express the CD80-Fc fusion protein at the tumor site during viral replication. Replication competent VSV-GP-CD80-Fc virus variants were generated by means of reverse genetics (cloning the gene of interest (GOI), virus rescue and repeated plaque purification) from bacterial plasmids that contain the cDNA for the complete viral genome of VSV-GP and human CD80-Fc. pVSV-GP-CD80-Fc plasmids were based on the plasmid pVSV-XN1 (Schnell et al.], which contains the complete cDNA genome of VSV Indiana serotype under the control of the T7 promoter. In order to generate pVSV-GP-CD80-Fc variants, the whole sequence for the VSV G envelope protein was substituted by the codon optimized sequence of GP envelope protein from Lymphocytic choriomeningitis virus (LCMV, WE-HPI strain). Additionally, a synthetic nucleic acid coding for a CD80-Fc gene was inserted between the glycoprotein GP and the viral polymerase L by Gibson assembly. Transcription of the CD80-Fc gene in the context of viral infection is ensured by an extra VSV start signal sequence at the 3' end and of an additional stop signal sequence at the 5' end of the CD80-Fc open reading frame.

Infectious viruses were recovered (or rescued) from the plasmid cDNAs by transfection of HEK293T or any other VSV permissive cell line by standard transfection methods (e.g. $CaPO_4$ precipitation, liposomal DNA delivery). Briefly, HEK293T cells were transfected with pSF-CAG-amp-based expression plasmids encoding the VSV proteins N, P, and L as well as a codon-optimized T7-polymerase. Additionally, the plasmid coding the viral genomic cDNA of VSV-GP, VSV-GP-CD80-Fc or a variant thereof was co-transfected. In a first step of the rescue process, the T7 polymerase transcribes the virus RNA genome from the plasmid coded virus cDNA. In a second step, VSV-L and -P proteins, which are exogenously expressed from the co-transfected plasmids, further amplify the viral RNA genomes. The viral RNA genomes are co-transcriptionally encapsulated by the VSV-N protein. Additionally, the P/L polymerase complex allows transcription of the full set of viral gene products N, P, M, GP and L as well as the inserted CD80-Fc variants. The viral RNA genomes are subsequently packaged into infectious VSV particles containing the ribonucleoprotein, the matrix protein and the viral envelope GP. Virus particles are released from the cells by budding.

Rescued viruses were initially passaged on permissive cell lines such as e.g. HEK293T. Several rounds of plaque purification were performed before generation of a virus seed stock by standard methods. Briefly, HEK293T cells were infected with serial ten-fold dilutions of the rescued pre-seeds. After approximately two hours, cell monolayers were washed twice and overlaid with media containing 0.8% of low melt agarose. 24 h to 48 h post infection, plaques were picked and virus was used for an additional round of plaque-purification or virus seed stocks were generated.

Example 2

Validation of Viral Fitness—$TCID_{50}$/Cell Killing

FIG. 3A-B

HEK293F cells grown in suspension culture (media Freestyle™ 293 Expression Medium (ThermoFisher Scientific)) were infected with a low MOI (0.0005) of either VSV-GP or VSV-GP-CD80-Fc. On the day of infection, the cells had a confluence of 60-70%. One well was counted (Countess™ cell counter, Invitrogen) before infecting the other wells with 0.005 MOI of one of the virus constructs VSV-GP (GP) or VSV-GP-CD80-Fc. Culture supernatants (3 mL total volume) were harvested and samples were analyzed 8 h, 16 h, 24 h, 32 h, 40 h and 48 h post infection for viral replication and cell killing. Viral replication was assessed using detection of viral genomes by qPCR in the supernatant of the cultures at the indicated timepoints (FIG. 3A). Virus induced cell killing was assessed by counting the viable cells in culture samples at the indicated time points (FIG. 3B). Both viruses behave the same way indicating that addition of the human CD80-Fc transgene does not affect the viral fitness.

Example 3

Cargo Expression—ELISA

FIG. 4

Supernatants from VSV-GP-CD80-Fc infected HEK293 cells were analyzed at different time points following viral infection using an ELISA. Expression of the virally encoded CD80-Fc fusion protein by infected, mammalian cells was validated by infecting HEK293 cells with the parental virus VSV-GP or the CD80-Fc encoding, new virus VSV-GP-CD80-Fc, both at an MOI1. Expression of the CD80-Fc transgene, as measured by ELISA in tissue culture supernatants, was readily detectable at 24, 31 and 48 hours post infection of the cells.

Example 4

VSV-GP-huCD80-Fc (In Vivo)—CT26. CL25-IFNARKO Tumor Model (High Cargo Expression)

FIG. 5A-B

Using the CT26. CL25-IFARKO tumor model, which has been engineered to lack the interferon alpha receptor (IFNAR), to better reflect the human patient situation and allow for improved virus replication as well as cargo expression in the murine system, the parental virus VSV-GP and the CD80-Fc encoding, new virus VSV-GP-CD80-Fc were compared back-to-back. For this purpose the two viruses were administered intravenously (i.v.) at a dose of $2\times10^7$ $TCID_{50}$ on day 0 and day 3 (survival graph) in mice with established tumors. As depicted in panel (A) the parental virus VSV-GP did not demonstrate a significantly improved survival of tumor bearing animals at this low viral dose, while treatment with the cargo-armed, new virus VSV-GP-CD80-Fc resulted in a pronounced survival benefit as compared to the control and VSV-GP treated animals. Furthermore, treatment with the CD80-Fc encoding virus did not result in an increased body weight loss as compared to the control and VSV-GP treated animals (B), arguing for the safety of this novel virus.

Example 5

VSV-GP-huCD80-Fc (In Vivo)—B16-F1-OVA & EMT-6 Tumor Models (Low Cargo Expression)

FIG. 6A-C and FIG. 7A-B

The lowly permissive tumor models B16-F1-OVA (FIG. 6A-C) and EMT-6 (FIG. 7A-B), which only allow for minimal viral replication and accordingly cargo (CD80-Fc) expression were treated with two intra tumoral (i.t.) injections of the parental virus VSV-GP or the CD80-Fc encoding, new virus VSV-GP-CD80-Fc on day 0 and day 3. Only mice with well-established tumors were used for the injections. Treatment of the B16-F1-OVA tumor models with VSV-GP-CD80-Fc resulted in an improved tumor growth delay as compared to control and VSV-GP. In the EMT-6 tumor model treatment with VSV-GP-CD80-Fc resulted in an improved tumor clearance rate (33% of treated animals) as compared to control (0% of treated animals) and VSV-GP (8% of treated animals) treated mice. These results argue for an upside potential of the cargo-armed novel virus VSV-GP-CD80-Fc over the parental virus VSV-GP even in tumors with a low level of virus replication and cargo expression, which is intimately linked to the ability of the virus to replicate.

Example 6

In Vivo Viral Persistence & Replication as Well as Cargo Expression

FIG. 8-10

Figure 8:
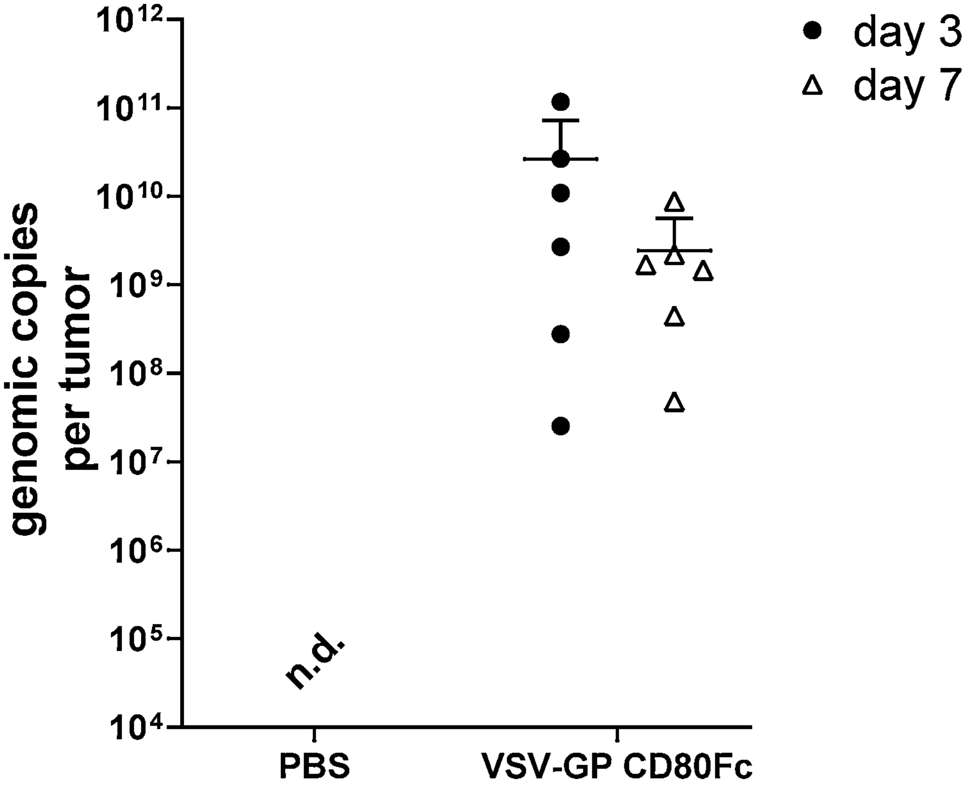
FIG. 8 VSV-GP-CD80-Fc replication within infected CT26. CL25-IFNARKO tumors taken from treated mice as determined by viral genome copy quantification using qPCR on day 3 & 7 post infection. Mice were treated either with PBS or $10^8$ $TCID_{50}$ VSV-GP-CD80-Fc and the viral genome copies per tumor (y-axis) were determined after 3 or 7 days respectively.
Figure 9:
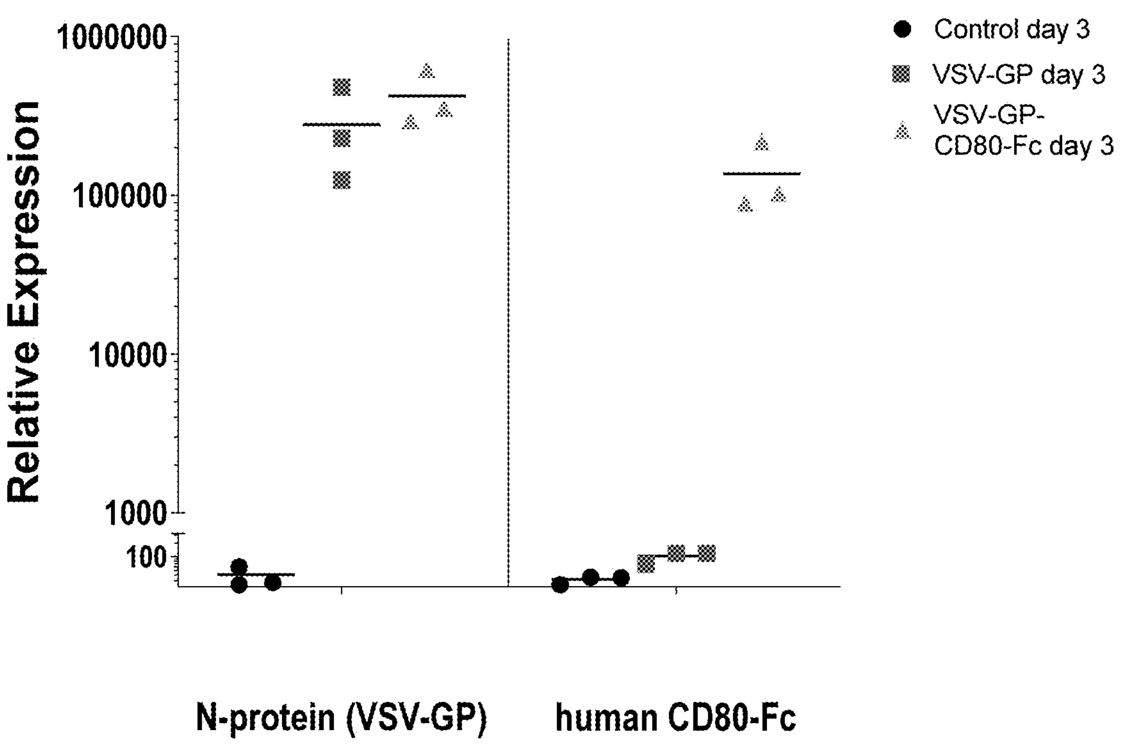
FIG. 9 NanoString-based measurement of VSV-GP N-protein as well as CD80-Fc transcripts in control, VSV-GP or VSV-GP-CD80-Fc infected LLC-IFNARKO tumors taken from treated mice. Mice were either used as control or treated with $10^8$ $TCID_{50}$ VSV-GP or VSV-GP-CD80-Fc and the relative expression of the viral N-protein or CD80-Fc (y-axis) were determined after 3 days.
Figure 10:
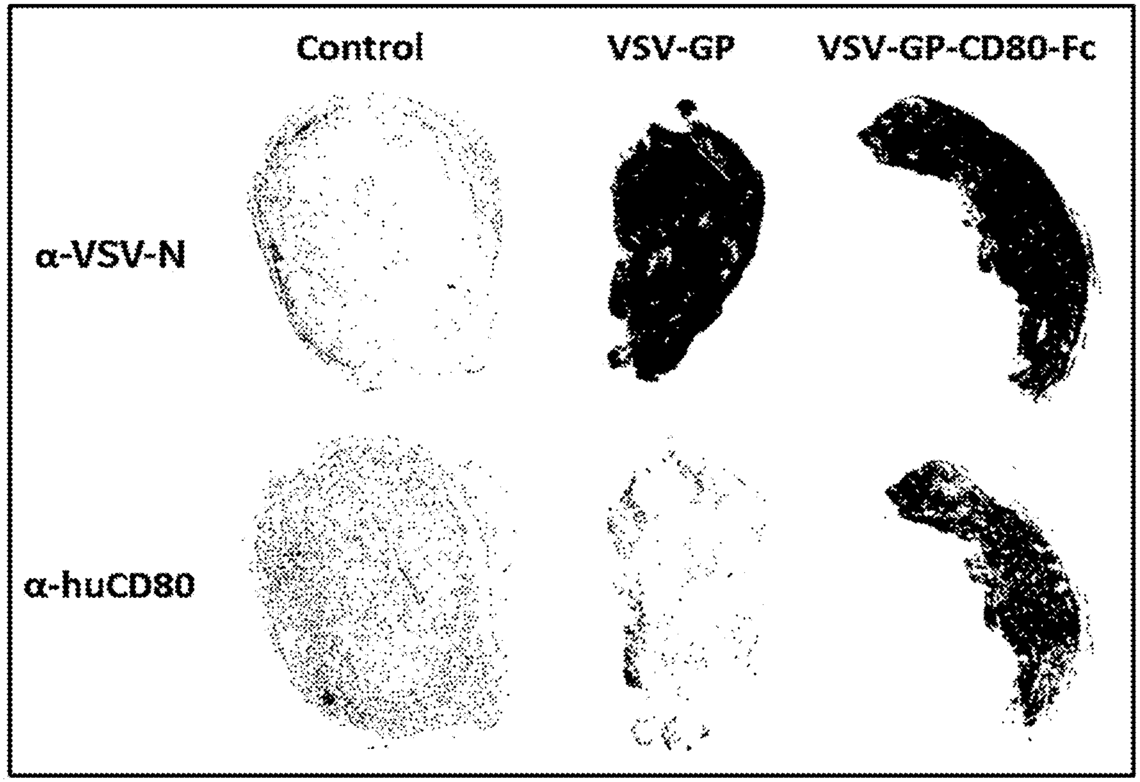
FIG. 10 IHC-based detection of the VSV-GP N-protein as well as CD80-Fc cargo (protein) in control, VSV-GP or VSV-GP-CD80-Fc infected LLC-IFNARKO tumors taken from treated mice. Mice were treated as in FIG. 9 and IHC was performed using standard protocols on day 3 post treatment.
Figure 11:
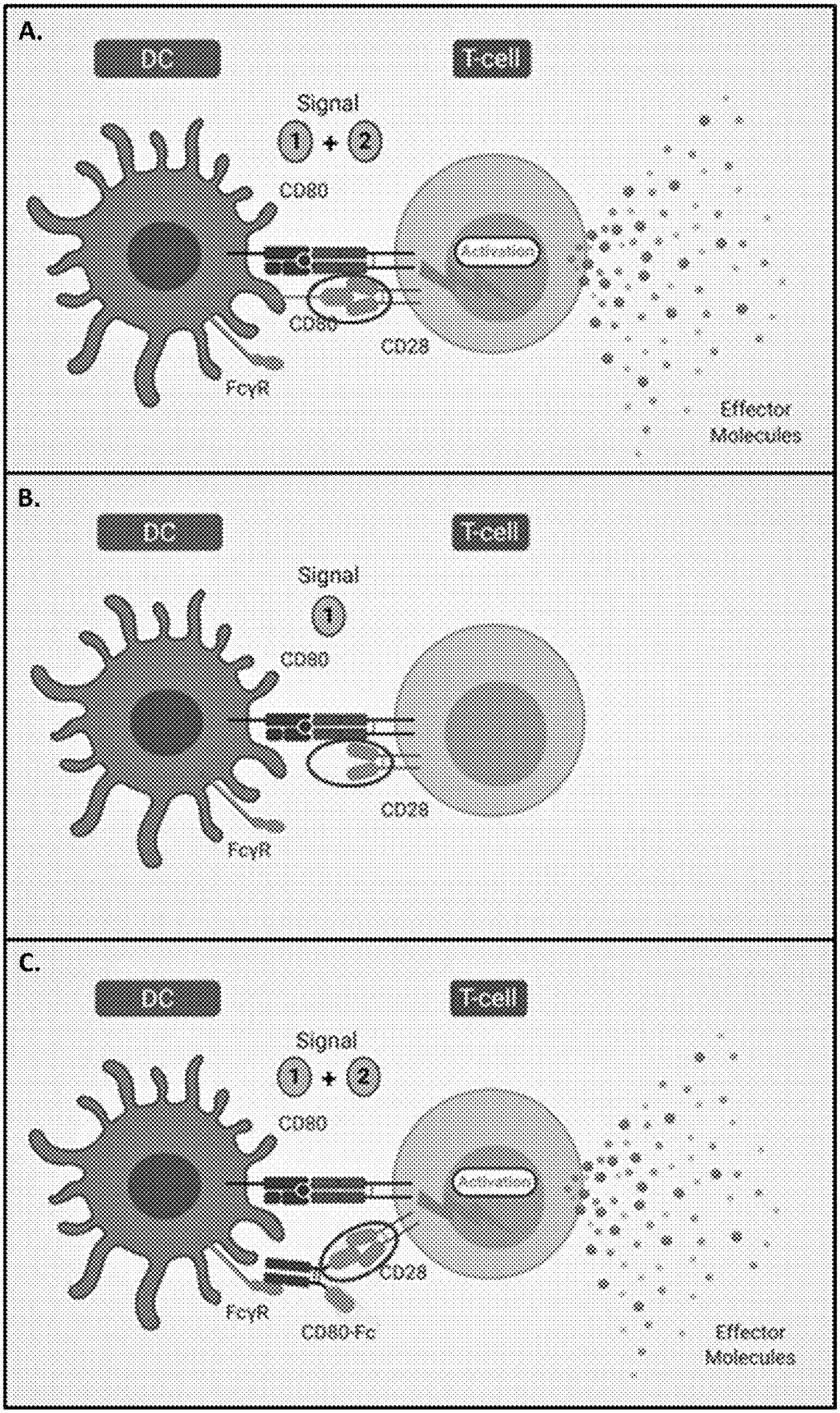
FIG. 11A-C Cartoon depicting CD80-Fc mode of action (MoA) in tumors. Hot tumors (A) with mature, activated DCs, which provide efficient T-cell co-stimulation. Cold tumors (B) lacking DCs and/or dominated by immature, tolerogenic DC subsets. The absence of DCs or immature tolerogenic DC subsets results in poor T-cell immunity, clonal anergy, T-cell dysfunction & cell death. CD80-Fc converting cold tumors into hot tumors (C) by compensating for the lack of potent T-cell co-stimulation.

Balb/c mice with established CT26. CL25-IFNARKO (CT26. CL25 tumor cells deleted for the interferon alpha receptor) tumors were used as controls or treated with a single i.v. injection of $1\times10^8$ $TCID_{50}$ of VSV-GP-CD80-Fc. Three and seven days post treatment tumors were resected; whole RNA was extracted and analyzed using qPCR primers specific for the VSV n gene (FIG. 8). C57BL/6 mice with established LLC1-IFNARKO (LLC1 tumor cells deleted for the interferon alpha receptor) tumors were used as controls or treated with a single i.v. injection of $1\times10^8$ $TCID_{50}$ of VSV-GP or VSV-GP-CD80-Fc. Three days post treatment, tumors were resected, and RNA analyzed using the "Pan Cancer Immune Profiling Panel" from NanoString, combined with virus and cargo specific probes (spike-in) according to the manufacturer's instructions (FIG. 9). Taken together the results show active replication of VSV-GP-CD80-Fc in treated animals and mRNA expression of the cargo in the tumor. Peak replication was observed around day three. The virus also persists up to day seven. C57BL/6 mice with established LLC1-IFNARKO tumors were used as controls or treated with a single i.v. injection of $1\times10^8$ $TCID_{50}$ of VSV-GP or VSV-GP-CD80-Fc. Three days post treatment, tumors were resected, formalin fixed and paraffin embedded. Thin sections were stained with specific antibodies to the VSV-N protein or the human CD80 protein (FIG. 10). N protein staining was similar for both VSV-GP and VSV-GP-CD80-Fc, while the human CD80 was specifically detected only for the latter.

Example 7

CD80-Fc Provides T-Cell Co-Stimulation in Human Mixed-Leukocyte Culture. FcγR Blockade Diminishes T-Cell Activation, Essential Role of Fc

FIG. 12 & FIG. 13A-D

Figure 12:
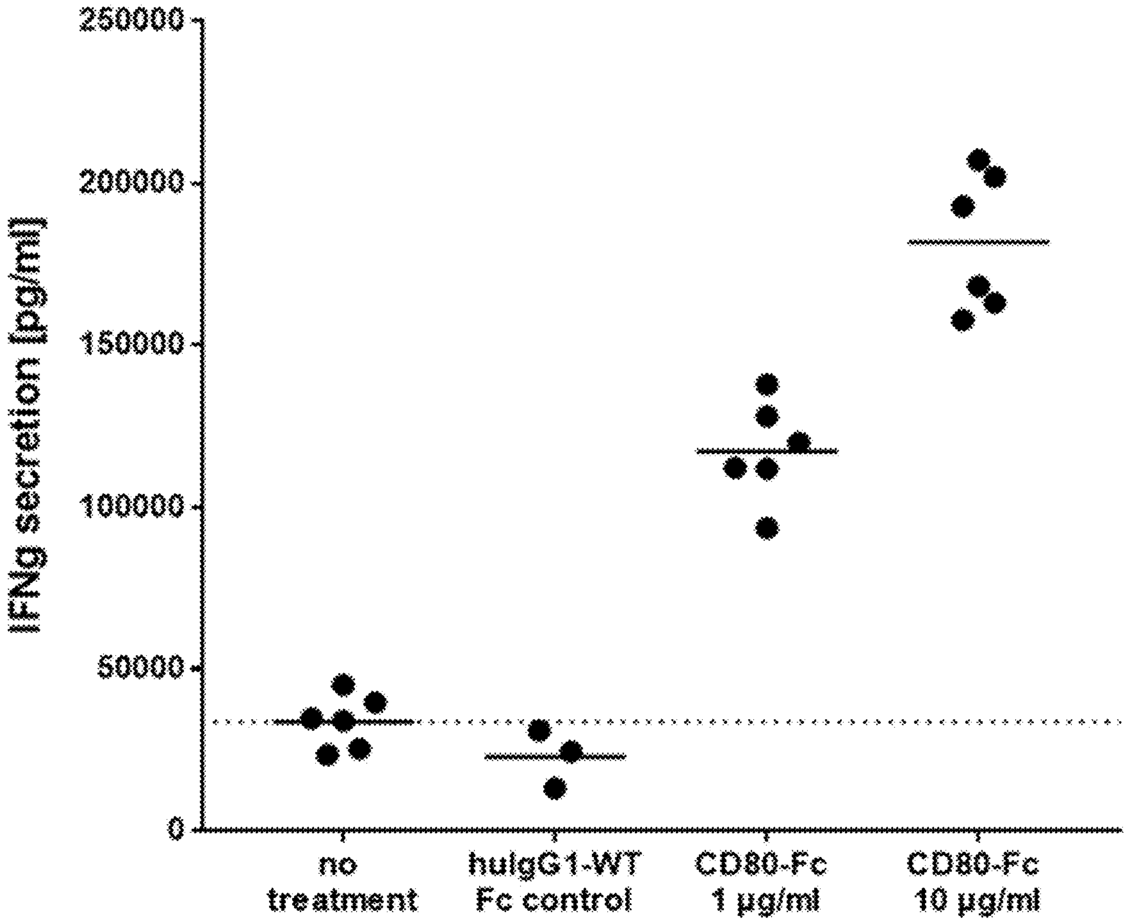
FIG. 12 A human Mixed-Leukocyte culture (T-cells and immature dendritic cells from two genetically different individuals are co-cultured resulting in allogenic T-cell stimulation) was used to evaluate T-cell co-stimulation by recombinant CD80-Fc. To this end cultures were stimulated with increasing amounts of a recombinant CD80-Fc protein using IFNγ secretion as readout.
Figure 15:
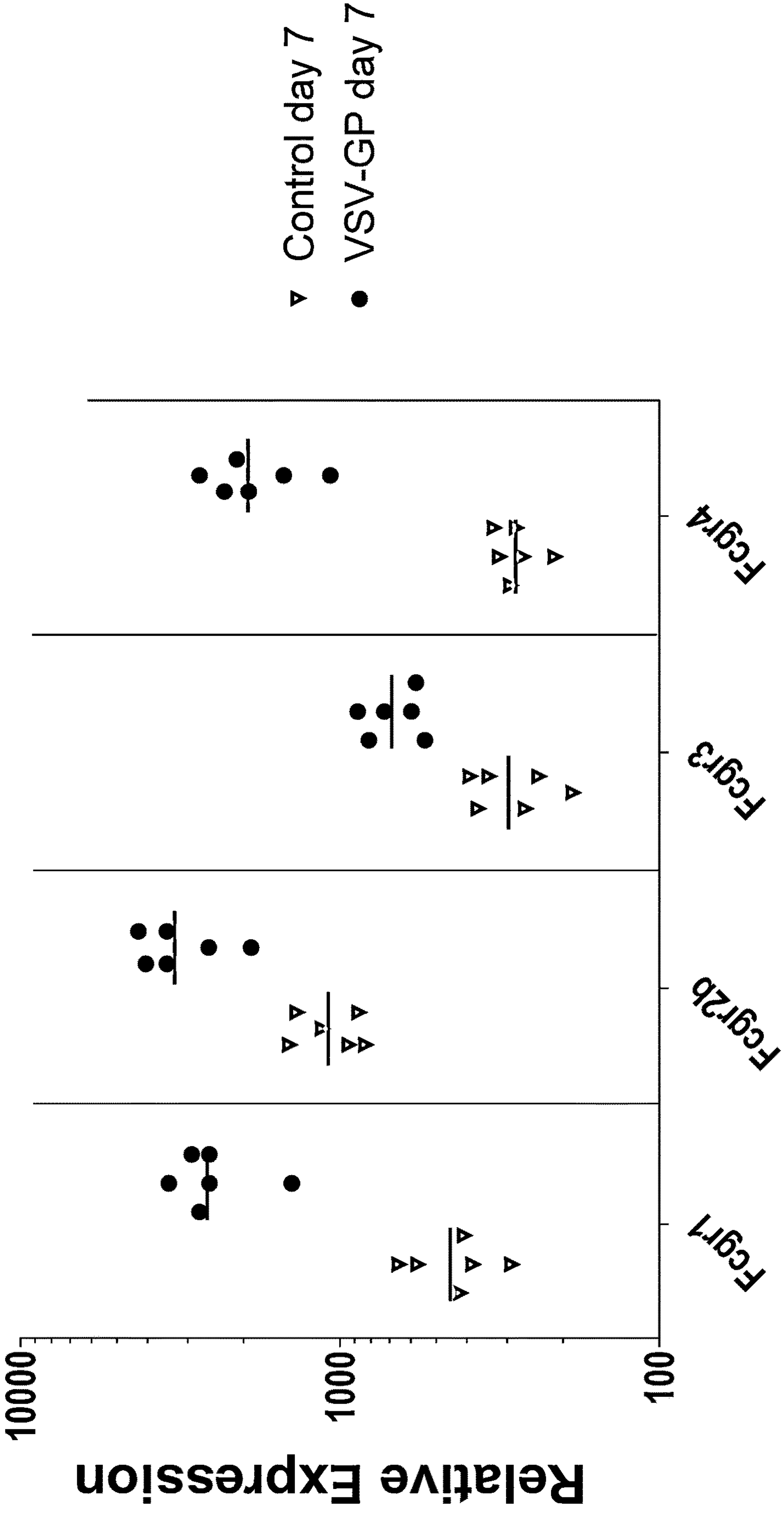
FIG. 15 NanoString-based measurement of FcγRs in control or VSV-GP infected LLC1-IFNARKO tumors at day 7 post infection. Mice were left either untreated or were infected with a viral dose of $10^8$ $TCID_{50}$ VSV-GP. X-axis shows the measurements for the different FcγRs (1, 2b, 3 or 4) and the Y-axis the relative expression after 7 days.
Figure 17:
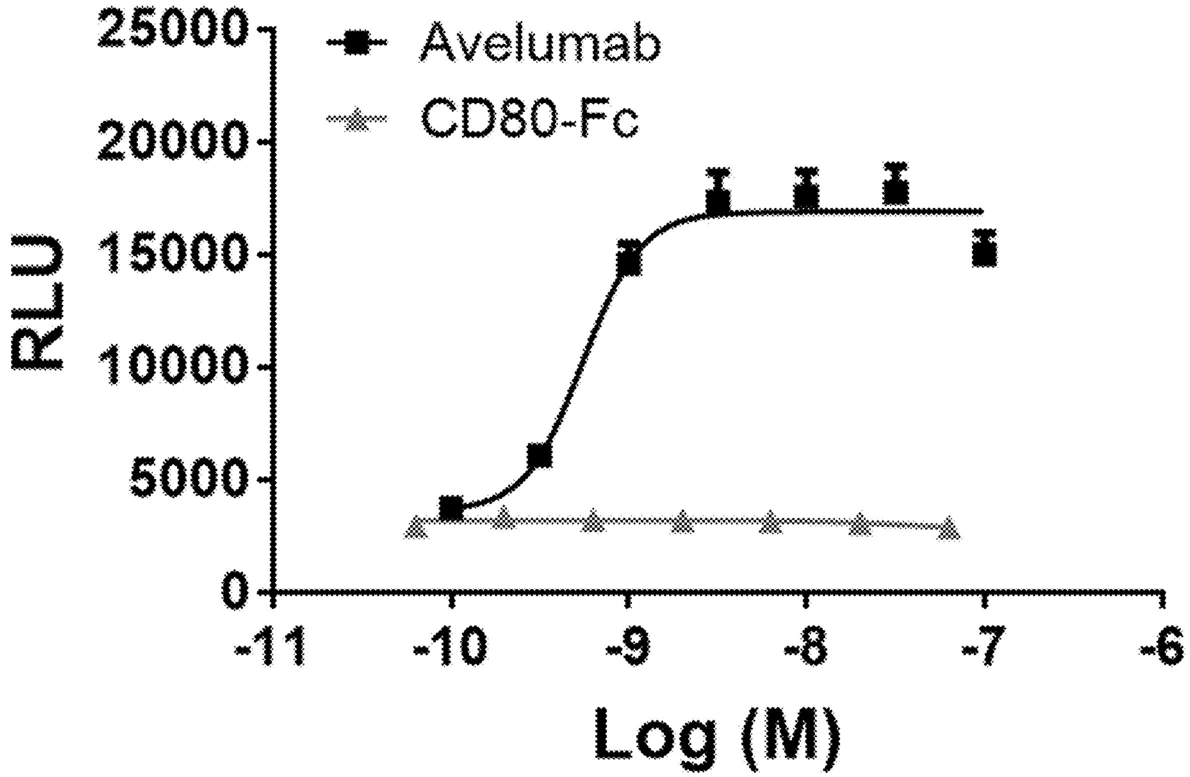
FIG. 17 Luminescence based readout: Co-culture Jurkat PD-1 reporter cells & CHO-K1-α-CD3/ -PDL1. CD80-Fc, as opposed to the anti-PDL1 antibody Avelumab, is not able to prevent PD1: PDL1-mediated suppression of the Jurkat reporter cell line.

A human Mixed-Leukocyte culture (selected leukocyte populations from two genetically different individuals are co-cultured resulting in allogenic T-cell stimulation) was used to evaluate the T-cell co-stimulatory potential of recombinant CD80-Fc (FIGS. 12&13) as well as the contribution of the wild type human IgG1 Fc for T-cell co-stimulation (FIG. 13). To this end cultures in FIG. 12 were stimulated with increasing amounts of recombinant CD80-Fc using IFNγ as readout. IFNγ secretion was strongly improved by addition of CD80-Fc to the cultures in a dose-dependent manner validating its T-cell co-stimulatory potential. Building on these data and aiming at elucidating the contribution of the Fc in the CD80-Fc fusion protein human Mixed-Leukocyte cultures were again stimulated with recombinant CD80-Fc protein (10 μg/ml) with or without the addition of FcγR-block (in the absence of human serum), using IFNγ as readout (FIG. 13). The different sub-figures (A-D) depict different donor pairs. CD80-Fc-mediated T-cell stimulation was strongly reduced by the addition of the FcγR-block, indicating that FcγR interaction and FcγR-mediated clustering is crucial for the activity of CD80-Fc.

Example 8

FcγR Dependence of T-Cell Activation by CD80-Fc in CD3 Activated PBMCs (F(ab)2 & IgG4)

FIG. 14A-F

Human PBMC cultures were stimulated with or without low doses of anti-CD3 (clone OKT3; 10 ng/ml) and increasing concentrations of recombinant CD80-Fc proteins using IFNγ (FIG. 14A-C) or IL2 (FIG. 14D-F) as readouts, which were detected by standard ELISA. To confirm the T-cell co-stimulatory potential of recombinant CD80-Fc as well as the contribution of the wild type human IgG1 Fc for T-cell co-stimulation and validate Fc-selection the following recombinant CD80-Fc variants were compared back-to-back: CD80-Fc (recombinant version of the viral cargo with wild type human IgG1 Fc, FIGS. 14C and F)); CD80 FAB (a $F(ab)_2$ variant of CD80-Fc, which lacks the Fc but retains bivalency, FIGS. 14A and D) and CD80 IgG4 (like CD80-Fc but with a human IgG4 Fc, FIGS. 14B and E). While CD80-Fc on its own did not significantly stimulate PBMCs the combination of CD80-Fc and the stimulating anti-CD3 antibody resulted in a dose dependent increase in T-cell stimulation as evidenced by IFNγ and IL2 secretion (FIGS. 14C and F). On the contrary the Fc-lacking $F(ab)_2$ variant of CD80-Fc was not active and did not result in an improved T-cell stimulation, neither alone, nor in combination with anti-CD3 stimulation (FIGS. 14A and D). The IgG4-based CD80 fusion (FIGS. 14B and E) displayed T-cell co-stimulatory potential, but to a much lower degree than the IgG1-based CD80 fusion construct (FIGS. 14B and F), which resembles the viral cargo engineered into the novel virus VSV-GP-CD80-Fc. These results again confirm the FcγR dependency of CD80-Fc as well as selection of the human IgG1 Fc. Furthermore, the lack of CD80-Fc activity without concomitant TCR stimulation argues for it favorable safety profile.

Example 9

VSV-GP Induces a Local Increase in FcγRs within Infected Tumors Supporting the CD80-Fc MoA

FIG. 15

Given the FcγR-dependency of the viral CD80-Fc cargo for T-cell co-stimulation the impact of VSV-GP infection on FcγR expression was explored in tumors. To this end NanoString-based measurements of FcγR expression in control or VSV-GP infected LLC1-IFNARKO tumors were performed at day 7 post infection. Mice were left either untreated or were infected with a viral dose of $10^8$ $TCID_{50}$ VSV-GP. X-axis shows the measurements for the different FcγRs (1, 2b, 3 or 4) and the Y-axis the relative expression. As the data clearly illustrate VSV-GP infected tumors unexpectedly display a strong upregulation of expression for all four analyzed FcγRs. These data provide a mechanistic basis for the favorable therapeutic interacting of the oncolytic virus VSV-GP and the FcγR-dependent, virally encoded cargo CD80-Fc, which benefits form the virus mediated FcγR upregulation within infected tumors.

Example 10

VSV-GP-CD80-Fc Induces Superior Tumor-Specific T-Cell Immunity as Compared to the Parental Virus VSV-GP

FIG. 16A-C

The impact of the virally encoded CD80-Fc cargo on tumor-antigen specific T-cell immunity was elucidated using the CT26. CL25-IFNARKO tumor model, which was treated with either the parental virus VSV-GP or the new virus VSV-GP-CD80-Fc. Gp70/ tumor specific T-cells were detected in spleen and blood of mice treated as depicted in FIG. 16C by ELISPOT (FIG. 16A) and FACS-based Dextramer staining (FIG. 16B) respectively. The significant increase in the frequency of tumor-antigen specific T-cells in the VSV-GP-CD80-Fc group vs. the VSV-GP group illustrates the upside potential of the novel, cargo-armed virus vs. the parental virus and furthermore provides an immunological/mechanistic basis for the improved anti-tumor activity of the novel oncolytic virus VSV-GP-CD80-Fc.

Example 11

CD80-Fc does not Interact with PD-L1

FIG. 17

It has been claimed that CD80 may be able to directly interact with Programmed cell death 1 ligand 1 (PD-L1), thereby blocking the inhibitory interaction of PD-L1 with it's receptor Programmed cell death 1 (PD-1) on activated T-cells. To determine whether the CD80-Fc fusion protein encoded in VSV-GP-CD80-Fc does directly interact with PD-L1 we performed a binding study on CHO-K1 cells stable transfected with human PD-L1. The PD-L1 specific antibody Avelumab was used as a positive control. While Avelumab readily bound to PD-L1 on the surface of the CHO-K1-PD-L1 cells the recombinant CD80-Fc protein failed to bind PD-L1 at all tested dose levels. It was therefore concluded that CD80-Fc does not directly bind to PD-L1.

Example 12

α-PD-1 and CD80-Fc Improve T-Cell Stimulation in an Additive Manner

FIG. 18A-B

To address the question whether CD80-Fc-mediated T-cell co-stimulation combined with antibody-mediated PD-1 inhibition is able to provide an additional benefit vs. the monotherapy treatments we employed a T-cell reporter system, where stably PD-1 expressing Jurkat T-cells do respond to T-cell receptor (TCR) stimulation by upregulating a luciferase activity, which is biochemically detectable. Here Jurkat-PD-1 reporter cells were co-cultured with FcγR positive THP1-PD-L1 cells (as opposed to the FcγR negative CHO-K1 cells), stably expressing PD-L1. The interaction of PD-L1 and PD-1 result in inhibition of Jurkat T-cell activation, comparable to the T-cell inhibition, which is observed in cancer patients. TCR stimulation is achieved by addition of a bi-specific BiTE molecule, which connects CD33 on the THP1 cells with CD3 on the Jurkat T-cells. As can be seen from FIG. 18A the PD-1 blocking antibody Pembrolizumab is able to restore CD3×CD33 BiTE-mediated T-cell stimulation in a dose-dependent manner by blocking the inhibitory PD-1: PD-L1 interaction. At the same time and quiet unexpected CD80-Fc on its own is able to provide T-cell co-stimulation and improve Jurkat T-cell activation in a dose-dependent manner despite the inhibitory PD-1: PD-L1 interaction. A Digitonin (Dig) specific antibody was used as isotype control. In FIG. 18B a fixed anti-PD-1 concentration (10 nM, in saturation) was combined with increasing concentrations of recombinant CD80-Fc. Addition of CD80-Fc on-top of the anti-PD-1 antibody resulted in superior T-cell activation providing clear evidence for the favorable interaction of these different therapeutic modalities, driven by their complementary mode of actions.

Example 13

VSV-GP-muCD80-Fc (In Vivo)—CT26. CL25-IFNARKO Tumor Model (High Cargo Expression)

FIG. 19A-C

Using again the CT26. CL25-IFNARKO tumor model, this study compares the in vivo efficacy of recombinant murine CD80Fc, VSV-GP or VSV-GP-muCD80Fc. For this purpose, mice with established tumors were treated i.v. on day 0 & 3 with a viral dose of $1\times10^8$ $TCID_{50}$ and on day 0, 3 and 6 with 1 mg/kg recombinant murine CD80-Fc, respectively.

As depicted in FIG. 19 panel (A) survival curves showed an improved therapeutic outcome in the VSV-GP-muCD80Fc treated groups. A significant survival benefit above recombinant CD80Fc protein or VSV-GP could be shown by $1\times10^8$ $TCID_{50}$ VSV-GP-muCD80Fc (Log-rank (Mantel-Cox) test; P value 0.0394).

The mean tumor sizes depicted in FIG. 19 panel (B) summarize single tumor growth curves and reflect a potent tumor-growth suppression after treatment with VSV-GP-muCD80Fc (dose $1\times10^8$ $TCID_{50}$) which outperformed VSV-GP as well as 1 mg/kg of recombinant CD80Fc protein by a far margin.

A drop in body weight was observed after first injection of both viruses (FIG. 19 panel (C)), however, recovery took place immediately, was not affected by the following injection of substances and did not significantly differ between the parental virus (VSV-GP) and the muCD80-Fc encoding virus (VSV-GP-muCD80Fc).

In summary, this study compared in particular the in vivo effects of recombinant murine CD80Fc or VSV-GP with VSV-GP-muCD80Fc. It was shown that by implementing muCD80Fc in the virus backbone a synergistic effect on tumor growth as well as overall survival was achieved.

The invention claimed is:

1. A method for the treatment of solid cancers comprising the administration of a pharmaceutical composition to a patient in need thereof, wherein said pharmaceutical composition comprises a recombinant vesicular stomatitis virus encoding in its genome at least one CD80 extracellular domain Fc-fusion protein, wherein the CD80 extracellular domain Fc-fusion protein comprises the extracellular domain of CD80 and the Fc domain of an IgG wherein the CD80 extracellular domain Fc-fusion protein comprises SEQ ID NO:4; and the gene coding for the wild-type glycoprotein G of the recombinant vesicular stomatitis virus is replaced by the gene coding for the glycoprotein G (GP) of Lymphocyte choriomeningitis virus (LCMV), and/or the wild-type glycoprotein G is replaced by the glycoprotein G (GP) of LCMV.

2. The method of claim 1, wherein the solid cancer is selected from the group consisting of: reproductive tumor, an ovarian tumor, a testicular tumor, an endocrine tumor, a gastrointestinal tumor, a pancreatic tumor, a liver tumor, a kidney tumor, a colon tumor, a colorectal tumor, a bladder tumor, a prostate tumor, a skin tumor, melanoma, a respiratory tumor, a lung tumor, a breast tumor, a head & neck tumor, a head and neck squamous-cell carcinoma (HNSCC) and a bone tumor.

3. The method of claim 1, wherein the pharmaceutical composition is administered intratumorally or intravenously.

4. The method of claim 3, wherein the pharmaceutical composition is administered at least once intratumorally and subsequently intravenously.

5. The method of claim 4, wherein the subsequent intravenous administration is given 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

6. The method according to claim 1, further comprising administering a PD-1 pathway inhibitor or a SMAC mimetic.

7. The method according to claim 6, wherein the PD-1 pathway inhibitor is an antagonistic antibody, which is directed against PD-1 or PD-L1.

8. The method according to claim 6, wherein the SMAC mimetic is selected from the group consisting of any one of compounds 1 to 26:

1

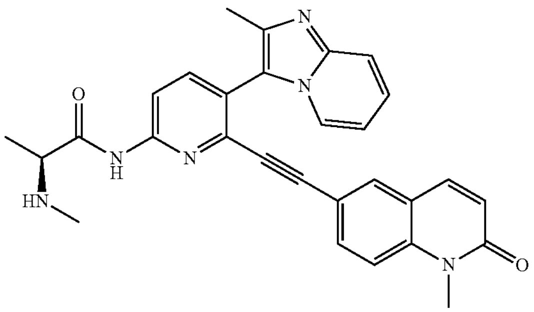

2

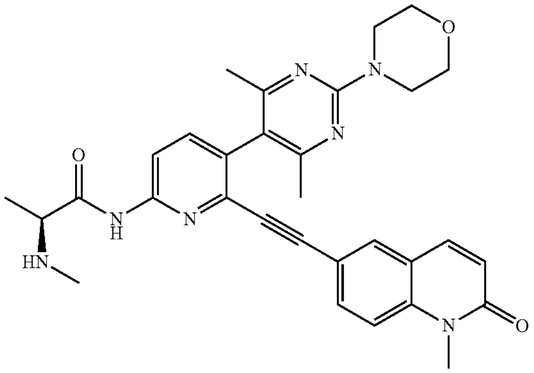

3

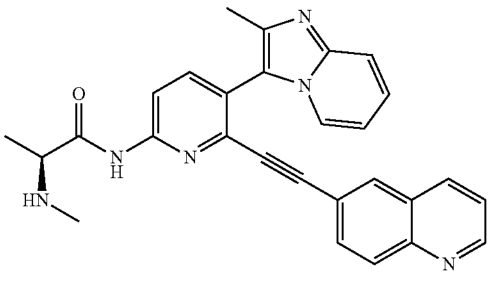

-continued
4
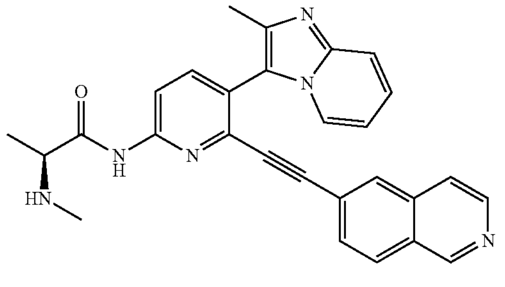
5
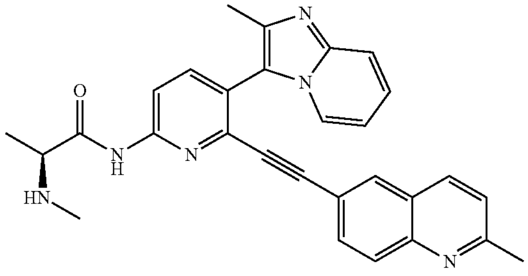
6
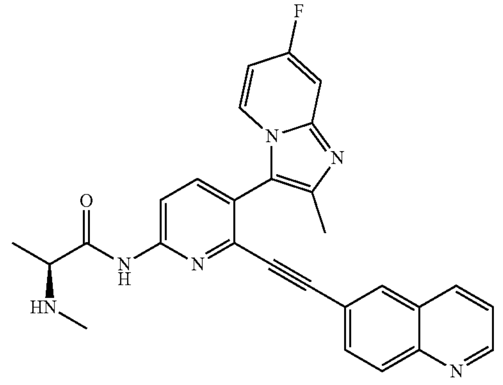
7
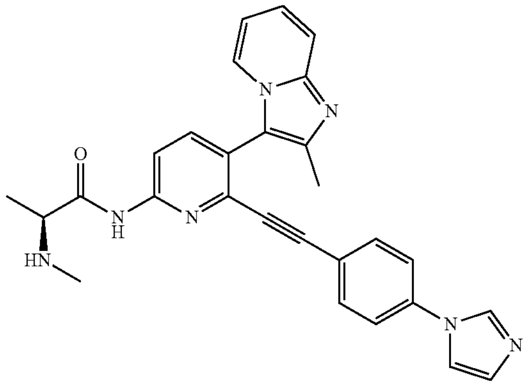
-continued
8
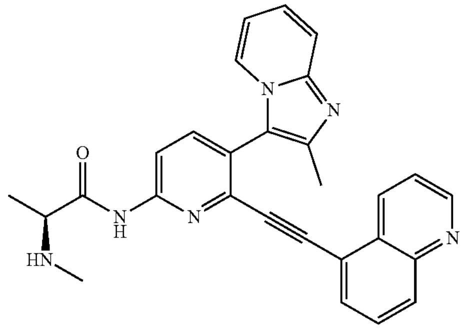
9
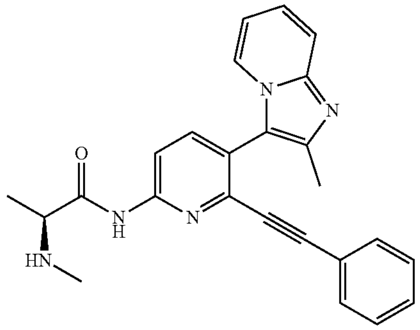
10
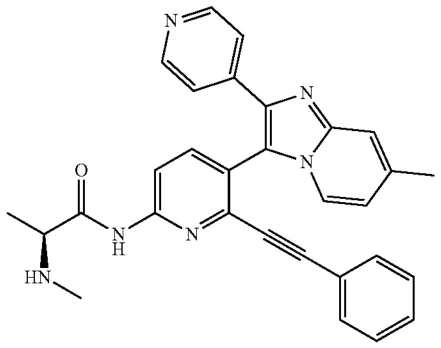
11
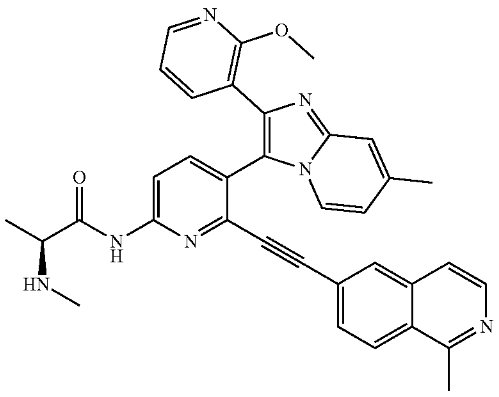

-continued
12
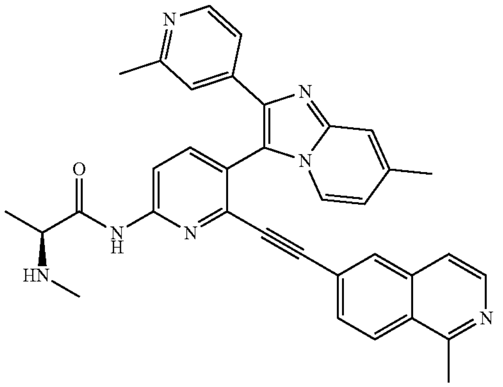
13
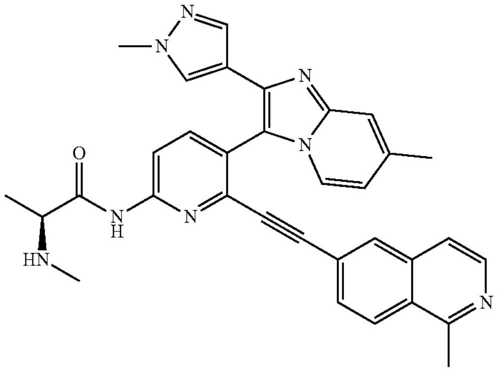
14
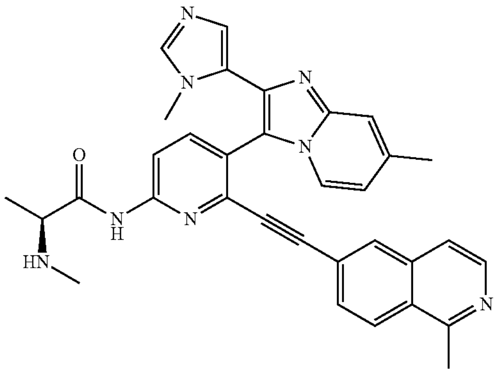
15
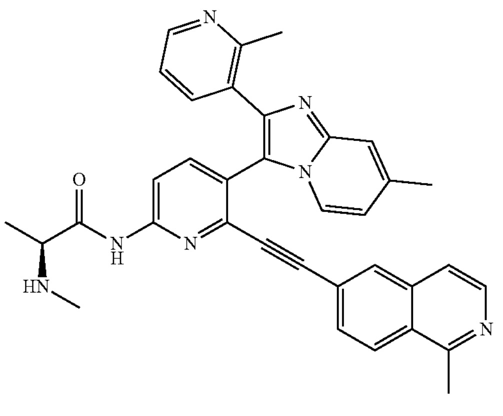
-continued
16
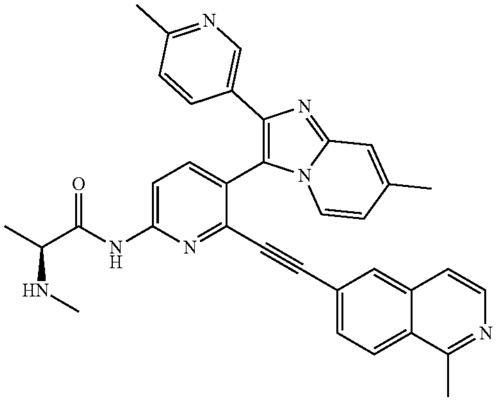
17
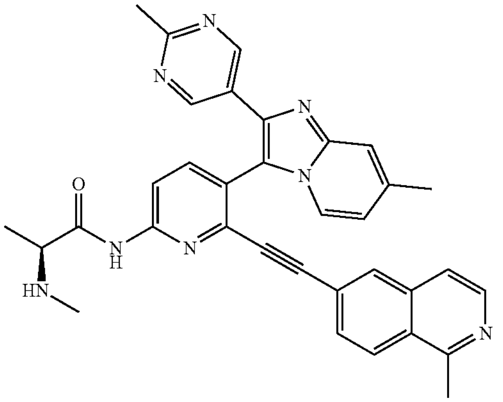
18
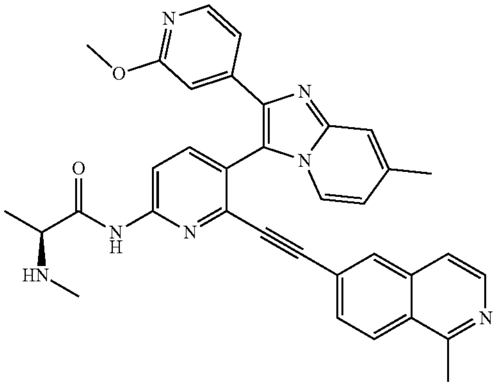
19
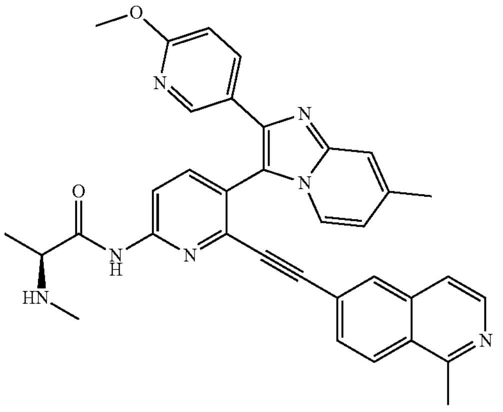

-continued

20

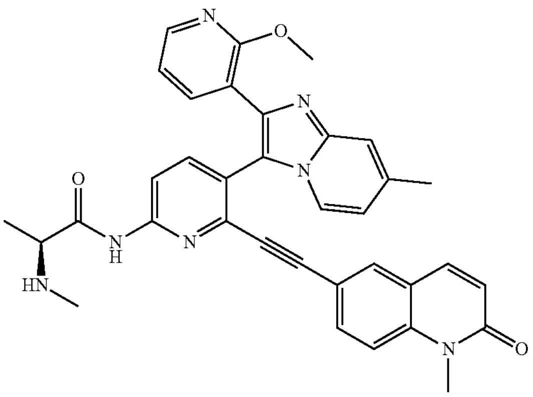

21

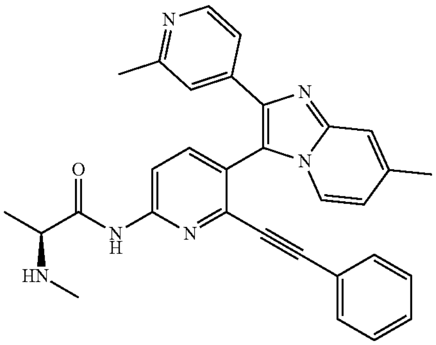

22

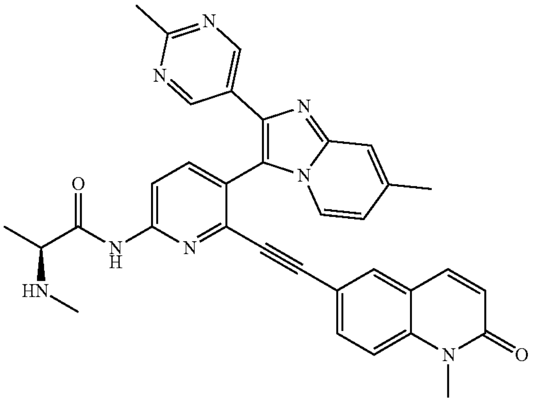

23

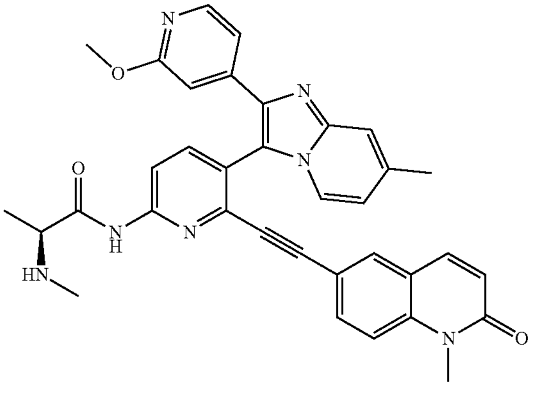

-continued

24

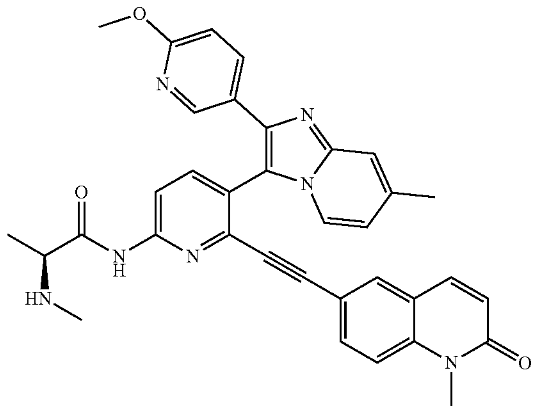

25

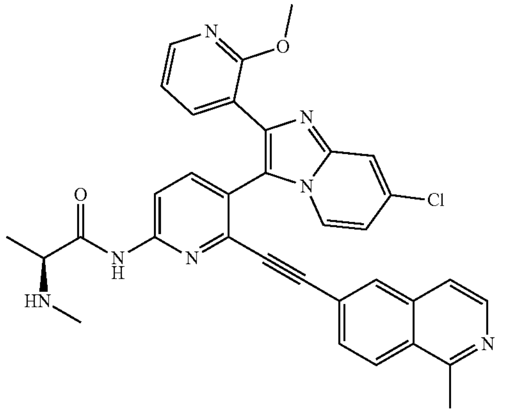

26

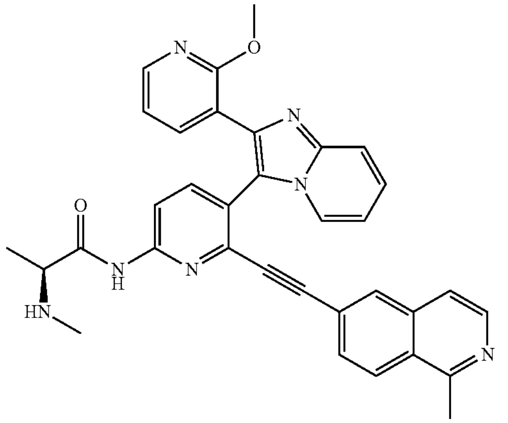

or a pharmaceutically acceptable salt of one of these compounds.

9. The method according to claim 6, wherein the PD-1 pathway inhibitor is an antagonist selected from the group consisting of pembrolizumab, nivolumab, pidilizumab, atezolizumab, avelumab, durvalumab, PDR-001, PD1-1, PD1-2, PD1-3, PD1-4 and PD1-5.

10. The method according to claim 1, wherein the pharmaceutical composition is administered concomitantly, sequentially or alternately with the PD-1 pathway inhibitor or the SMAC mimetic.

11. The method of claim 6, wherein the PD-1 pathway inhibitor is selected from the group consisting of pembrolizumab, nivolumab, pidilizumab, atezolizumab, avelumab, durvalumab, PDR-1, PD1-1, PD1-2, PD1-3, PD1-4 and PD1-5.

12. The method of claim 6, wherein the pharmaceutical composition is administered via a different administration route then the PD-1 pathway inhibitor or the SMAC mimetic.

13. The method of claim 6, wherein the pharmaceutical composition is administered at least once intratumorally and the PD-1 pathway inhibitor or the SMAC mimetic is administered intravenously.

* * * * *

SEQUENCE LISTING

```
Sequence total quantity: 24
SEQ ID NO: 1            moltype = AA  length = 208
FEATURE                 Location/Qualifiers
source                  1..208
                        mol_type = protein
                        organism = Homo sapiens
SEQUENCE: 1
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 2            moltype = AA  length = 232
FEATURE                 Location/Qualifiers
source                  1..232
                        mol_type = protein
                        organism = Homo sapiens
SEQUENCE: 2
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 3            moltype = AA  length = 467
FEATURE                 Location/Qualifiers
source                  1..467
                        mol_type = protein
                        organism = Homo sapiens
SEQUENCE: 3
MGHTRRQGTS PSKCPYLNFF QLLVLAGLSH FCSGVIHVTK EVKEVATLSC GHNVSVEELA  60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSREEMT KNQVSLTCLV KGFYPSDIAV EWESNGQPEN NYKTTPPVLD  420
SDGSFFLYSK LTVDKSRWQQ GNVFSCSVMH EALHNHYTQK SLSLSPG                467

SEQ ID NO: 4            moltype = AA  length = 433
FEATURE                 Location/Qualifiers
source                  1..433
                        mol_type = protein
                        organism = Homo sapiens
SEQUENCE: 4
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDDKT HTCPPCPAPE LLGGPSVFLF PPKPKDTLMI  240
SRTPEVTCVV VDVSHEDPEV KFNWYVDGVE VHNAKTKPRE EQYNSTYRVV SVLTVLHQDW  300
LNGKEYKCKV SNKALPAPIE KTISKAKGQP REPQVYTLPP SREEMTKNQV SLTCLVKGFY  360
PSDIAVEWES NGQPENNYKT TPPVLDSDGS FFLYSKLTVD KSRWQQGNVF SCSVMHEALH  420
NHYTQKSLSL SPG                                                    433

SEQ ID NO: 5            moltype = AA  length = 19
FEATURE                 Location/Qualifiers
source                  1..19
                        mol_type = protein
                        organism = Mus musculus
SEQUENCE: 5
MGWSCIILFL VATATGVHS                                              19

SEQ ID NO: 6            moltype = AA  length = 288
FEATURE                 Location/Qualifiers
source                  1..288
                        mol_type = protein
                        organism = Homo sapiens
SEQUENCE: 6
MGHTRRQGTS PSKCPYLNFF QLLVLAGLSH FCSGVIHVTK EVKEVATLSC GHNVSVEELA  60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
```

-continued

```
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV               288

SEQ ID NO: 7            moltype = AA  length = 422
FEATURE                 Location/Qualifiers
source                  1..422
                        mol_type = protein
                        organism = Vesicular stomatitis virus
SEQUENCE: 7
MSVTVKRIID NTVVVPKLPA NEDPVEYPAD YFRKSKEIPL YINTTKSLSD LRGYVYQGLK  60
SGNVSIIHVN SYLYGALKDI RGKLDKDWSS FGINIGKAGD TIGIFDLVSL KALDGVLPDG  120
VSDASRTSAD DKWLPLYLLG LYRVGRTQMP EYRKKLMDGL TNQCKMINEQ FEPLVPEGRD  180
IFDVWGNDSN YTKIVAAVDM FFHMFKKHEC ASFRYGTIVS RFKDCAALAT FGHLCKITGM  240
STEDVTTWIL NREVADEMVQ MMLPGQEIDK ADSYMPYLID FGLSSKSPYS SVKNPAFHFW  300
GQLTALLLRS TRARNARQPD DIEYTSLTTA GLLYAYAVGS SADLAQQFCV GDNKYTPDDS  360
TGGLTTNAPP QGRDVVEWLG WFEDQNRKPT PDMMQYAKRA VMSLQGLREK TIGKYAKSEF  420
DK                                                                 422

SEQ ID NO: 8            moltype = AA  length = 265
FEATURE                 Location/Qualifiers
source                  1..265
                        mol_type = protein
                        organism = Vesicular stomatitis virus
SEQUENCE: 8
MDNLTKVREY LKSYSRLDQA VGEIDEIEAQ RAEKSNYELF QEDGVEEHTK PSYFQAADDS  60
DTESEPEIED NQGLYAPDPE AEQVEGFIQG PLDDYADEEV DVVFTSDWKQ PELESDEHGK  120
TLRLTSPEGL SGEQKSQWLS TIKAVVQSAK YWNLAECTFE ASGEGVIMKE RQITPDVYKV  180
TPVMNTHPSQ SEAVSDVWSL SKTSMTFQPK KASLQPLTIS LDELFSSRGE FISVGGDGRM  240
SHKEAILLGL RYKKLYNQAR VKYSL                                        265

SEQ ID NO: 9            moltype = AA  length = 2109
FEATURE                 Location/Qualifiers
source                  1..2109
                        mol_type = protein
                        organism = Vesicular stomatitis virus
SEQUENCE: 9
MEVHDFETDE FNDFNEDDYA TREFLNPDER MTYLNHADYN LNSPLISDDI DNLIRKFNSL  60
PIPSMWDSKN WDGVLEMLTS CQANPIPTSQ MHKWMGSWLM SDNHDASQGY SFLHEVDKEA  120
EITFDVVETF IRGWGNKPIE YIKKERWTDS FKILAYLCQK FLDLHKLTLI LNAVSEVELL  180
NLARTFKGKV RRSSHGTNIC RIRVPSLGPT FISEGWAYFK KLDILMDRNF LLMVKDVIIG  240
RMQTVLSMVC RIDNLFSEQD IFSLLNIYRI GDKIVERQGN FSYDLIKMVE PICNLKLMKL  300
ARESRPLVPQ FPHFENHIKT SVDEGAKIDR GIRFLHDQIM SVKTVDLTLV IYGSFRHWGH  360
PFIDYYTGLE KLHSQVTMKK DIDVSYAKAL ASDLARIVLF QQFNDHKKWF VNGDLLPHDH  420
PFKSHVKENT WPTAAQVQDF GDKWHELPLI KCFEIPDLLD PSIIYSDKSH SMNRSEVLKH  480
VRMNPNTPIP SKKVLQTMLD TKATNWKEFL KEIDEKGLDD DDLIIGLKGK ERELKLAGRF  540
FSLMSWKLRE YFVITEYLIK THFVPMFKGL TMADDLTAVI KKMLDSSSGQ GLKSYEAICI  600
ANHIDYEKWN NHQRKLSNGP VFRVMGQFLG YPSLIERTHE FFEKSLIYYN GRPDLMRVHN  660
NTLINSTSQR VCWQGQEGGL EGLRQKGWSI LNLLVIQREA KIRNTAVKVL AQGDNQVICT  720
QYKTKKSRNV VELQGALNQM VSNNEKIMTA IKIGTGKLGL LINDDETMQS ADYLNYGKIP  780
IFRGVIRGLE TKRWSRVTCV TNDQIPTCAN IMSSVSTNAL TVAHFAENPI NAMIQYNYFG  840
TFARLLLMMH DPALRQSLYE VQDKIPGLHS STFKYAMLYL DPSIGGVSGM SLSRFLIRAF  900
PDPVTESLSF WRFIHVHARS EHLKEMSAVF GNPEIAKFRI THIDKLVEDP TSLNIAMGMS  960
PANLLKTEVK KCLIESRQTI RNQVIKDATI YLYHEEDRLR SFLWSINPLF PRFLSEFKSG  1020
TFLGVADGLI SLFQNSRTIR NSFKKKYHRE LDDLIVRSEV SSLTHLGKLH LRRGSCKMWT  1080
CSATHADTLR YKSWGRTVIG TTVPHPLEML GPQHRKETPC APCNTSGFNY VSVHCPDGIH  1140
DVFSSRGPLP AYLGSKTSES TSILQPWERE SKVPLIKRAT RLRDAISWFV EPDSKLAMTI  1200
LSNIHSLTGE EWTKRQHGFK RTGSALHRFS TSRMSHGGFA SQSTAALTRL MATTDTMRDL  1260
GDQNFDFLFQ ATLLYAQITT TVARDGWITS CTDHYHIACK SCLRPIEEIT LDSSMDYTPP  1320
DVSHVLKTWR NGEGSWGQEI KQIYPLEGNW KNLAPAEQSY QVGRCIGFLY GDLAYRKSTH  1380
AEDSSLFPLS IQGRIRGRGF LKGLLDGLMR ASCCQVIHRR SLAHLKRPAN AVYGGLIYLI  1440
DKLSVSPPFL SLTRSGPIRD ELETIPHKIP TSYPTSNRDM GVIVRNYFKY QCRLIEKGKY  1500
RSHYSQLWLF SDVLSIDFIG PFSISTTLLQ ILYKPFLSGK DKNELRELAN LSSLLRSGEG  1560
WEDIHVKFFT KDILLCPEEI RHACKFGIAK DNNKDMSYPP WGRESRGTIT TIPVYYTTTP  1620
YPKMLEMPPR IQNPLLSGIR LGQLPTGAHY KIRSILHGMG IHYRDFLSCG DGSGGMTAAL  1680
LRENVHSRGI FNSLLELSGS VMRGASPEPP SALETLGGDK SRCVNGETCW EYPSDLCDPR  1740
TWDYFLRLKA GLGLQIDLIV MDMEVRDSST SLKIETNVRN YVHRILDEQG VLIYKTYGTY  1800
ICESEKNAVT ILGPMFKTVD LVQTEFSSSQ TSEVYMVCKG LKKLIDEPNP DWSSINESWK  1860
NLYAFQSSEQ EFARAKKVST YFTLTGIPSQ FIPDPFVNIE TMLQIFGVPT GVSHAAALKS  1920
SDRPADLLTI SLFYMAIISY YNINHIRVGP IPPNPPSDGI AQNVGIAITG ISFWLSLMEK  1980
DIPLYQQCLA VIQQSFPIRW EAVSVKGGYK QKWSTRGDGL PKDTRISDSL APIGNWIRSL  2040
ELVRNQVRLN PFNEILFNQL CRTVDNHLKW SNLRRNTGMI EWINRRISKE DRSILMLKSD  2100
LHEENSWRD                                                          2109

SEQ ID NO: 10           moltype = AA  length = 229
FEATURE                 Location/Qualifiers
source                  1..229
                        mol_type = protein
                        organism = Vesicular stomatitis virus
SEQUENCE: 10
```

-continued

```
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF LGSSNLKATP  120
AVLADQGQPE YHAHCEGRAY LPHRMGKTPP MLNVPEHFRR PFNIGLYKGT IELTMTIYDD  180
ESLEAAPMIW DHFNSSKFSD FREKALMFGL IVEKKASGAW VLDSIGHFK             229

SEQ ID NO: 11          moltype = AA  length = 498
FEATURE                Location/Qualifiers
source                 1..498
                       mol_type = protein
                       organism = unidentified
                       note = Lymphocytic choriomeningitis mammarenavirus
SEQUENCE: 11
MGQIVTMFEA LPHIIDEVIN IVIIVLIIIT SIKAVYNFAT CGILALVSFL FLAGRSCGMY  60
GLNGPDIYKG VYQFKSVEFD MSHLNLTMPN ACSANNSHHY ISMGSSGLEL TFTNDSILNH  120
NFCNLTSAFN KKTFDHTLMS IVSSLHLSIR GNSNHKAVSC DFNNGITIQY NLSFSDPQSA  180
ISQCRTFRGR VLDMFRTAFG GKYMRSGWGW AGSDGKTTWC SQTSYQYLII QNRTWENHCR  240
YAGPFGMSRI LFAQEKTKFL TRRLAGTFTW TLSDSSGVEN PGGYCLTKWM ILAAELKCFG  300
NTAVAKCNVN HDEEFCDMLR LIDYNKAALS KFKQDVESAL HVFKTTVNSL ISDQLLMRNH  360
LRDLMGVPYC NYSKFWYLEH AKTGETSVPK CWLVTNGSYL NETHFSDQIE QEADNMITEM  420
LRKDYIKRQG STPLALMDLL MFSTSAYLIS IFLHLVKIPT HRHIKGGSCP KPHRLTNKGI  480
CSCGAFKVPG VKTIWKRR                                               498

SEQ ID NO: 12          moltype = AA  length = 498
FEATURE                Location/Qualifiers
source                 1..498
                       mol_type = protein
                       organism = unidentified
                       note = Dandenong virus
SEQUENCE: 12
MGQLITMFEA LPHIIDEVIN IVIIVLVIIT SIKAVYNFAT CGIIALISFC LLAGRSCGLY  60
GVTGPDIYKG LYQFKSVEFN MSQLNLTMPN ACSANNSHHY ISMGKSGLEL TFTNDSIISH  120
NFCNLTDGFK KKTFDHTLMS IVASLHLSIR GNTNYKAVSC DFNNGITIQY NLSFSDAQSA  180
INQCRTFRGR VLDMFRTAFG GKYMRSGYGW KGSDGKTTWC SQTSYQYLII QNRTWENHCE  240
YAGPFGLSRV LFAQEKTKFL TRRLAGTFTW TLSDSSGTEN PGGYCLTKWM LIAAELKCFG  300
NTAVAKCNIN HDEEFCDMLR LIDYNKAALK KFKEDVESAL HLFKTTVNSL ISDQLLMRNH  360
LRDLMGVPYC NYSKFWYLEH VKTGDTSVPK CWLVSNGSYL NETHFSDQIE QEADNMITEM  420
LRKDYIKRQG STPLALMDLL MFSTSAYLIS VFLHLMKIPT HRHIKGGTCP KPHRLTSKGI  480
CSCGAFKVPG VKTVWKRR                                               498

SEQ ID NO: 13          moltype = AA  length = 489
FEATURE                Location/Qualifiers
source                 1..489
                       mol_type = protein
                       organism = unidentified
                       note = Mopeia mammarenavirus
SEQUENCE: 13
MGQIVTFFQE VPHILEEVMN IVLMTLSILA ILKGIYNVMT CGIIGLITFL FLCGRSCSSI  60
YKDNYEFFSL DLDMSSLNAT MPLSCSKNNS HHYIQVGNET GLELTLTNTS IIDHKFCNLS  120
DAHRRNLYDK ALMSILTTFH LSIPDFNQYE AMSCDFNGGK ISIQYNLSHS NYVDAGNHCG  180
TIANGIMDVF RRMYWSTSLS VASDISGTQC IQTDYKYLII QNTSWEDHCM FSRPSPMGFL  240
SLLSQRTRNF YISRRLLGLF TWTLSDSEGN DMPGGYCLTR SMLIGLDLKC FGNTAIAKCN  300
QAHDEEFCDM LRLFDFNKQA ISKLRSEVQQ SINLINKAVN ALINDQLVMR NHLRDLMGIP  360
YCNYSKFWYL NDTRTGRTSL PKCWLVTNGS YLNETQFSTE IEQEANNMFT DMLRKEYEKR  420
QSTTPLGLVD LFVFSTSFYL ISVFLHLIKI PTHRHIKGKP CPKPHRLNHM AICSCGFYKQ  480
PGLPTQWKR                                                         489

SEQ ID NO: 14          moltype = AA  length = 446
FEATURE                Location/Qualifiers
source                 1..446
                       mol_type = protein
                       organism = Homo sapiens
SEQUENCE: 14
EVMLVESGGG LVQPGGSLRL SCTASGFTFS ASAMSWVRQA PGKGLEWVAY ISGGGGDTYY  60
SSSVKGRFTI SRDNAKNSLY LQMNSLRAED TAVYYCARHS NVNYYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 15          moltype = AA  length = 218
FEATURE                Location/Qualifiers
source                 1..218
                       mol_type = protein
                       organism = Homo sapiens
SEQUENCE: 15
EIVLTQSPAT LSLSPGERAT MSCRASENID TSGISFMNWY QQKPGQAPKL LIYVASNQGS  60
GIPARFSGSG SGTDFTLTIS RLEPEDFAVY YCQQSKEVPW TFGQGTKLEI KRTVAAPSVF  120
```

-continued

```
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 16          moltype = AA  length = 446
FEATURE                Location/Qualifiers
source                 1..446
                       mol_type = protein
                       organism = Homo sapiens
SEQUENCE: 16
EVMLVESGGG LVQPGGSLRL SCTASGFTFS ASAMSWVRQA PGKGLEWVAY ISGGGGDTYY  60
SSSVKGRFTI SRDNAKNSLY LQMNSLRAED TAVYYCARHS NPNYYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 17          moltype = AA  length = 218
FEATURE                Location/Qualifiers
source                 1..218
                       mol_type = protein
                       organism = Homo sapiens
SEQUENCE: 17
EIVLTQSPAT LSLSPGERAT MSCRASENID TSGISFMNWY QQKPGQAPKL LIYVASNQGS  60
GIPARFSGSG SGTDFTLTIS RLEPEDFAVY YCQQSKEVPW TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 18          moltype = AA  length = 446
FEATURE                Location/Qualifiers
source                 1..446
                       mol_type = protein
                       organism = Homo sapiens
SEQUENCE: 18
EVMLVESGGG LVQPGGSLRL SCTASGFTFS KSAMSWVRQA PGKGLEWVAY ISGGGGDTYY  60
SSSVKGRFTI SRDNAKNSLY LQMNSLRAED TAVYYCARHS NVNYYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 19          moltype = AA  length = 218
FEATURE                Location/Qualifiers
source                 1..218
                       mol_type = protein
                       organism = Homo sapiens
SEQUENCE: 19
EIVLTQSPAT LSLSPGERAT MSCRASENID VSGISFMNWY QQKPGQAPKL LIYVASNQGS  60
GIPARFSGSG SGTDFTLTIS RLEPEDFAVY YCQQSKEVPW TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 20          moltype = AA  length = 446
FEATURE                Location/Qualifiers
source                 1..446
                       mol_type = protein
                       organism = Homo sapiens
SEQUENCE: 20
EVMLVESGGG LVQPGGSLRL SCTASGFTFS KSAMSWVRQA PGKGLEWVAY ISGGGGDTYY  60
SSSVKGRFTI SRDNAKNSLY LQMNSLRAED TAVYYCARHS NVNYYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 21          moltype = AA  length = 218
FEATURE                Location/Qualifiers
source                 1..218
                       mol_type = protein
                       organism = Homo sapiens
SEQUENCE: 21
EIVLTQSPAT LSLSPGERAT MSCRASENID VSGISFMNWY QQKPGQAPKL LIYVASNQGS  60
GIPARFSGSG SGTDFTLTIS RLEPEDFAVY YCQQSKEVPW TFGQGTKLEI KRTVAAPSVF  120
IFPPSDEQLK SGTASVVCLL NNFYPREAKV QWKVDNALQS GNSQESVTEQ DSKDSTYSLS  180
```

-continued

```
STLTLSKADY EKHKVYACEV THQGLSSPVT KSFNRGEC                          218

SEQ ID NO: 22          moltype = AA  length = 446
FEATURE                Location/Qualifiers
source                 1..446
                       mol_type = protein
                       organism = Homo sapiens
SEQUENCE: 22
EVMLVESGGG LVQPGGSLRL SCTASGFTFS KSAMSWVRQA PGKGLEWVAY ISGGGGDTYY  60
SSSVKGRFTI SRDNAKNSLY LQMNSLRAED TAVYYCARHS NVNYYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 23          moltype = AA  length = 218
FEATURE                Location/Qualifiers
source                 1..218
                       mol_type = protein
                       organism = Homo sapiens
SEQUENCE: 23
EIVLTQSPAT LSLSPGERAT MSCRASENID VSGISFMNWY QQKPGQAPKL LIYVASNQGS  60
GIPARFSGSG SGTDFTLTIS RLEPEDFAVY YCQQSKEVPW TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 24          moltype = RNA  length = 12603
FEATURE                Location/Qualifiers
source                 1..12603
                       mol_type = unassigned RNA
                       organism = Vesicular stomatitis virus
SEQUENCE: 24
tgcttctgtt tgtttggtaa taatagtaat tttccgagtc ctctttgaaa ttgtcattag  60
ttttacagac aatgtcagtt ctcttagtaa ctgttgtgtc agcatcaagg ttttgaagga  120
cgtttactcc taggtcacct tatgggccgt ctaatgaagt cttttagttt cctctaagga  180
gaaatgtagt tatgatgttt ttcaaacagt ctagattctc ctatacagat ggttccggag  240
tttaggcctt tacatagtta gtatgtacag ttgtcgatga acatacctcg taatttcctg  300
taggccccat tcaacctatt tctaaccagt tcaaagcctt atttgtagcc ctttcgtccc  360
ctatgttagc cttataaact ggaacatagg aactttcggg acctgccgca tgaaggtcta  420
cctcatagcc tacgaaggtc ttggtcgcgt ctactgttta ccaacggaaa catagatgaa  480
ccgaatatgt ctcacccgtc ttgtgtttac ggacttatgt cttttttcga gtacctaccc  540
gactgtttag ttacgtttta ctagttactt gtcaaacttg gagaacacgg tcttccagca  600
ctgtaaaaac tacacacccc tttactgtca ttaatgtgtt tttaacagcg acgtcacctg  660
tacaagaagg tgtacaagtt ttttgtactt acacggagca agtctatgcc ttgataacaa  720
aggtctaagt ttctaacacg acgtaaccgt tgtaaacctg tggagacgtt ttattggcct  780
tacagatgtc ttctacattg ctggacctag aacttggctc ttcaacgtct actttaccag  840
gtttactacg aaggtccggt tctttaactg ttccggctaa gtatgtacgg aataaactag  900
ctgaaaccta acagaagatt cagaggtata agaaggcagt ttttgggacg gaaggtgaag  960
acccccgtta actgtcgaga agacgagtct aggtggtctc gttccttacg ggctgtcgga  1020
ctactgtaac tcatatgtag agaatgatgt cgtccaaaca acatgcgaat acgtcatcct  1080
aggagacggc tgaaccgtgt tgtcaaaaca caacctctat tgtttatgtg aggtctacta  1140
tcatggcctc ctaactgctg attacgtggc ggtgttccgt ctctacacca gcttaccgag  1200
cctaccaaac ttctagtttt gtcttttggc tgaggactat actacgtcat acgcttttct  1260
cgtcagtaca gtgacgttcc ggattctctc ttctgttaac cgttcatacg attcagtctt  1320
aaactgttta ctgggatatt aagagtctag tggataatat ataatacgat gtatactttt  1380
tttgattgtc tatagtacct attagagtgt tttcaagcac tcatagagtt caggataaga  1440
gcagacctag tccgccatcc tctctatcta ctctagcttc gtgttgctcg acttttcagg  1500
ttaatactca acaaggttct cctacctcac cttctcgtat gattcgggag aataaaagtc  1560
cgtcgtctac taagactgtg tcttagactt ggtctttaac ttctgttagt tccgaacata  1620
cgtggtctag gtcttcgact cgttcaactt ccgaaatatg tccccggaaa tctactgata  1680
cgtctactcc ttcacctaca acataaatga agcctgacct ttgtcggact cgaacttaga  1740
ctgctcgtac ctttctggaa tgccaactgt agcggtctcc caaattcacc tctcgtcttt  1800
agggtcaccg aaagctgcta atttcgtcag cacgtttcac ggtttatgac cttagaccgt  1860
ctcacgtgta aacttcgtag ccctcttccc cagtaatact tcctcgcggt ctattgaggc  1920
ctacatatat tccagtgagg tcactacttg tgtgtaggca gggttagtct tcgtcatagt  1980
ctacaaacca gagagagttt ctgtaggtac tgaaaggttg ggttctttcg ttcagaagtc  2040
ggagagtggt ataggaacct acttaacaag agtagatctc ctctcaagta gagacagcct  2100
ccactgcctg cttacagagt atttctccgg taggacgagc cggactctat gtttttcaac  2160
atgttagtcc gctctcagtt tataagagac atctgatact ttttttcatt gtctatagtg  2220
ctagattcac aataggttta ggtaagtagt actcaaggaa tttcttctaa gagccagact  2280
tccccttccc attctttaga ttctttaatc cctagcgtgg tgggggaata cttctcctgt  2340
gatcgtacct catacgaggc tcgcgaggtt aactgtttag gataaaacct caactgctct  2400
acctgtggat actaggctta gttaattcta tactctttaa gaagaaatgt cacttttact  2460
gccaatctag attagcaggc aagtcttgta tgagtctaca ccgtcggcga catagggtaa  2520
ccctagtgta catgtagcct taccgtccct ttgcagggaa gatgttttag aaccgaaaaa  2580
acccaagaag attagatttc cggtgaggtc gccataaccg tctagttcca gttggtctca  2640
tagtgcgagt gacgcttccg tcccgaataa acggtgtatc ctaccccttc tggggagggt  2700
```

-continued

```
acgagttaca tggtctcgtg aagtcttctg gtaagttata tccagaaatg ttcccttgct  2760
aactcgagtg ttactggtag atgctactac tcagtgacct tcgtcgagga tactagaccc  2820
tagtaaagtt aagaaggttt aaaagactaa agtctctctt ccggaattac aaaccggact  2880
aacagctctt tttccgtaga cctcgcaccc aggacctgag atagccggtg aagtttactc  2940
gatcagattg aagatcgaag acttgttagg ggccaaatga gtcagagggg attaaggtcg  3000
gagagcttgt tgattatagg acagaaaaga tagggatact ttttttgatt gtctctagct  3060
agacaaatgc gcagtgccta gggggcccga cgtccttaag cggtggtacc cggtctagca  3120
ctggtacaag ctccgggacg gggtgtagta gctgctccac tagttgtagc actagtagca  3180
cgagtagtag tagtggtcgt agttccggca catgttgaag cggtggacgc cgtaggaccg  3240
ggaccactcg aaggacaagg accggccgtc ttcgacgccg tacatgccgg acttaccggg  3300
gctatagatg ttcccgcaca tggtcaagtt ctcgcacctc aagctgtact cggtggactt  3360
ggagtggtac gggttgcgga cgtcgcggtt gttatcggtg gtgatgtagt cgtacccgtc  3420
gtcgccggac ctcaactgga agtggttgct gtcgtaggac ttggtgttga agacgttgga  3480
gtggtcgcgg aagttgttct tttggaagct ggtgtgggag tactcgtagc actcgtcgga  3540
cgtggactcg tagtctccgt tgtcgttggt gttccggcac tcgacgctga agttgttgcc  3600
gtagtggtag gtcatgttgg actcgaagtc gctaggagtc tcgcggtagt cggtcacgtc  3660
ttggaagtct ccgtctcacg acctgtacaa gtcttggcgg aagccgccgt tcatgtactc  3720
ttcgccgacc ccgacccggc cgtcgctgcc gttctggtgg accacgtcgg tctggtcgat  3780
ggtcatggag tagtaggtct tgtcttggac cctcttggtg acgtctatgc ggcctggaaa  3840
gccgtactcg tcttaggaca agcgggtcct cttttggttc aaggagtggt cctctgaccg  3900
gccgtggaag tggacctggg actcgctgtc gtcgccgcac ctcttgggac cgccgatgac  3960
ggagtggttc acctactagg accggcggct cgacttcacg aagccgttgt ggcggcaccg  4020
gttcacgttg cacttggtgc tgctcctcaa gacgctgtac gactctgagt agctgatgtt  4080
gttccggcgg gactcgttca agttcgtcct gcacctctcg cgggacgtgc acaagttctg  4140
gtggcacttg tcggagtagt cgctggtcga cgagtactct ttggtggact ctctggagta  4200
cccgcacggg atgacgttga tgtcgttcaa gaccatagac ctcgtgcggt tctggccgct  4260
ctggtcgcac gggttcacga ccgaccactg gttaccgtcg atggacttgc tctgggtgaa  4320
gtcgctggtc tagctcgtcc ttcggctgtt gtactagtgg ctctacgact ccttcctgat  4380
gtagttctct gtcccgtcgt ggggggaccg ggagtaccta gacgagtaca agtcgtggtc  4440
gcggatggag tagtcgtaga aggacgtgga ccacttctag gggtgggtgt ctgtgtagtt  4500
cccgccgtcg acggggttcg gggtgtctga gtggttgttc ccgtagacgt cgacgccgcg  4560
gaagttccac gggccgcact tttggtagac cttctcctct attcgccggc gatgctggag  4620
ctgatacttt ttttgattgt ctataggagc tgcggtggta cccggtgtgt tcttccgtcc  4680
cttgttcggg gtcgttcacg gggatggact tgaagaaagt cgacgaccac gaccggccgg  4740
actcggtgaa aacaagaccg cactaggtgc actggtttct tcactttctc cagcggtgtg  4800
actcgacgcc ggtgttgcaa agtcaccttc ttgaccgggt ctggtcttag atgaccgtct  4860
ttcttttctt ttaccacgac tggtactact cgccgctgta cttgtagacc gggctcatgt  4920
tcttggcctg gtagaagctg tagtggttgt tggactcgta gcactaagac cgggactccg  4980
gaagactact cccgtggata ctcacgcacc acgacttcat gctcttcctg cggaagttcg  5040
cgctcgtaga ccggcttcac tgtgactcgc acttccggct gaaagggtgt ggatcgtagt  5100
cgctgaagct ctaggggtgg tcgttgtagt ctgcctagta gacatcgtgg tcgccgccga  5160
aaggtctcgg agtagacaga accgaccttt tgccgctcct tgacttgcgg tagttgtggt  5220
ggcacagagt cctggggctc tgtctcgaca tacggcacag gtcgttcgac ctgaagttgt  5280
actggtggtt ggtgtcgaag tacacggact aattcatgcc ggtggactct cacttggtct  5340
ggaagttgac cttgtggtgg ttcgttctcg tgaaggggct gctgttctgg gtgtggacag  5400
gaggtacagg acgaggtctt gacgagccgc ctgggaggca caaagacaag ggaggtttcg  5460
gattcctgtg ggactactag tcgtcttggg gacttcactg gacgcaccac cacctacaca  5520
gagtgctcct gggtcttcac ttcaagttaa ccatgcacct gccgcacctt cacgtgttgc  5580
ggttctggtt cggatctctc cttgtcatgt tgtcgtggat gtctcaccac aggcacgact  5640
ggcacgacgt agtcctgacc gacttgccgt ttctcatgtt cacgttccac aggttgttcc  5700
gggacggacg aggatagctc ttttggtagt cgttccggtt ccctgtcggg gcccttggag  5760
ttcacatatg ggacggagga tcggcccttc tctactggtt cttagtccac agggactgga  5820
cggagcactt cccgaagatg ggaaggctat agcggcacct taccctctcg ttaccggtcg  5880
gactcttgtt gatgttctgt tggggaggac acgacctgtc gctgccgagt aagaaggaca  5940
tgtcgtttga ctggcacctg ttctcgtcta ccgtcgtccc gttacacaag tcgacgtcgc  6000
actacgtgct ccgggacgtg ttggtgatgt gggtcttttc ggactcggac agaggaccga  6060
ctagttgatc ggtctaagaa gtacaaacct ggtttagttg aacactatgg tacgagtttc  6120
tccggagtta atataaactc aaaaattaaa aatacttttt ttgattgtcg ttagtacctt  6180
caggtgctaa aactctggct gctcaagtta ctaaagttac ttctactgat acggtgttct  6240
cttaaggact tagggctact cgcgtactgc atgaacttag tacgactaat gttggactta  6300
agaggagatt aatcactact ataactgtta aattagtcct ttaagttaag agaaggttaa  6360
gggagctaca ccctatcatt cttgacccta cctcaagaac tctacaattg cagtacagtt  6420
cggttagggt agggttgtag agtctacgta tttacctacc cttcaaccaa ttacagacta  6480
ttagtactac ggtcagttcc catatcaaaa aatgtacttc acctgtttct ccgtctttat  6540
tgtaaactgc accacctctg gaagtaggcg ccgaccccgt tgtttggtta acttatgtag  6600
tttttccttt ctacctgact gagtaagttt taagagcgaa taaacacagt tttcaaaaac  6660
ctgaatgtgt tcaactgtaa ttagaattta cgacagagac tccaccttaa cgagttgaac  6720
cgctcctgaa agtttccgtt tcagtcttct tcaagagtac cttgcttgta tacgtcctaa  6780
tcccaagggt cgaacccagg atgaaaataa agtcttccta cccgaatgaa gttctttgaa  6840
ctataagatt acctggcttt gaaagacaat taccagtttc tacactaata tccctcctac  6900
gtttgccacg ataggtacca tacatcttat ctgttggaca agagtctcgt tctgtagaag  6960
agggaagatt tatagatgtc ttaacctcta ttttaacacc tctccgtccc tttaaaaaga  7020
atactgaact aattttacca ccttggctat acgttgaact tcgactactt taatcgttct  7080
cttagttccg gaaatcaggg tgttaaggga gtaaaacttt tagtatagtt ctgaagacaa  7140
```

-continued

```
ctacttcccc gtttttaact ggctccatat tctaaggagg tactagtcta ttactcacac  7200
ttttgtcacc tagagtgtga ccactaaata cctagcaagt ctgtaacccc agtaggaaaa  7260
tatctaataa tgtgacctga tctttttaat gtaagggttc attggtactt ctttctataa  7320
ctacacagta tacgttttcg tgaacgttca ctaaatcgag cctaacaaga taaagttgtc  7380
aagttactag tatttttcac caagcactta cctctgaacg agggagtact agtagggaaa  7440
ttttcagtac aatttctttt atgtaccggg tgtcgacgag ttcaagttct aaaacctcta  7500
tttaccgtac ttgaaggcga ctaatttaca aaactttatg ggctgaatga tctgggtagc  7560
tattatatga gactgttttc agtaagttac ttatccagtc tccacaactt tgtacaggct  7620
tacttaggct tgtgaggata gggatcattt ttccacaacg tctgatacaa cctgtgtttc  7680
cgatggttaa cctttcttaa agaatttctc taactactct tcccgaatct actactacta  7740
gattaataac cagaatttcc tttcctctcc cttgacttca accgtccatc taaaaagagg  7800
gattacagaa cctttaacgc tcttatgaaa cattaatggc ttataaacta tttctgagta  7860
aagcagggat acaaatttcc ggactgttac cgcctgctag attgacgtca gtaatttttc  7920
tacaatctaa ggagtaggcc ggttcctaac ttcagtatac tccgttaaac gtatcggtta  7980
gtgtaactaa tgctttttac cttattggtg gtttccttca atagtttgcc gggtcacaag  8040
gctcaatacc cggtcaagaa tccaataggt aggaattagc tctcttgagt acttaaaaaa  8100
ctcttttcag aatatatgat gttaccttct ggtctgaact acgcacaagt gttgttgtgt  8160
gactagttaa gttggagggt tgctcaaaca accgttcctg ttctcccacc tgaccttcca  8220
gatgccgttt ttcctacctc ataggagtta gatgaccaat aagtttctct ccgattttag  8280
tctttgtgac gacagtttca gaaccgtgtt ccactattag ttcaataaac gtgtgtcata  8340
ttttgcttct ttagctcttt gcaacatctt aatgtcccac gagagttagt ttaccaaaga  8400
ttattactct tttaatactg acgttagttt tatccctgtc ccttcaatcc tgaaaactat  8460
ttactgctac tctgatacgt tagacgtcta atgaacttaa taccttttta tggctaaaag  8520
gcacctcact aatctcccaa tctctggttc tctaccagtg ctcactgaac acagtggtta  8580
ctggtttatg ggtgaacacg attatattac tcgagtcaaa ggtgtttacg agagtggcat  8640
cgagtaaaac gactcttggg ttagttacgg tactatgtca tgttaataaa accctgtaaa  8700
cgatctgaga acaactacta cgtactagga cgagaagcag ttagtaacat acttcaagtt  8760
ctattctatg gcccgaacgt gtcaagatga aagtttatgc ggtacaacat aaacctggga  8820
aggtaacctc ctcacagccc gtacagaaac aggtccaaaa actaatctcg gaagggtcta  8880
gggcattgtc tttcagagag taagacctct aagtaggtac atgtacgagc ttcactcgta  8940
gacttcctct actcacgtca taaacctttg gggctctatc ggttcaaagc ttattgagtg  9000
tatctgttcg atcatcttct aggttggaga gacttgtagc gataccctta ctcaggtcgc  9060
ttgaacaatt tctgactcca attttttacg aattagctta gttctgtttg gtagtccttg  9120
gtccactaat tcctacgttg gtatataaac atagtacttc tcctagccga gtcttcaaag  9180
aataccagtt atttaggaga caagggatct aaaaattcac ttaagtttag tccgtgaaaa  9240
aaccctcagc gtctgcccga gtagtcagat aaagttttaa gagcatgata agccttgagg  9300
aaattctttt tcatagtatc ccttaaccta ctaaactaac actcctcact ccataggaga  9360
aactgtgtaa atccctttga agtaaactct tcccctagta cattttacac ctgtacaagt  9420
cgatgagtac gactgtgtaa ttctatgttt aggaccccgg catgtcaata accctgttga  9480
catggggtag gtaatcttta caacccaggt gttgtagctt ttctctgagg aacacgtggt  9540
acattgtgta gtcccaagtt aatacaaaga cacgtaacag gtctgcccta ggtactgcag  9600
aaatcaagtg cccctggtaa cggacgaata gatcccagat tttgtagact tagatgtaga  9660
taaaacgtcg gaaccctttc cctttcgttt cagggtgact aattttctcg atgtgcagaa  9720
tctctacgat agagaaccaa acaacttggg ctgagatttg atcgttactg atatgaaaga  9780
ttgtaggtga gaaattgtcc gcttcttacc tggttttccg tcgtacccaa gttttcttgt  9840
cccagacggg aagtatccaa aagctgtaga gcctactcgg taccacccaa gcgtagagtc  9900
tcgtgacgtc gtaactggtc caactaccgt tgatgtctgt ggtactccct agaccctcta  9960
gtcttaaagc tgaaaaataa ggttcgttgc aacgagatac gagtttaatg gtggtgacaa  10020
cgttctctgc ctacctagtg gtcaacatgt ctagtaatag tataacggac attcaggaca  10080
aactctgggt atcttctcta gtgggacctg agttcatacc tgatgtgcgg gggtctacat  10140
agggtacacg acttctgtac ctccttaccc cttccaagca cccctgttct ctattttgtc  10200
tagataggaa atcttccctt aaccttctta aatcgtggac gactcgttag gatagttcag  10260
ccgtctacat atccaaaaga tatacctctg aaccgcatat cttttagatg agtacggctc  10320
ctgtcaagag ataaaggaga tagatatgtt ccagcataat ctccagctcc aaagaatttt  10380
cccaacgatc tgcctaatta ctctcgttca acgacggttc attatgtggc ctcttcagac  10440
cgagtaaact tctccggccg gttgcgtcac atgcctccaa actaaatgaa ctaactattt  10500
aactcacata gtggaggtaa ggaaagagaa tgatctagtc ctggataatc tctgcttaat  10560
ctttgctaag ggtgttctta gggttggagg ataggctgtt cgttggcact atacccccac  10620
taacagtctt taatgaagtt tatggttacg gcagattaac ttttcccttt tatgtctagt  10680
gtaataagtg ttaataccaa taagagtcta cagaataggt atctgaagta acctggtaag  10740
agataaaggt ggtgggagaa cgtttaggat atgttcggta aaaatagacc ctttctattc  10800
ttactcaact ctctcgaccg tttagaaaga agtaacgatt ctagtcctct ccccaccctt  10860
ctgtatgtac actttaagaa gtggttcctg tataataaca caggtctcct ttagtctgta  10920
cgaacgttca agccctaacg attcctatta ttatttctgt actcgatagg gggaacccct  10980
tcccttaggt ctccctgtta atgttgttag ggacaaataa tatgctggtg gggaatgggt  11040
ttctacgatc tctacggagg ttcttaggtt ttaggggacg acaggcctta gtccaacccg  11100
gttaatggtt gaccgcgagt aatattttaa gcctcatata atgtacctta cccttaggta  11160
atgtccctga agaactcaac acctctgccg aggcctccct actgacgacg taatgatgct  11220
cttttacacg tatcgtctcc ttataagtta tcagacaatc ttaatagtcc cagtcagtac  11280
gctccgcgga gaggactcgg ggggtcacgg gatctttgaa atcctcctct atttagctct  11340
acacatttac cactttgtac aaccccttata ggtagactga atacactggg ttcctgaacc  11400
ctgataaagg aggctgagtt tcgtccgaac cccgaagttt aactaaatta acattaccta  11460
taccttcaag ccctaagaag atgatcggac ttttaactct gcttacaatc tttaatacac  11520
gtggcctaaa acctactcgt tcctcaaaat tagatgttct gaataccttg tatataaaca  11580
ctctcgcttt tcttacgtca ttgttaggaa ccagggtaca agttctgcca gctgaatcaa  11640
gtttgtctta aatcatcaag agtttgcaga cttcatatat accatacatt tccaaacttc  11700
tttaattagc tacttgggtt agggctaacc agaaggtagt tacttaggac ctttttggac  11760
atgcgtaagg tcagtagtct tgtccttaaa cggtctcgtt tcttccaatc atgtatgaaa  11820
tggaactgtc cataagggag ggttaagtaa ggactaggaa aacatttgta actctgatac  11880
```

-continued

```
gatgtttata agcctcatgg gtgcccacac agagtacgcc gacggaattt tagtagacta  11940
tctggacgtc taaataactg gtaatcggaa aaaatatacc gctaatatag cataatattg  12000
tagttagtat agtctcatcc tggctatgga ggcttggggg gtagtctacc ttaacgtgtt  12060
ttacaccccct agcgatattg accatattcg aaaaccgact caaactacct ctttctgtaa  12120
ggtgatatag ttgtcacaaa tcgtcaatag gtcgttagta agggctaatc caccctccga  12180
caaagtcatt ttcctcctat gttcgtcttc acctcatgat ctccactacc cgagggtttt  12240
ctatgggctt aaagtctgag gaaccggggt tagcccttga cctagtctag agaccttaac  12300
caggctttgg ttcaagcaga tttaggtaag ttactctaga acaagttagt cgatacagca  12360
tgtcacctat tagtaaactt taccagttta aacgcttctt tgtgtcctta ctaacttacc  12420
tagttatctg cttaaagttt tcttctggcc agatatgact acaacttctc actggatgtg  12480
ctccttttga gaacctctct aattttttag tactcctctg aggtttgaaa ttcatacttt  12540
ttttgaaact aggaattctg ggagaacacc aaaaataaaa aatagaccaa aacaccagaa  12600
gca                                                                12603
```